United States Patent
Monazami et al.

(10) Patent No.: US 11,768,016 B2
(45) Date of Patent: Sep. 26, 2023

(54) THERMAL MANAGEMENT DEVICE AND SYSTEM

(71) Applicant: BLUEXTHERMAL, INC., Cambridge, MA (US)

(72) Inventors: Reza Monazami, Boston, MA (US); Sahar Jahani, Boston, MA (US); Nicholas Keith Anselmo, Yorktown, VA (US)

(73) Assignee: BLUEXTHERMAL, INC., Cambridge, MA (US)

( * ) Notice: Subject to any disclaimer, the term of this patent is extended or adjusted under 35 U.S.C. 154(b) by 0 days.

(21) Appl. No.: 16/936,358

(22) Filed: Jul. 22, 2020

(65) Prior Publication Data
US 2021/0123641 A1 Apr. 29, 2021

Related U.S. Application Data

(60) Provisional application No. 62/877,122, filed on Jul. 22, 2019, provisional application No. 62/954,759, filed on Dec. 30, 2019.

(51) Int. Cl.
*F25B 21/02* (2006.01)
*F28D 15/02* (2006.01)
(Continued)

(52) U.S. Cl.
CPC ............ *F25B 21/02* (2013.01); *A61B 18/203* (2013.01); *A61F 7/007* (2013.01);
(Continued)

(58) Field of Classification Search
CPC .................. F25B 21/02; A61B 18/203; A61B 2018/00452; A61F 7/007;
(Continued)

(56) References Cited

U.S. PATENT DOCUMENTS 5,737,923 A 4/1998 Gilley et al.
6,233,944 B1 5/2001 Yamada et al.
(Continued)

FOREIGN PATENT DOCUMENTS

CA 2275387 A1 * 4/1999
JP H11121816 A * 4/1999
WO WO-2016014710 A1 * 1/2016 ............... F01D 5/18

OTHER PUBLICATIONS

PCT International Search Report for PCT Application No. PCT/US2020/043151, filed Jul. 22, 2020, 20 pages.
(Continued)

*Primary Examiner* — Ljiljana V. Ciric
(74) *Attorney, Agent, or Firm* — Perkins Coie LLP

(57) ABSTRACT

Thermal management systems including a thermoelectric component, a two-phase heat transfer unit, and a controller are disclosed herein. The heat transfer unit has a phase-transition chamber and microfeatures in the phase-transition chamber that induce capillary forces to a working fluid that drives the working fluid through the phase-transition chamber. The controller is configured to operate the thermoelectric component and the heat transfer unit such that the heat transfer unit cools one side of the thermoelectric component to a first temperature and the thermoelectric component changes the temperature of a target material on its other side to a second temperature of +/−60° C. of the first temperature within 0.5-20 seconds.

23 Claims, 28 Drawing Sheets

(51) Int. Cl.
  *F28D 15/04* (2006.01)
  *A61F 7/00* (2006.01)
  *H01L 23/38* (2006.01)
  *A61B 18/20* (2006.01)
  *H10N 10/00* (2023.01)
  *H10N 10/13* (2023.01)
  *H10N 10/17* (2023.01)
  *A61B 18/00* (2006.01)

(52) U.S. Cl.
  CPC ..... *F28D 15/0233* (2013.01); *F28D 15/0275* (2013.01); *F28D 15/046* (2013.01); *H01L 23/38* (2013.01); *H10N 10/00* (2023.02); *H10N 10/13* (2023.02); *H10N 10/17* (2023.02); *A61B 2018/00452* (2013.01); *A61F 2007/0075* (2013.01)

(58) Field of Classification Search
  CPC ......... A61F 2007/0075; F28D 15/0233; F28D 15/0275; F28D 15/046; H01L 23/38; H01L 35/00; H01L 35/30; H01L 35/32
  See application file for complete search history.

(56) References Cited

U.S. PATENT DOCUMENTS

| | | | | |
|---|---|---|---|---|
| 6,338,251 B1 * | 1/2002 | Ghoshal | ............... | H10N 10/852 62/3.4 |
| 7,926,293 B2 * | 4/2011 | Bell | ................. | F02G 1/043 62/3.2 |
| 8,058,724 B2 * | 11/2011 | Refai-Ahmed | ......... | H01L 23/38 257/706 |
| 8,621,875 B2 * | 1/2014 | Parish | ................ | H05K 7/20336 29/890.032 |
| 9,504,189 B1 * | 11/2016 | Campbell | .......... | H05K 7/20127 |
| 10,217,692 B2 * | 2/2019 | Haj-Hariri | .......... | H01L 25/0657 |
| 2003/0037907 A1 * | 2/2003 | Lee | .......................... | F25B 21/02 165/104.19 |
| 2003/0089486 A1 * | 5/2003 | Parish | .................... | F28D 1/0246 165/104.33 |
| 2009/0140417 A1 * | 6/2009 | Refai-Ahmed | ....... | H01L 23/427 257/707 |
| 2011/0023927 A1 * | 2/2011 | Hsu | ........................ | H10N 10/13 136/205 |
| 2012/0111028 A1 * | 5/2012 | Campbell | ............... | F25B 21/02 62/3.7 |
| 2012/0290023 A1 * | 11/2012 | Boyden | .................. | A61F 7/007 607/3 |
| 2014/0026637 A1 * | 1/2014 | Blanc | ................. | G01N 30/6095 73/23.39 |
| 2014/0334106 A1 * | 11/2014 | Prest | ..................... | F28F 21/087 165/185 |
| 2015/0083180 A1 * | 3/2015 | Lang | ..................... | H10N 10/13 136/207 |
| 2015/0198380 A1 * | 7/2015 | Haj-Hariri | ............ | F28F 13/187 62/3.2 |
| 2016/0035957 A1 * | 2/2016 | Casey | ..................... | F01N 5/025 136/230 |
| 2021/0085518 A1 * | 3/2021 | Lessing | ................... | A61F 7/007 |

OTHER PUBLICATIONS

PCT Invitation to pay additional fees for PCT Application No. PCT/US2020/043151, filed Jul. 22, 2020, 15 pages.

\* cited by examiner

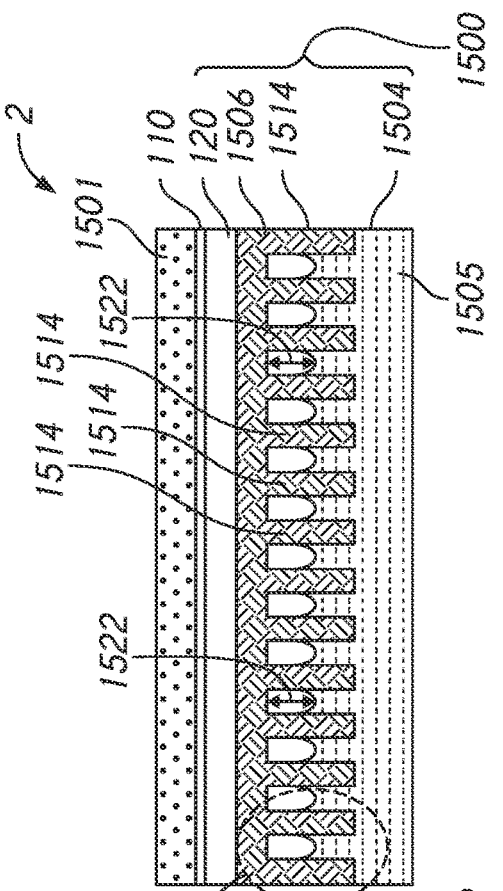
FIG. 15A
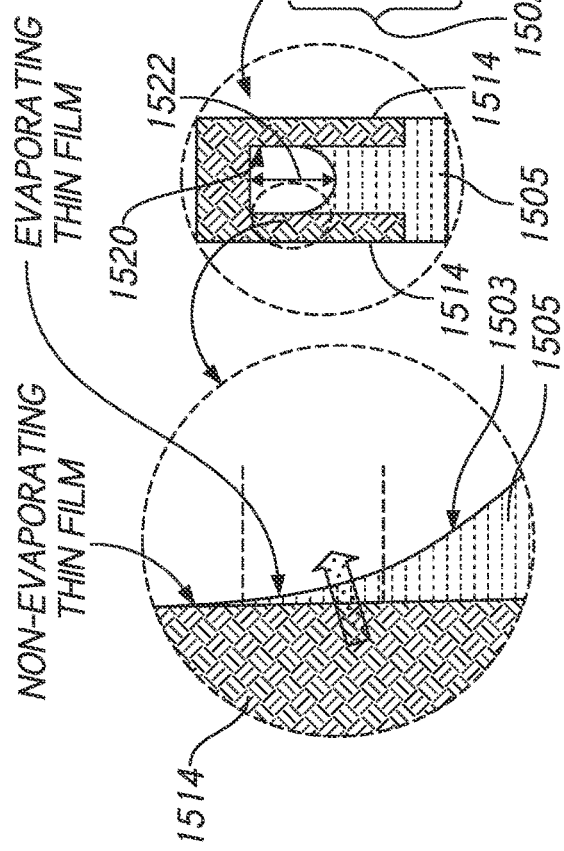
FIG. 15B
FIG. 15C
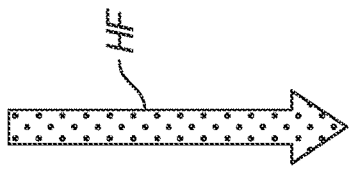
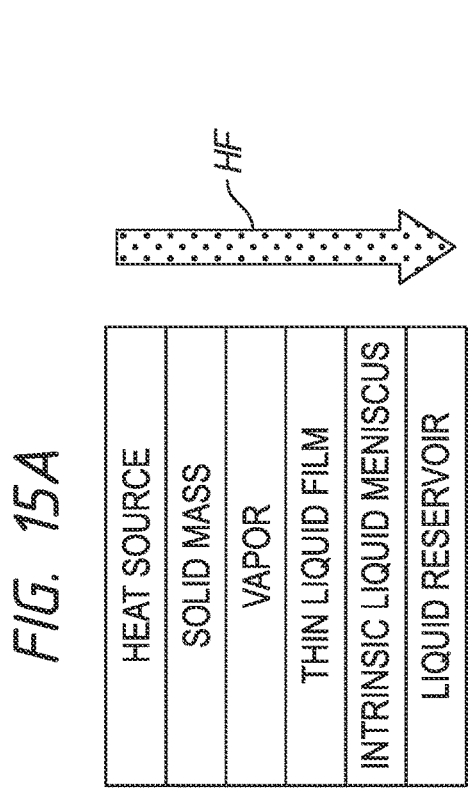
FIG. 15E
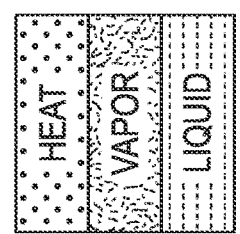
FIG. 15D

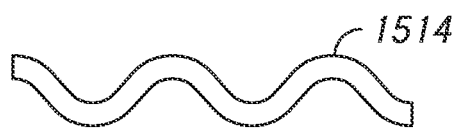
FIG. 19A
FIG. 19B
FIG. 19C
FIG. 19D
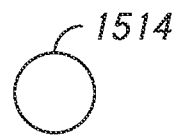 
FIG. 20A   FIG. 20B
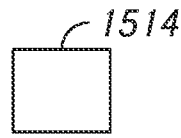 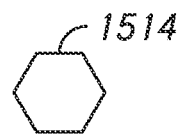 
FIG. 20C   FIG. 20D   FIG. 20E

THERMAL MANAGEMENT DEVICE AND SYSTEM

CROSS REFERENCE TO RELATED APPLICATIONS

This application claims priority to and the benefit of U.S. Provisional Application 62/877,122, filed 22 Jul. 2019, and U.S. Provisional Application 62/954,759, filed 30 Dec. 2019. which are both incorporated herein by reference in their entirety.

FIELD OF THE INVENTION

The present technology relates to a device for cooling and heating a target material, such as tissue, a heat source, or another type of substrate.

BACKGROUND OF THE INVENTION

Many electronic devices, medical and aesthetic devices, and high heat flux systems use thermal management devices to operate within acceptable temperature ranges and/or achieve desired outcomes. In many applications, the thermal management systems extract and dissipate heat fluxes to maintain temperatures within acceptable ranges for the target material.

One type of thermal management system is a two-phase heat transfer device in which a working fluid transitions from liquid phase to vapor phase to extract heat from the target material. In such two-phase heat transfer devices, high heat transfer rates can be obtained because of the latent heat of evaporation of the working fluid. Two-phase heat transfer devices have been disclosed for use in cooling semiconductor devices (e.g., controllers, memory devices, etc.), computer systems (e.g., servers), medical devices used in tissue, hair, adipose and pain management treatments, and wearable cooling devices.

Semiconductor devices, such as controllers, memory devices and light emitting diodes, often need to dissipate heat for maintaining acceptable operating temperatures. As the speeds and capacities of these devices increase, the heat fluxes increase requiring more heat to be dissipated to maintain acceptable operating temperatures. However, in many applications the heat fluxes of high-performance semiconductor devices and computing systems are too high for the heat transfer systems, and as a result the speeds and capacities of the systems are limited. This problem is only exacerbated as mobile phones, tablets and laptop computers have smaller sizes and/or higher performance. Similarly, large-scale server applications in which many servers are housed in a common location (e.g., data storage, web systems and computing centers) have significant heat dissipation requirements. Although two-phase heat transfer systems have high heat transfer rates, they are often too large and cumbersome for use with semiconductor devices and high-performance computing systems.

Several medical and aesthetic procedures heat and/or cool tissue to reduce pain, manage swelling, reduce adipose tissue for body sculpting, remove hair, tighten skin (e.g., remove wrinkles), remove lesions, alter sebaceous glands, and other heat treatments. The tissue can be heated using radiofrequency energy, laser energy, ultrasonic energy, X-ray radiation beams, and other energy modalities. For example, hyperthermia methods use heat to damage cancer cells for treating cancer (see, e.g., U.S. Pat. No. 9,802,063). Other medical applications treat conditions by cooling tissue, such as cryogenic tissue remodeling (see, e.g., U.S. Pat. No. 10,363,080).

One challenge of heating and/or cooling tissue is accurately controlling the temperature of the target tissue because different types of tissue react differently to heat and cooling, and different depths within the tissue can react differently because blood flow can significantly impact the temperature of the target site. Another challenge is unwanted heating and cooling of adjacent tissues, such as nerves or epidermal tissue. Although two-phase heat transfer systems have been used for thermal management of target tissue in medical and aesthetic applications, conventional systems often have slow response times and therefore do not provide precise thermal modulation of a target tissue. Additionally, many medical and aesthetic applications use bulky heat transfer devices that are uncomfortable for the patient and impractical for home use or treating certain body parts (e.g., the face, knees, shoulders, ankles, wrists, etc.).

Devices for cooling a target material or substrate are known. See for example U.S. Pat. No. 10,217,692. Methods for cooling skin in conjunction with skin treatment are also known. See Nelson J S, Majaron B, Kelly K M., *Active Skin Cooling in Conjunction with Laser Dermatologic Surgery*, Semin Cutan Med Surg. 2000; 19:253-66 and Das et al., J. Cutan. Aesthet. Surg. 2016; 9(4): 215-219.

BRIEF DESCRIPTION OF THE DRAWINGS

FIG. 15A schematically illustrates an embodiment a heat transfer unit for use with thermal management systems of the present technology. FIG. 15B is an enlarged partial view of a single passage in the device of FIG. 15A. FIG. 15C is an enlarged partial view of the thin film region as part of the meniscus as shown in FIG. 15B where the bulk of evaporation and heat transfer take place. FIG. 15D is a block diagram of the general arrangement of the device of FIG. 15A. FIG. 15E schematically illustrates the general circuit of the heat flow traveling within an embodiment of the heat transfer device.

FIGS. 19A-19D schematically illustrate various embodiments of microfeatures in the form of a wall or panel having a variety of contours or shapes, and which may have multiple curves or angles. Some shapes may include multiple contours (FIG. 19A); multiple angles (FIG. 19B); single curve (FIG. 19C); and straight alignment (FIG. 19D).

FIGS. 20A-20E schematically illustrate various embodiments of microfeatures in the shape of a rod, pin, or post having different cross-sections as follows: circular, oval, rectangular (or square), hexagonal, and triangular, respectively. The cross section may be of any polygonal cross section.

Figure 1A:
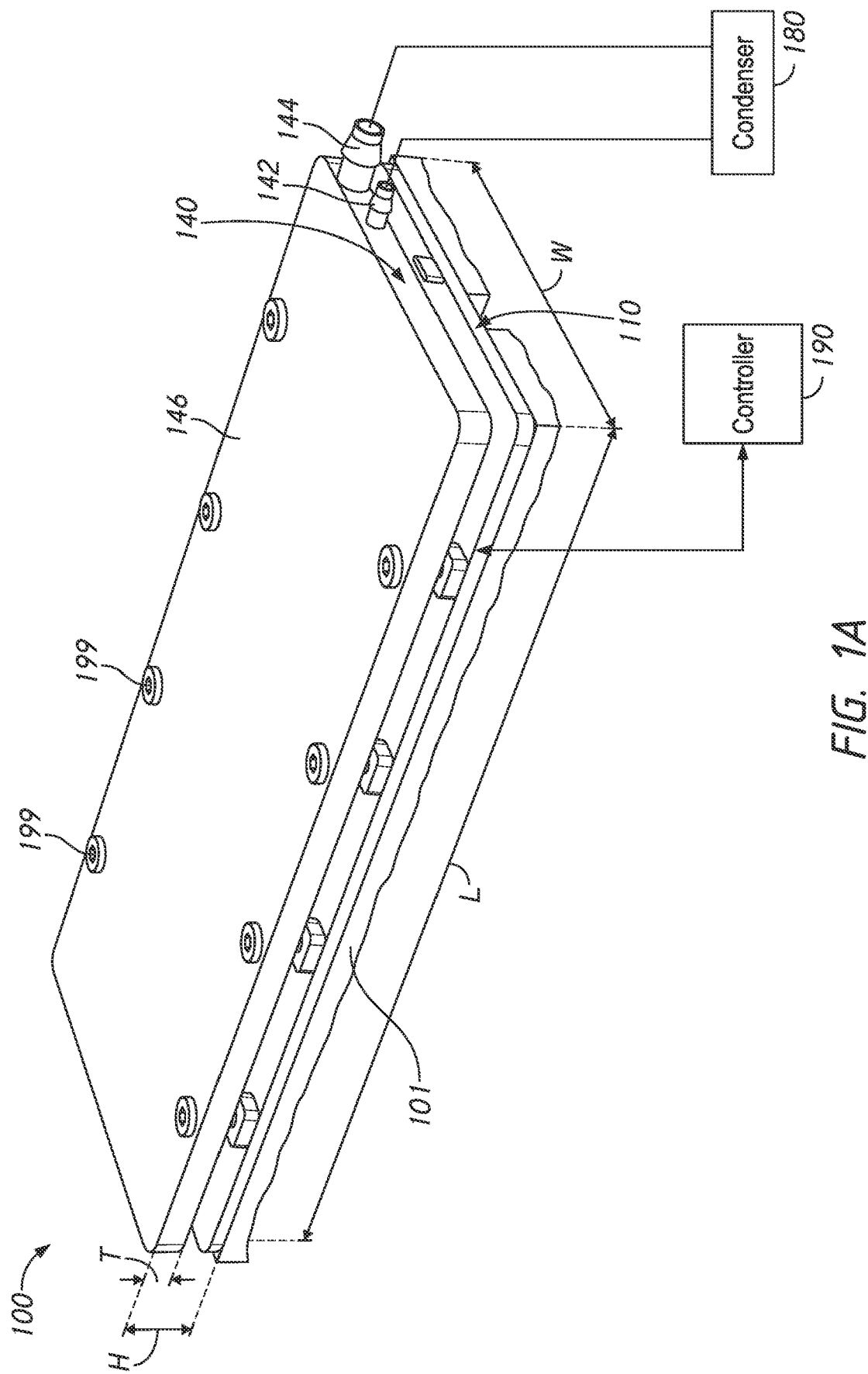
FIGS. 1A-1C are isometric views of a thermal management system for cooling and/or heating a target material in accordance with embodiments of the present technology.

The figures should be understood to present illustrations of embodiments of the invention and/or principles involved. As would be apparent to one of skill in the art having knowledge of the present technology, other devices, methods, and particularly equipment used in heat transfer devices, temperature sensors, microfeatures, and/or thermoelectric components, will have configurations and components determined, in part, by their specific use. Like reference numerals refer to corresponding parts throughout the several views of the drawings.

DETAILED DESCRIPTION OF EMBODIMENTS

Aspects of the present technology are directed to systems for regulating the temperature of a target material (e.g., substrate), such as mammalian tissue (e.g., human tissue) and electronic devices. It will be appreciated that devices in accordance with the present technology can control the temperature of the surface of the substrate and/or regulate the temperature at a depth within the substrate. According to one aspect, the systems for regulating the temperature of a substrate include a heat-transfer unit operatively connected to a thermoelectric component for heating or cooling a substrate surface.

The present technology can be used in high heat flux applications, such as treatment of mammalian tissue (used interchangeably with human tissue throughout), computer chips, semiconductor devices, integrated circuit devices, laser systems (e.g., high power laser systems with high heat fluxes that need to be dissipated to generate desired output beams and/or power), skin of hypersonic flying objects, parabolic solar collectors, high performance computing systems, radio frequency (RF) systems, photovoltaic or concentrated photovoltaic systems, hypersonic avionic applications, turbine blades, or any other surfaces or volumetric heat dissipation devices or systems. The thermal management systems of the present technology are particularly efficacious for cooling the skin of a patient with respect to treatments using laser light or needles. For example, cooling the epidermis and dermis to reduce pain when the tissue is treated with a laser light or a needle. It should be appreciated that various embodiments of the present technology device may be applied to and/or be utilized with a wide range of applications as desired, needed or required.

Figure 1B:
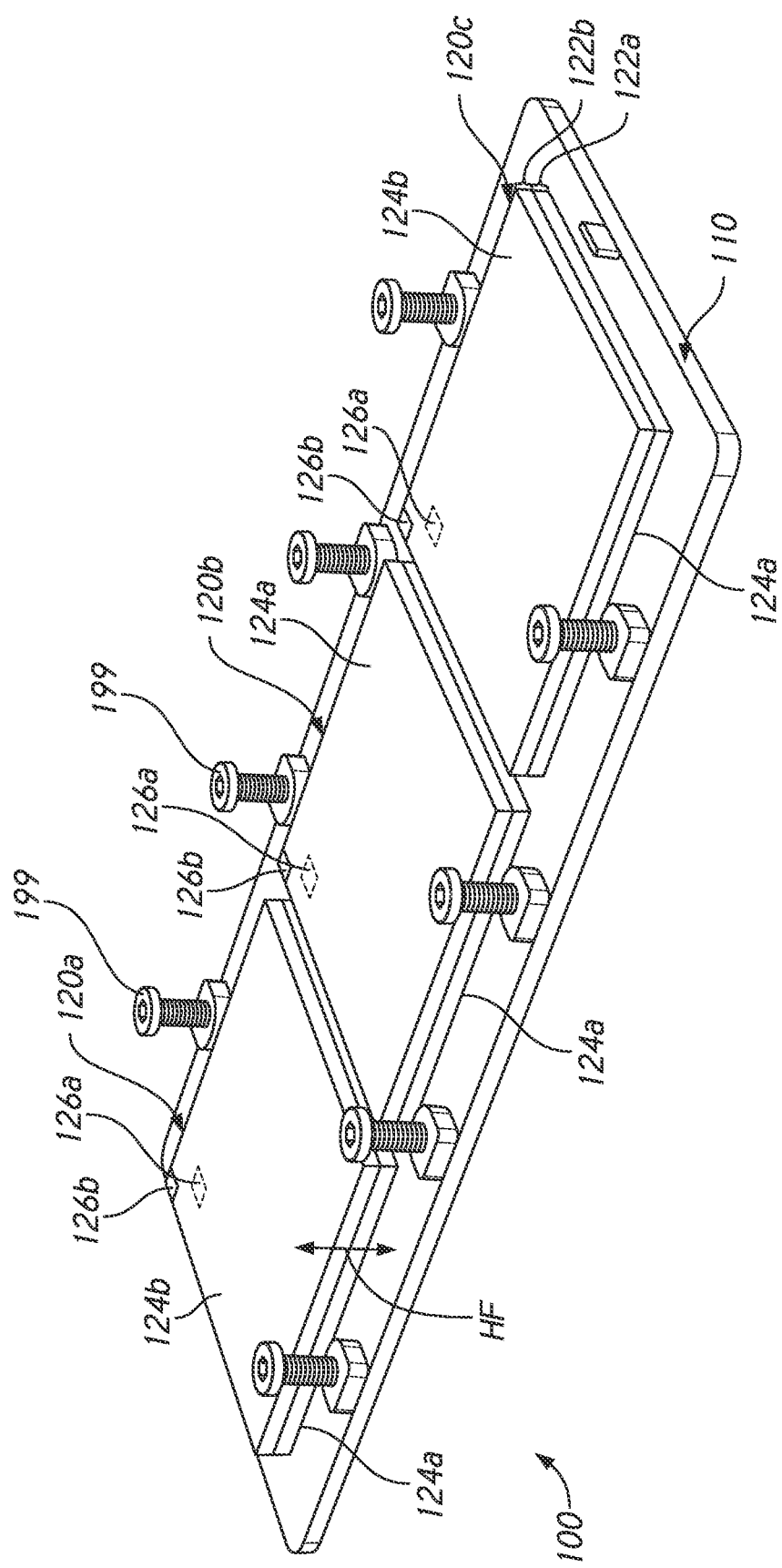
Figure 1C:
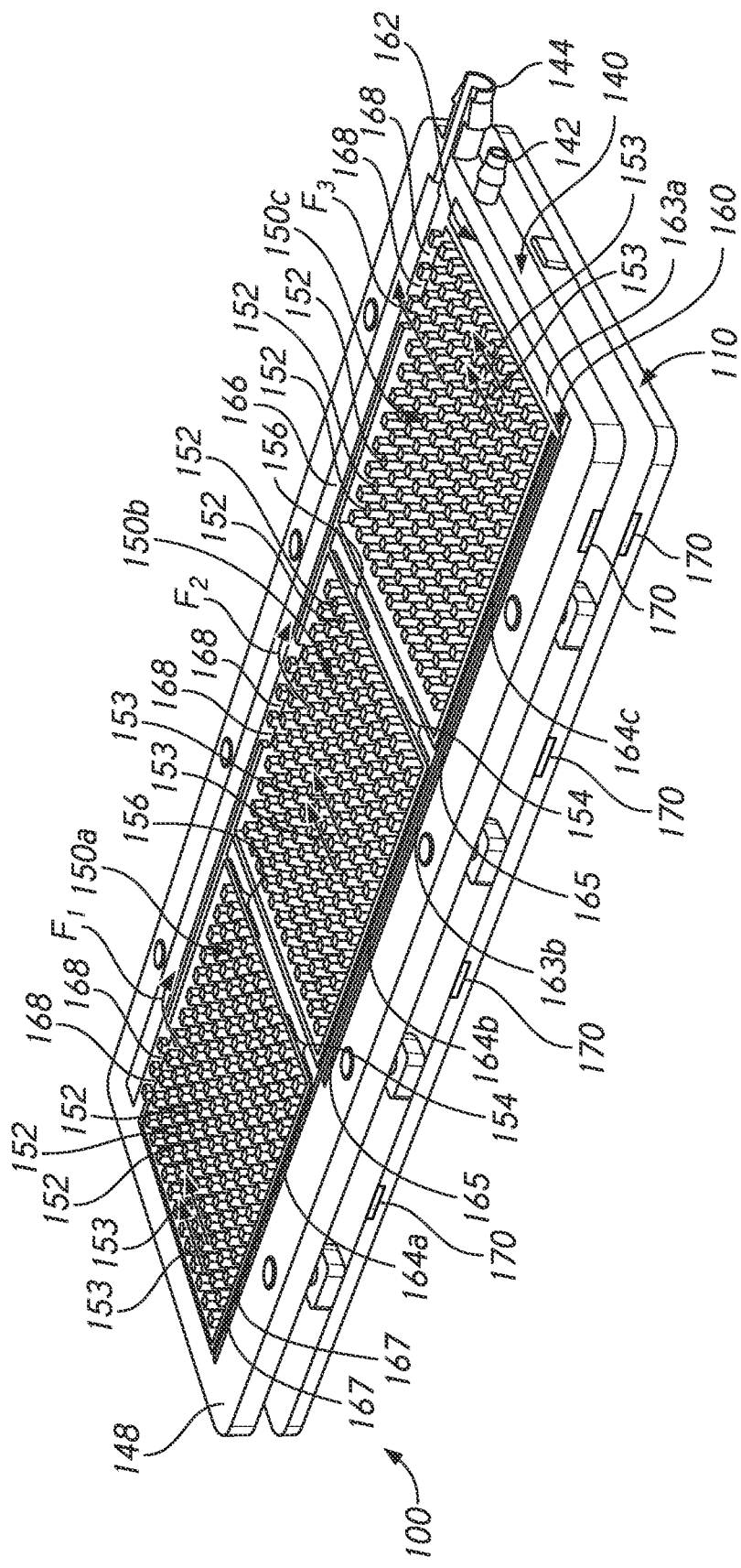

FIGS. 1A-1C are isometric views of a thermal management system 100 for cooling and/or heating a target material 101 in accordance with embodiments of the present technology. The thermal management system 100 can accurately and quickly control the temperature at the surface of the target material 101 and/or at a depth within the target material 101. As described in more detail below, the target material 101 can be mammalian tissue (e.g., skin, adipose tissue, hair, lesions, cancerous cells, etc., of a human), semiconductor devices (e.g., controllers, memory devices, light emitting diodes, servers, high-performance computers, etc.), and other applications with high heat fluxes (e.g., lasers).

Referring to FIGS. 1A and 1B together, the thermal management system 100 can include an optional contact member 110, at least one thermoelectric component (TEC) 120a (FIG. 1B) thermally coupled to the contact member 110, and a two-phase heat transfer unit 140 thermally coupled to the TEC 120a. FIG. 1A shows the thermal management system 100 fully assembled, and FIG. 1B shows the thermal management system 100 without the heat transfer unit 140. The thermal management system 100 can have several TECs, for example first, second and third TECs 120a-c, respectively (referred to collectively throughout as TECs 120). The thermal management system 100 can have any number of TECs 120 and is not limited to having three TECs 120. The thermal management system 100 can also include a condenser 180 operatively coupled to the heat transfer unit 140 to form a closed system and a controller 190 operatively coupled to the TECs 120, the heat transfer unit 140 and/or the condenser 180. In operation, a working fluid contained in the heat transfer unit 140 and the condenser 180 changes from a liquid phase to a vapor phase in the heat transfer unit 140 to cool one side of the TECs 120, and the controller 190 adjusts an electrical current through the TECs 120 and/or the flow of working fluid through the heat transfer unit 140 to manage the temperature of the contact member 110 and thus the target material 101.

In the assembled state shown in FIG. 1A, the contact member 110, TECs 120 and heat transfer unit 140 can be held together by bolts 199. The TECs 120 can further be attached to the contact member 110 by a first thermal interface material and to the underside of the heat transfer unit 140 by a second thermal interface material. The heat management system 100 can have any suitable length L and width W for covering a desired area of the target material 101. The heat management system 100 can have a low-profile with a height H of 2 mm-25 mm, including 5 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm and 25 mm. The heat transfer unit 140 itself can have a thickness T of 2 mm-20 mm, including 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm and 19 mm. For example, when the heat transfer unit 140 is directly integrated into the second portion 122b of a TEC 120, the overall height H can be 2-3 mm. The height H and thickness T can be measured in a direction of heat flow through the TECs 120 (arrow HF in FIG. 1B).

The TECs 120 each have a first portion 122a and a second portion 122b. The first and second portions 122a-b are understood relative to positioning with respect to the surface of the target material 101, in which the first portion 122a is thermally coupled to the target material 101 and the second portion 122b is opposite the first portion 122a. The first portion 122a of the TECs 120 can include a first outer surface 124a (i.e., the lower surface in FIG. 1B) of the TECs 120 and a portion of the TECs 120 that extends inwardly a distance from the first outer surface 124a. The second portion 124b of the TECs 120 can include a second outer surface 124b (i.e., the upper surface in FIG. 1B) of the TECs 120 and a portion of the TECs 120 that extends inwardly a distance into the interior of the TECs 120 from the second outer surface 124b. It is to be understood that the TECs 120 may have a midpoint equidistant within the interior of the TECs 120 between the first and second outer surfaces 124a-b. The first and second portions 122a-b of the TECs 120 are electrically connected to a power source. For example, the TECs 120 may each include a first electrical contact 126a (shown in phantom line) at the first portion 122a and a second electrical contact 126b at the second portion 122b through which an electrical current can flow in either direction.

The first portion 122a of the TECs 120 is intended to be thermally coupled to a surface of the target material 101 either directly or indirectly. For example, the first portion 122a of the TECs 120 can be indirectly thermally coupled to the target material 101 via the contact member 110, which can be a plate, panel, film or fabric made from a material with a high thermal conductivity (e.g., an aluminum plate or panel). The heat management system 100 may include two or more such plates or panels or films contacting each other as desired. The second portion 122b of the TECs 120 is thermally coupled to the heat transfer unit 140 either directly or indirectly. For example, the second portion 122b of the TECs 120 is directly coupled to the heat transfer unit 140 by a thermal interface material having a high thermal conductivity. The heat transfer unit 140 can remove heat from the target material 101 as well as heat generated by the TECs 120.

Without wishing to be bound by scientific theory, heat flow is induced in a certain direction in the TECs 120 by electric current. According to one nonlimiting aspect, when the device for regulating the temperature of the target material 101 is activated and electricity flows in a direction from the second portion 122b of the TECs 120 to the first portion 122a of the TECs 120, the first portion 122a cools relative to its ambient or starting temperature, i.e., the temperature of the first portion 122a decreases thereby removing heat from the target material 101. The second portion 122b accordingly heats or generates heat relative to its ambient or starting temperature. It is to be understood that embodiments are contemplated where the direction of heat flow may be in the same direction as electric current flow or in the opposite direction of the electric current flow.

The heat-transfer unit 140 may be fixed to the second portions 122b of the TECs 120 or it may be selectively detached from the second portions 122b of the TECs 120 to break the thermal contact with the TECs 120 using piezoelectric drivers, electric motors or other electromechanical devices. Similarly, the TECs 120 may be selectively detached from (i.e., separated from) the target material 101 and or the contact member 110 to break thermal contact therewith using piezoelectric drivers, electric motors or other electromechanical drivers. Such devices may be known as thermal switches insofar as heat is used to cause the switch to alter shape creating physical separation between two surfaces (e.g., an air gap), such as the two-phase heat-transfer unit 140 and the TECs 120 or the TECs 120 and the contact member 110. According to one aspect, it may be desirable to disconnect the heat transfer unit 140 from the TECs 120 or to disconnect the TECs 120 from the contact member 110 for a given period of time.

Referring to FIGS. 1A and 1B, the heat transfer unit 140 covers the second portions 122b of the TECs 120. The heat transfer unit 140 has an inlet 142, an outlet 144, and a cover 146. In operation, a working fluid flows in a liquid state or a mixed liquid-vapor state (e.g., high pressure single-stage closed cooling systems) from the condenser 180 to the inlet 142, and at least a portion of the working fluid flows in a vapor state from the outlet 144 back to the condenser 180. The cover 146 retains the working fluid within the heat transfer unit 140 and along with other components defines the flow characteristics of the working fluid through the heat transfer unit 140.

FIG. 1C illustrates embodiments of the internal structure of the heat transfer unit 140 with the cover 146 (FIG. 1B) removed. The heat transfer unit 140 can include a base 148 to which the cover 146 is connected, at least one phase-transition chamber 150 (three phase-transition chambers 150a-c shown and identified individually), and a duct system 160 fluidically coupled to the inlet 142, the outlet 144, and the phase-transition chambers 150a-c. The phase-transition chambers 150a-c are at least generally aligned with a corresponding one of the TECs 120a-c, respectively. For example, each of the phase-transition chambers 150a-c can be directly superimposed above a corresponding one of the TECs 120a-c, respectively. The heat transfer unit 140 can have a single inlet 142 and single outlet 144 to service all of the phase-transition chambers 150a-c as shown, or the heat transfer unit 140 can have several inlets 142 and outlets 144. For example, the heat transfer unit 140 can have one or more inlets 142 and/or outlets 144 for each phase-transition chamber 150a-c or for any other purpose to provide the desired flow of working fluid through the heat transfer unit 140.

The phase-transition chambers 150a-c include microfeatures 152, an inlet region 154, and an outlet region 156. The microfeatures 152 shown in FIG. 1C are pins or posts arranged in a grid-type array, but in other embodiments the microfeatures can be elongated walls. The microfeatures 152 define microchannels 153 through which the working fluid flows through the phase-transition chambers 150a-c.

The microfeatures 152, whether pins or elongated walls, can have different arrangements other than a being arranged in straight, uniform rows as described below with reference to FIGS. 18A, 18C and 18D. The microfeatures 152 can be spaced apart from each other by a uniform distance, or the distance between microfeatures 152 can vary in relation to the positions and flow characteristics of the inlet region 154 and the outlet region 156. For example, the microfeatures 152 can be spaced apart from each other by a first distance in the inlet region 154 and a second distance in the outlet region 156. The second distance can be greater than the first distance to accommodate the flow of vapor through the outlet region 156, or the second distance can be less than the first distance to accommodate the capillary force exerted against the liquid phase of the working fluid flowing through the phase-transition chambers 150a-c. Additionally, the spacing between microfeatures 152 in one of the phase-transition chambers 150 may be the same as or different than the spacing between microfeatures 152 in one or more of the other phase-transition chambers 150a-c.

The spacing between the microfeatures 152 can be selected to (a) generate capillary forces in the working fluid that drives the working fluid from the inlet region 154 of the phase-transition chamber to the outlet region 156, (b) accommodates the flow of vapor through the inlet and outlet regions 154 and 156 of the phase-transition chambers 150a-c, and/or (c) forms a desired meniscus between adjacent microfeatures 152 to enhance the evaporation zone along each microfeature 152 to enhance heat transfer. In some embodiments, the spacing between microfeatures is selected such that the capillary forces induced in the working fluid enable the heat transfer unit 140 to operate omnidirectionally (e.g., inverted so the heat transfer unit 140 is below the TECs or at an angle relative to horizontal). The spacing between microfeatures 152, for example, can be a range having a low end of 50 nm, 100 nm, 200 nm, 500 nm, 1 µm, 2 µm, 5 µm or 10 µm and a high end of 25 µm, 50 µm, 100 µm, 150 µm, 200 µm, 250 µm, 300 µm, 350 µm, 400 µm, 450 µm, 500 µm, 600 µm, 700 µm, 800 µm, 900 µm or 1,000 µm. In specific examples, the spacing between microfeatures can be 100 nm-1,000 µm, 100 nm-500 µm, 100 nm-400 µm, 100 nm-300 µm, 100 nm-250 µm, 100 nm-200 µm, 50 nm-150 µm, 50 nm-100 µm, 50 nm-50 µm, 50 nm-25 µm or 50 nm to 10 µm.

The duct system 160 includes a primary duct 162 having a first channel 163a fluidically coupled to the inlet 140 and a second channel 163b extending from the first channel 163a along the phase-transitions chambers 150a-c. The duct system 160 further includes manifold ducts 164a-c (referred to collectively as "manifold ducts 164") and an exit duct 166. The manifold ducts 164 are fluidically coupled to the second channel 163b of the primary duct 162 at junctions 165, and the exit duct 166 is fluidically coupled to the outlet 144. The phase-transition chambers 150a-c can further include inlet ports 167 and outlet ports 168. The inlet ports fluidically couple the respective manifold ducts 164 to the inlet regions 154 of the phase-transition chambers 150a-c, and the outlet ports 168 fluidically couple the outlet regions of the phase-transition chambers 150a-c to the exit duct 166. The inlets ports 167 can be small passages having a uniform arrangement along the respective manifold ducts 164a-c (only shown along manifold duct 164a for convenience, but also present along manifold ducts 164b and 164c). The outlet ports 168 can be larger passages at the end of the outlet regions 156 of the phase-transition chambers 150a-c through which vapor passes into exit duct 166. The outlet ports 168 can be arranged differently for different phase-transition chambers 150a-c to provide the desired flow of vapor along the exit duct 166. For example, in the illustrated embodiment the outlet ports 168 of the first phase-transition chamber 150a can be at an upstream portion of the exit duct 166 relative to the first phase-transition chamber 150a, the outlet ports 168 of the second phase-transition chamber 150b can be at a middle-stream portion of the exit duct 166 relative to the second phase-transition chamber 150b, and the outlet ports 168 of the third phase-transition chamber 150c can be a downstream region of the exit duct 166 relative to the third phase-transition chamber 150c.

In operation, the working fluid flows from the condenser 180 (FIG. 1A) to the inlet 140 in the liquid phase, and then the working fluid flows through the primary duct 162 and the manifold ducts 164a-c to the inlet ports 167. The manifold ducts 164a-c and the junctions 165 can be configured to provide a uniform distribution (e.g., uniform flow) of the working fluid to the inlet ports 167 along the phase-transition chambers 150a-c. The working fluid then flows through the inlet ports 167, the microchannels 153 of the individual phase-transitions chambers 150a-c, and the outlet ports 168 in flows $F_1$, $F_2$ and $F_3$. As the working fluid flows through the phase-transition chambers 150a-c, it transitions from liquid phase to vapor phase in the evaporation regions along the microfeatures 152.

The base 148 of the heat-transfer unit 140 can be made from aluminum, copper, silicon, or other materials with high thermal conductivity. The phase-transition chambers 150a-c, microfeatures 152, and duct system 160 can be formed by masking and etching the base as known in semiconductor manufacturing, waterjet cutting, laser ablation, or by three-dimensional printing. Additionally, the surface of the base 148 in the phase-transition chambers 150a-c can be texturized, such as by sandblasting.

The heat-transfer unit 140 removes heat from the second portions 122b of the TECs 120 whether generated by electricity flowing through the TECs 120 or from the target material 101 itself (e.g., when the target material is an active heat source such as a controller, memory device, laser, etc.). Since the TECs 120 may generate a high heat flux, the heat-transfer unit 140 should remove (e.g., dissipate) at least a portion of the high heat flux. In this manner, the TECs 120 may continually cool the target material, i.e. continually remove heat from the target material. The heat-transfer unit 140 can prevent or otherwise limit the TECs 120 from overheating during use. If the heat-transfer unit 140 were not used, then heat generated at the second portions 122b of the TECs 120 would gradually increase thereby decreasing the ability of the TECs 120 to cool the target material. The heat-transfer unit 140 is selected such that it has the ability to remove sufficient heat generated at the second portion 122b of the TECs 120 to allow the first portions 122a of the TECs 120 to cool the target material, as desired.

The TECs 120 may maintain the target material 101 at a constant temperature or may lower and/or raise the temperature of the target material 101 according to a desired temperature profile. One or more auxiliary heating or cooling elements in addition to the TECs 120 may be positioned adjacent the target material 101 so as to provide auxiliary heating or cooling of the target material 101. For example, the TECs 120 may be used to cool the target material surface and a separate resistive heating element may be used to heat the target material surface. Additionally, the TECs 120 may be used to heat the target material surface and an auxiliary cooling element may be used to cool the target material surface.

According to one aspect, the TECs 120 may be used to heat or otherwise increase the temperature of the target material 101. For example, when the thermal management system 100 is activated and electricity flows through the TECs 120 such that the first portion 122a of the TECs 120 heats or generates heat relative to its ambient or starting temperature, i.e., the temperature of the first portion 122a of the TECs increases while the second portion 122b of the TECs 120 cools relative to its ambient or starting temperature. In this manner, the temperature of the target material may be increased relative to its ambient temperature. It is to be understood that embodiments of semiconductors materials or arrangements of semiconductor materials of the TECs 120 can be configured such that the direction of heat flow may be in the same direction as electric current flow or in the opposite direction of the electric current flow. When used in this operating mode to heat a target material, the heat-transfer unit 140 may be deactivated or physically separated from the TECs 120 such that the heat-transfer unit 140 does not remove heat from the cold side of the TECs 120. However, the heat-transfer unit 140 and the TECs 120 may alternatively be operated concurrently to achieve a desired temperature profile of the target material even when the TECs 120 are warmer at the first portion 122a than at the second portion 122b, including lowering the temperature from an ambient or starting temperature and then raising the temperature.

The TECs 120 may lower or raise the temperature of the target material according to a desired temperature profile depending upon the direction of flow of the electric current through the TECs 120. According to one aspect of the present technology, the TECs may be used to decrease and/or increase the temperature of the first portions 122a of the TECs 120 and therefore the target material according to a desired temperature profile using directional flow of electricity through the TECs and in combination with the heat-transfer unit 140 to remove heat from the TECs 120 when desired. By changing the direction of flow of electricity, the first portions 122a of the TECs 120 may rapidly and precisely cool or heat and thereby rapidly and precisely cool or heat the target material 101 according to a desired temperature profile over a desired period of time.

When in cooling mode, the heat-transfer unit 140 removes heat generated by the TECs 120 that would otherwise impact the ability of the TECs 120 to cool the target material in a desired manner. For example, using a first directional flow of electricity, the TECs 120 in combination with the heat-transfer unit 140 may cool the target material 101 from an initial ambient temperature $Temp_1$ (which may be the temperature of tissue of a patient, i.e. 35° C.-37° C.) to a lower temperature $Temp_2$ (which may be 9° C. to −4° C. or −10° C. or −15° C. or −20° C.) over a time period $Time_1$ (which may be in the range of 0.1 to 5 seconds or 10 seconds or 20 seconds). Using a second directional flow of electricity opposite to the first directional flow of electricity, the TECs 120 may then heat the target material from $Temp_2$ (which may be 9° C. to −4° C. or −10° C. or −15° C. or −20° C.) to a higher temperature $Temp_3$ (which may be room temperature or the normal temperature of tissue of a patient) over a time period $Time_1$ (which may be in the range of 0.1 to 5 seconds). These ranges are examples and do not limit the scope and utility of the embodiments described herein. For example, additional temperature ranges are 15° C. to −10° C., 10° C. to −6° C., 10° C. to 0° C., 15° C. to −15° C., 10° C. to −10° C., or the like. For example, the time range may be between 0.05 to 20 seconds, 0.05 to 10 seconds, or 0.1 to 7 seconds and the like.

The directional flow of electricity may be altered from one direction to the other to repeatedly cool or heat the target material, or vice versa, depending upon the desired application or use. Since the heating and cooling of the TECs 120 is driven by direction of current flow, the temperature of the first portions 122a of the TECs 120 and accordingly temperature of the target material 101 thermally coupled to the TECs 120 may be altered quickly, i.e. on the order of a fraction of a second to a few seconds, and with high precision, i.e. on the order of 0.1° C. to 0.5° C., 1.0° C., 1.5° C. or 2.0° C. The low thermal inertia (e.g., low heat capacity or low volumetric heat capacity) of the heat-transfer unit 140 allows precise switching between cooling and heating modes in a range of 0.1 second to 5 seconds. The heat-transfer unit 140, though having a low profile of 0.7 mm-25 mm or 5 mm-15 mm, is capable of removing the high heat flux generated by the TECs 120 to cool the target material from its ambient temperature to a lower temperature, for example between 9° C. to −4° C. or −10° C. or −15° C. or −20° C., within a time period of 0.1 second to 5 seconds, such as 2-3 seconds. In some embodiments, the heat transfer unit 140 generally has a thickness T of 0.7 mm-1.0 mm.

The TECs 120 may be used together or operated independently to heat or cool the target material with a given surface area or volume. With each TEC 120 generating heat within a given surface area, the heat-transfer unit 140 is capable of removing the heat generated from the group of TECs 120. Each TEC 120 may have its own heat-transfer unit 140 or a single unitary heat-transfer unit 140 as shown in FIGS. 1A-1C may remove heat from all or a subset of the TECs 120. For example, the heat-transfer unit 140 may have a surface area greater than the combined surface area of the plurality of TECs 120. According to one aspect, the heat-transfer unit 140 and the TECs 120 may be arranged relative to one another and the target material 101 such that the surface of the target material (e.g., epidermis) may be cooled while allowing light or radiation energy or a mechanical treatment device to operate through or between the heat-transfer unit and TECs to heat deeper tissue to a desired treatment temperature that would otherwise be painful or damaging to the epidermis.

The TECs 120 can be attached to a flexible contact member 110, or subsets of one or more TECs can be attached to a rigid contact member 110 and the rigid contact members 110 are coupled together by hinges to flex between rigid contact members 110. In such embodiments, each TEC 120 or subset of TECs 120 can have an individual heat transfer unit 140 with one or more phase-transition chambers 150, and the individual heat transfer units 140 can be thermally and physically separated (disconnected) from each other to allow the thermal management system to flex between individual TECs 120 or subsets of TECs 120. This configuration is particularly useful in applications where the target material 101 is non-planar, such as many body parts (e.g., shoulders, knees, ankles, face, torso, buttocks, head, etc.).

The TECs 120 may be arranged in an array of rows and columns or in any desired pattern to achieve a desired objective. For example, a device as described herein may include from 2 to 200 TECs 120 arranged within the surface area of a thermally conductive contact member (e.g., a plate or film or support). Depending upon the number of TECs 120, the TECs 120 may be arranged in a square pattern, rectangular pattern, circular pattern or other pattern relative to a thermally conductive contact member depending upon the surface area of the target material 101 and/or the contour of the target material 101. According to one aspect, the TECs 120 may be positioned horizontally with respect to one another in the same plane. According to one aspect, TECs 120 may be positioned vertically with respect to one another such as by stacking TECs 120 one on top of another.

Each TEC 120 may be operated independently to achieve different heating or cooling of different locations of the target material 101, or all of the TECs 120 may be operated simultaneously to achieve uniform heating or cooling of the target material 101. Subsets of the TECs 120 may be operated independently to achieve different heating or cooling of different locations on the target material 101. Additionally, each TEC 120 or subsets of the TECs 120 can have separate heat transfer units 140, and the pairs of TECs 120 and heat transfer units 140 can be operated independently or collectively.

Devices for regulating the temperature of a target material surface as described herein including a heat-transfer unit 140 and the TECs 120 may also include one or more temperature sensors, heat flux sensors, and/or pressure sensors (identified collectively by reference number 170) operatively connected to the device to sense or detect temperature, heat flux or pressure at one or more locations along or within the device. Such temperature and pressure sensors provide feedback on the operation of the device for regulating the temperature of a target material surface and may assist in regulating the operation of the device to provide a desired temperature or temperature profile of the target material. Accordingly, the devices for regulating the temperature of a target material surface as described herein non invasively cool a target material, such as tissue, to a predetermined temperature. It is to be understood that the target material has a thickness and the cooling or heating of the target material using the device described herein may create a temperature profile as a function of depth of the target material. For example, the outer surface of the target material may have a temperature lower than the temperature of a treatment site within the target material. This results in a temperature profile of the target material. Once a desired temperature of the outer surface of the target material has been achieved or a desired temperature profile within the target material as a function of depth of the target material has been reached, the target material may then be subjected to processing or treatment at the predetermined temperature or temperature profile. In some embodiments, a temperature profile is generated as a function of time, location on the target material, and/or depth within the target material.

The contact member 110 can be one or more thermally conducting plates or surfaces or films that thermally interconnect the heat-transfer unit 140 to the TECs 120 and/or the TECs 120 to the target material 101. For purposes of further discussion, reference will be made to a thermally conductive contact member, which can be a thermally conductive plate, surface, braid, fabric or film. The heat-transfer unit 140 may have its own thermally conductive contact member, and the TECs 120 may have their own thermally conductive contact member. The thermally conductive contact member of the heat-transfer unit 140 may be affixed or otherwise attached to the TECs 120. A single thermally conductive contact member may be between the heat-transfer unit 140 and the TECs 120. A thermally conductive contact member may be positioned at the bottom of the TECs 120 or may be part of the bottom of the TECs 120 to provide a thermally connection between the TECs 120 and the target material 101. Thermally conductive contact members may have a thickness between 0.01 mm and 5 mm.

The thermally conductive contact members may have any suitable configuration, shape, design, thickness, etc., to contact a given surface. The thermally conductive contact members may be rigid or flexible. The thermally conductive contact members may be flat, curved, convex, concave, bowed, undulating, pitted, ridged, dimpled, rough, smooth or have any other surface geometry sufficient for a particular thermal management method. Thermally conductive contact members may be transparent or nontransparent. A thermally conductive contact member may include at least one or more thermally conductive materials known to those of skill in the art such as thermally-conducting silicon, diamond, copper, silicon carbide, graphite, silver, gold, platinum, copper, sapphire, graphene, or silicon oxide--as well as other materials as desired, needed or required.

Figure 2:
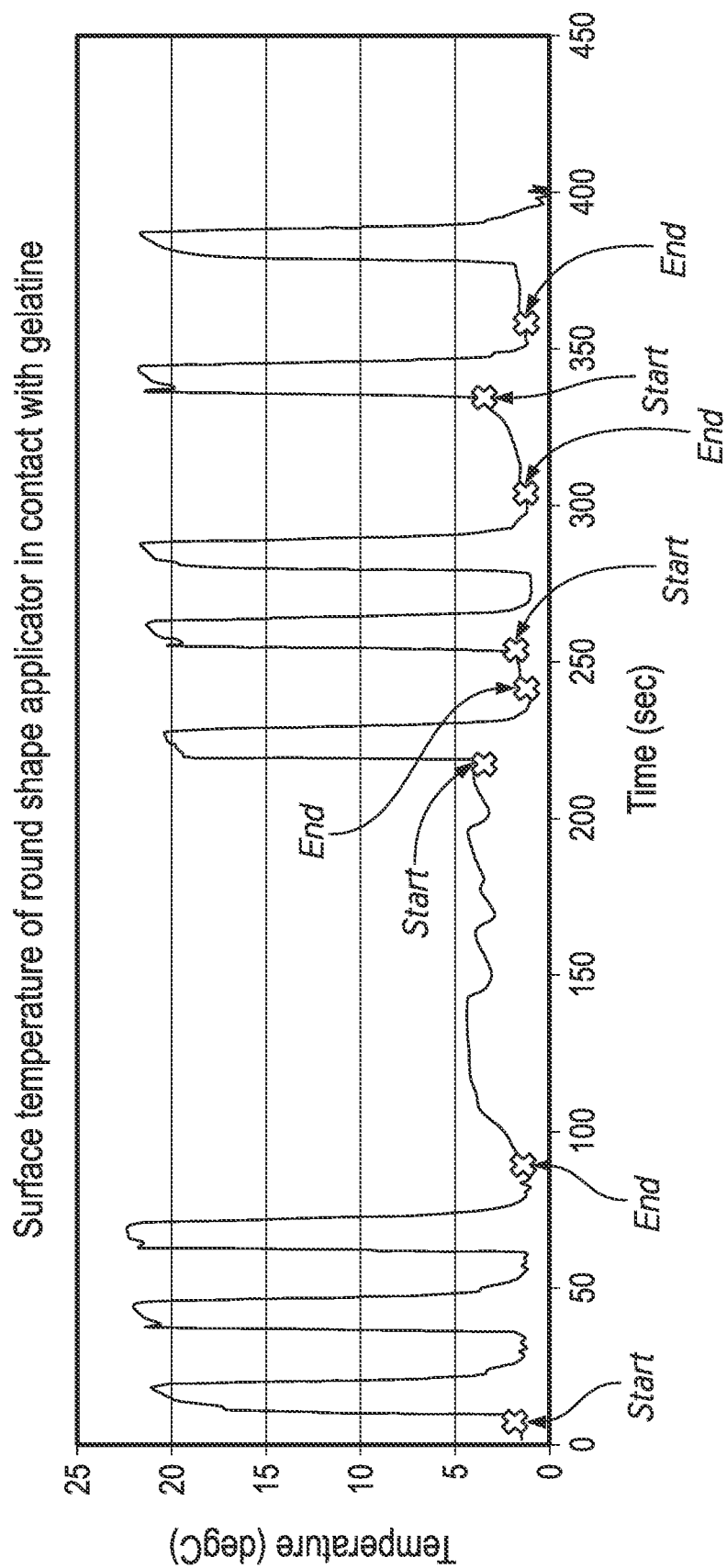
FIG. 2 is a graph of time and temperature of a surface of a target material simulating human tissue using a thermal management system in accordance with the present technology.
Figure 3:
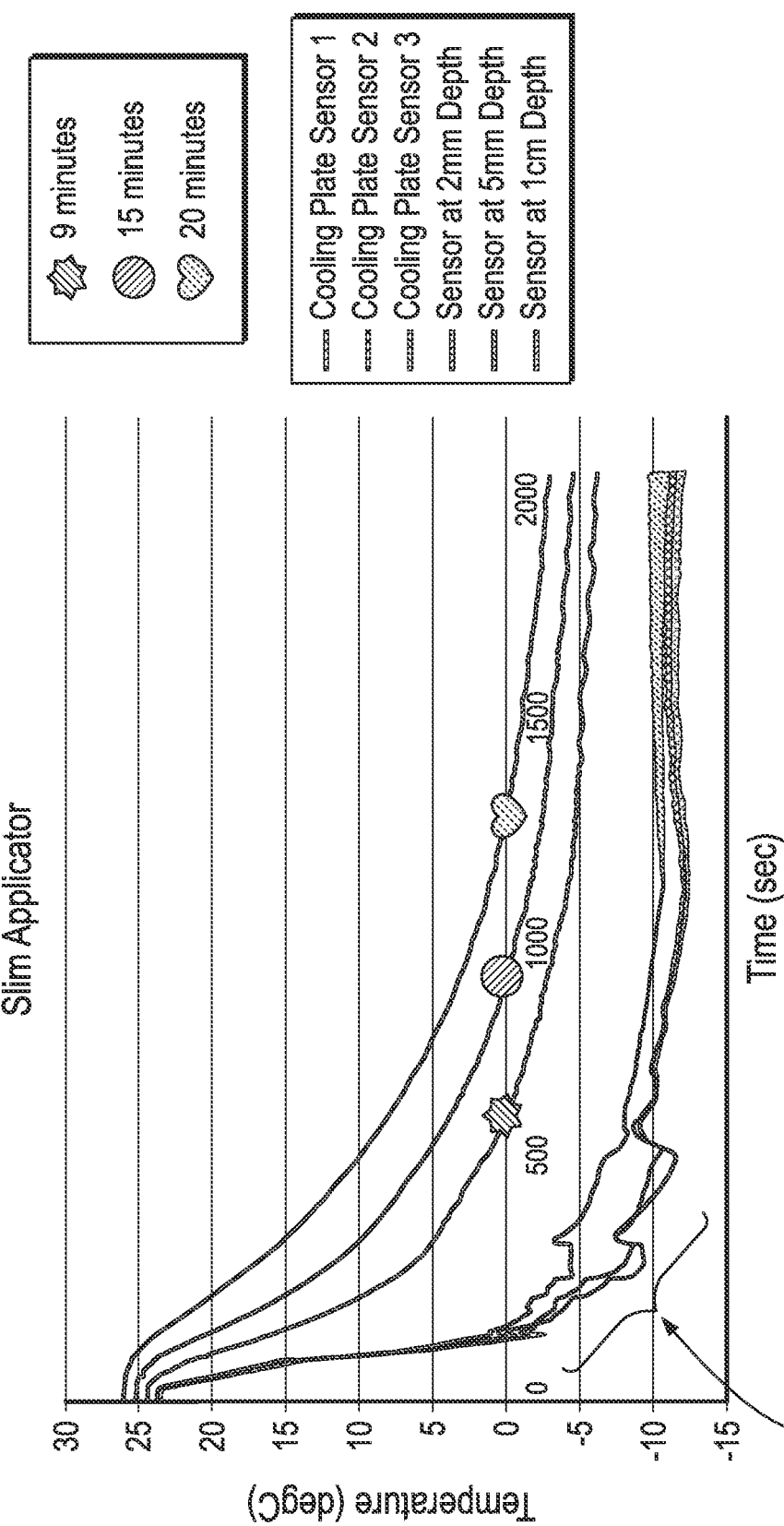
FIG. 3 is a graph of time and temperatures of a surface and within various depths of a target material simulating human tissue using a thermal management system in accordance with the present technology.

According to one aspect in which the target material is human tissue, a method cools and/or heats target tissue to predetermined temperatures in predetermined times to rapidly and precisely cool and heat the target tissue. FIGS. 2 and 3 are graphs of temperature over time for various embodiments of the thermal management system 100 described above with reference to FIGS. 1A-1C. FIG. 2 shows the rapid temperature response of a method in which the contact member 110 was placed against a gelatin mass selected to simulate the temperature response in human tissue. In this method, at the starting points the TECs 120 (FIG. 1B) are driven so that the first portions 122a are cold and the second portions 122b are warm, and the two-phase heat transfer unit 140 is operated to remove heat from the second portions 122b of the TECs 120. The TECs 120 are then reversed so that the first portions 122a are warmed and the second portions 122b are cooled, causing a rapid spike in the temperature from 0° C. to over 20° C. in a few seconds. The TECs 120 can then be reversed again so that the first portions 122a again cool the contact member 110, causing the temperature to rapidly decrease to the starting level. In addition to the rapid increase and decrease in temperature, this test also shows that specific target temperatures can be achieved precisely without overshoot or undershoot and controllably maintained.

FIG. 3 shows another temperature/time plot of the temperature at various depths of 2 mm, 5 mm and 10 mm in a target material simulating human tissue. As shown, embodiments of the thermal management system 100 described above with reference to FIGS. 1A-1C were able to withdraw enough heat to reduce the temperature from about 25° C. to 0° C. in 9 minutes at a depth of 2 mm, 15 minutes at a depth of 5 mm, and 20 minutes at a depth of 10 mm. This is a surprising result for thermal management units having the small, low-profile size of the type shown in FIGS. 1A-1C. This is particularly useful for medical and aesthetic treatments because small, lighter applicators can be used, which enables more complex areas of the body to be cooled and provides more comfort to the patient.

Figure 4:
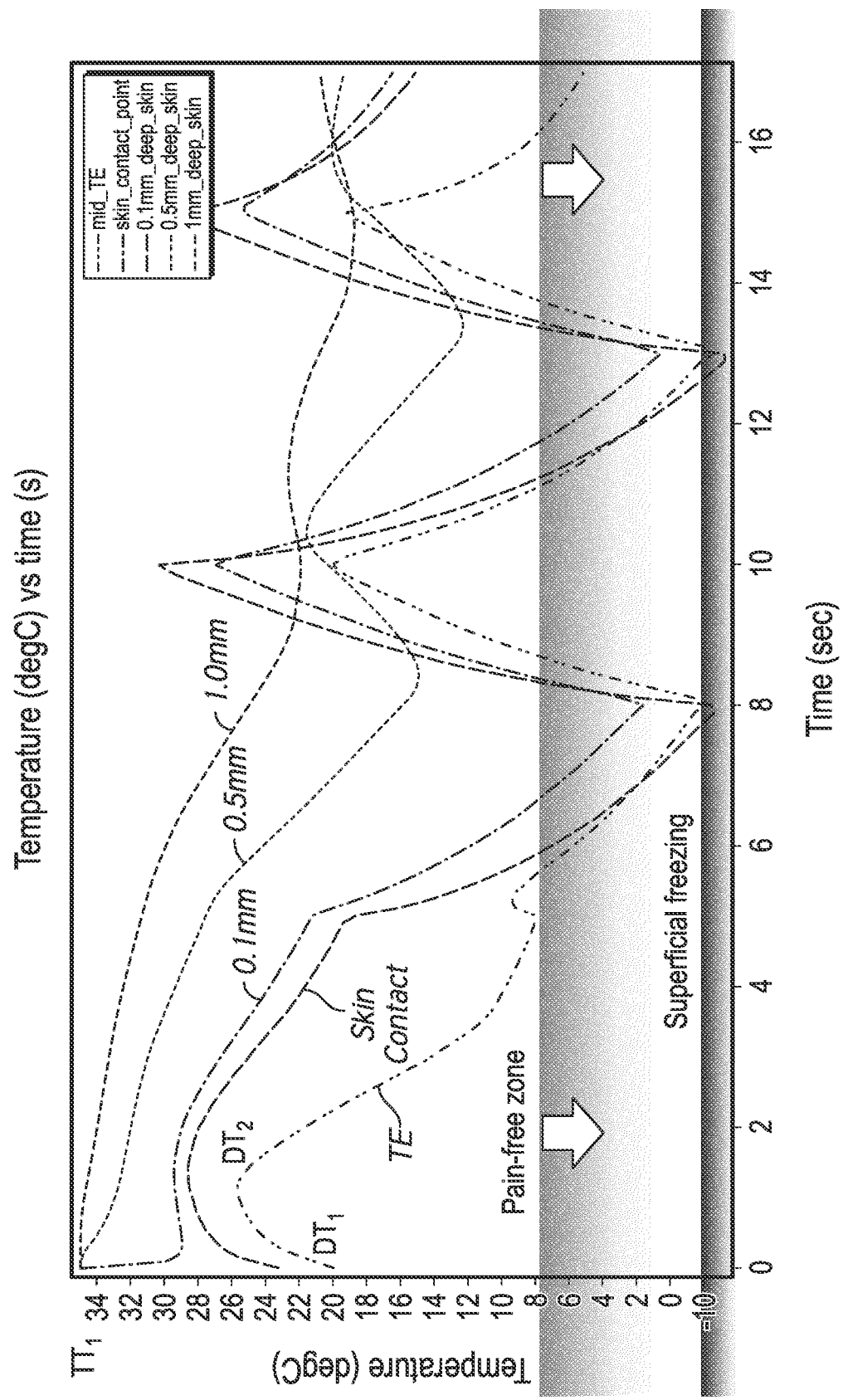
FIG. 4 is a graph of time and temperature of another application of using a thermal management system in accordance with the present technology.

FIG. 4 shows another temperature and time plot of simulated tissue being cooled and heated using a heat management system in accordance with the present technology. The target material 101 is initially at a normal physiological temperature $TT_1$ (Tissue Temperature) of about 35° C. As shown in FIG. 4, the tissue to be treated is at different temperatures as a function of tissue depth with FIG. 4 showing the initial temperature at the skin contact point, 0.1 mm, 0.5 mm and 1 mm depths. The temperature at the midpoint of the TECs between the first and second portions 122a-b is also shown by line TE. Also shown is the temperature of about 8° C. and below where cooling provides an anesthetic effect and the temperature of about −2° C. where tissue freezes superficially. The thermal cooling and heating device is at an initial temperature $DT_1$ of room or ambient temperature of about 20° C. According to one optional aspect, the device may be warmed to a pre-contact temperature $DT_2$ of about 35° C. to lessen uncomfortable contact of a relatively cold device to a relatively warm patient. The device at temperature $DT_1$ is then brought into contact with the skin surface and the TECs are activated to cool the target material from 20° C. to about −2° C. or 20° C. to about −10° C. in about 2 seconds and to provide cooling to the skin. After about 5 seconds, the electricity flows through the device in a direction to cool the device and thereby cool the temperature of the skin contact point (skin contact green line) to about −2° C. in about 3 seconds. The tissue at a depth 0.1 mm is cooled to a temperature of about 2° C. in about 8 seconds. The temperatures of the tissue at depths of 0.5 mm and 1.0 mm are higher and are above the temperature where the cooling can provide an anesthetic effect. At this point, the skin can be treated with laser light, for example, where the skin at the contact surface and at a depth 0.1 mm benefit from an anesthetic effect from cooling. At this point, the direction of current is reversed such that the device heats the skin in about 2 seconds to a temperature of about 30° C. at the skin contact point and about 27° C. at a depth 0.1 mm below the surface. At this point, the direction of current is again reversed to cool the skin to a temperature of about −2° C. in about 3 seconds, where the skin can be treated with laser light, for example.

Several aspects of the present technology, such as the rapid change in temperature and precise control of the temperature of the target material 101, are enabled by the small size yet high heat transfer rate of the heat transfer unit 140 compared to the TECs 120 and/or the contact member 110. In several embodiments, TECs 120 and the contact member 110 or just the TECs 120 alone have a first volumetric heat capacity and the heat transfer unit 140 has a second volumetric heat capacity that is not more than one of 50%, 100%, 150%, 200%, 250%, 300%, 400%, or 500% of the first volumetric heat capacity. More particularly, the first volumetric heat capacity of the heat transfer unit 140 is only about 50%-200% or 100%-150% of the second volumetric heat capacity of the TECs 120 alone or the combination of the TECs 120 and the contact member 110.

This cycle can be repeated any number of times to treat target tissue and at different target tissue locations. For example, the device can be used to cool down a first target tissue location $TL_1$ in about 2 seconds to a temperature of about 8° C. at which an anesthetic effect is achieved at the surface or 0.1 mm below the surface, and in about 3 seconds to a temperature of about −2° C. where superficial freezing takes place. The tissue $TL_1$ can be treated with laser light, for example, and then the tissue $TL_1$ can be heated to a temperature of about 30° C. or 20° C. or 15° C. in about 2 seconds. The device can then be moved to a second tissue location $TL_2$ where the tissue can be cooled to an anesthetic treatment temperature in about 2-3 seconds for treatment with laser light. The second tissue location can then be heated to about 30° C. in about 2 seconds and the device moved to a third tissue location $TL_3$ where the cooling, treatment and heating cycle is carried out. This cycle can be repeated for any number of tissue locations $TL_N$. Additional cooling and/or heating profiles can be executed using the thermal management systems described herein. For example, the cooling or heating profile may be pulses of cooling (temperature lowering) or heating (temperature raising) effect or sinusoidal pulses. The cooling and/or heating may be accomplished by desired electrical pulses or current through the thermoelectric unit which may be reversed as described herein. According to one embodiment, the cooling and/or heating may be accomplished by controlling the fluid pressure or flow rate to the heat-transfer unit, where such fluid pressure or flow rate is used to remove heat from a heat source contacting the heat-transfer unit.

Figure 5:
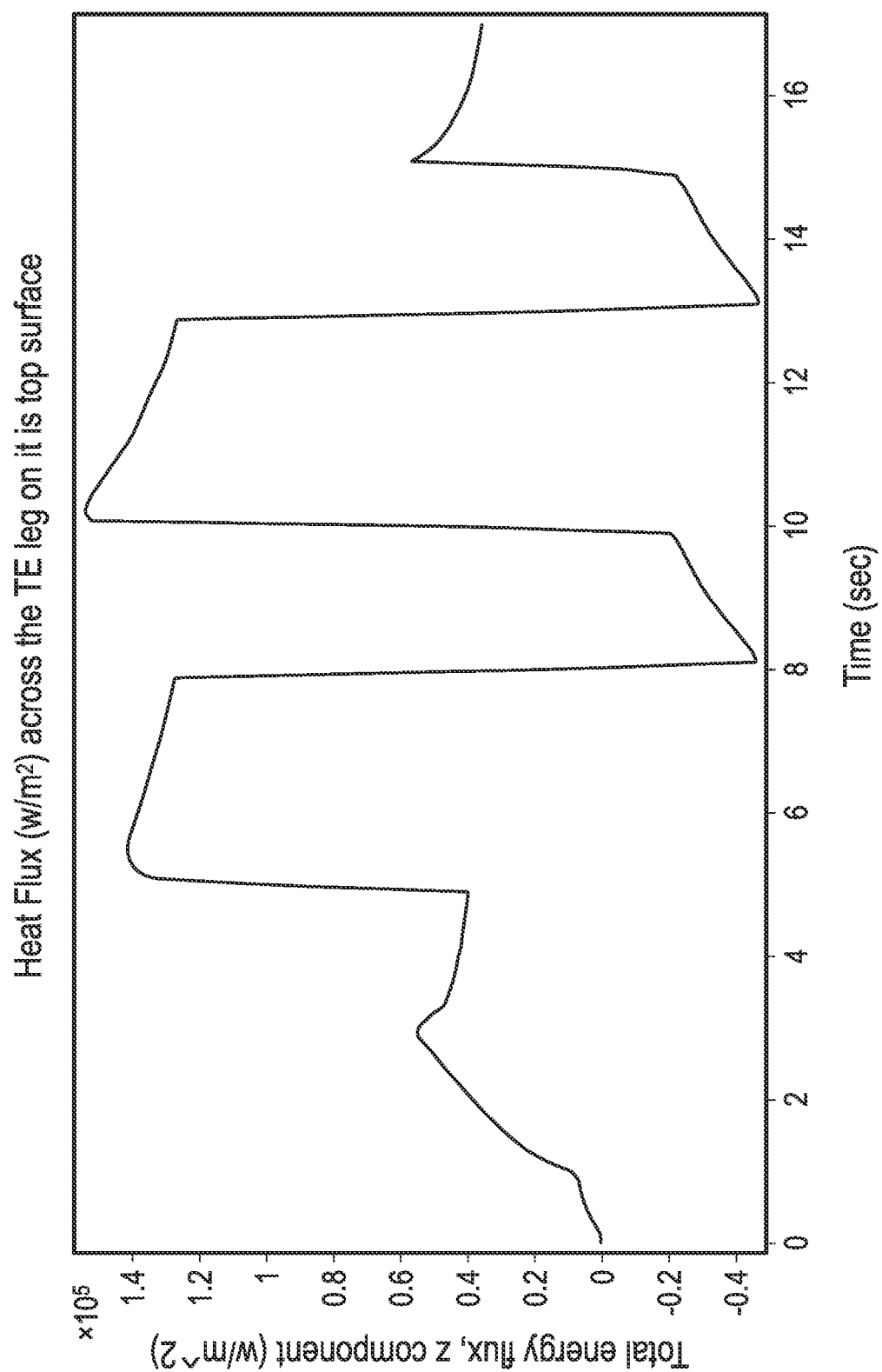
FIG. 5 is a graph of time and energy of a heat flux associated with a thermal management system in accordance with the present technology.

FIG. 5 is a graph showing the heat flux across the TECs 120 at points where current is reversed at 8 seconds, at 10 seconds and at 13 seconds. As shown in FIG. 5, a high heat flux changes in a fraction of a second, which reflects the rapid cooling and heating of the TECs 120 and the rapid cooling and heating of the target material 101. According to one aspect, a target material to be cooled and/or heated is a tissue of a patient undergoing a treatment, such as an energy-based treatment such as laser treatment such as for hair removal or dermatology treatment or needle injection. Other treatments within the scope of the present technology include radiotherapy for cancer treatment, thermal therapies (such as hypothermia or hyperthermia), combined thermal therapy and immunotherapy, acne treatment (long pulse), body sculpting by cooling subcutaneous adipose tissue, invasive or non-invasive RF treatments, HIFU, Ultrasound, laser tattoo removal, ablative laser skin rejuvenation, cellulite treatment, depigmentation and skin rejuvenation. According to such treatments, the tissue is cooled to numb the tissue before, during or after such treatment to reduce pain during treatment. According to one aspect, the tissue is cooled to numb the tissue before, during or after laser or needle treatment to reduce pain during treatment. Accordingly, the thermal cooling or heating devices provide an anesthetic effect. After cooling, the tissue may be heated to bring the tissue to a higher temperature, such as normal tissue temperature. Since the device is intended to contact tissue, the device may be heated to normal tissue temperature to provide a pleasant contact to the patient and to avoid an unpleasant contact such as when a cold device is placed against the warm tissue of the patient.

According to one aspect, the device for cooling tissue as described herein is integrated into a laser system or other medical device to protect the epidermis and reduce pain in the treatment area and/or inhibit damage to non-target tissue (e.g., skin adjacent the target tissue). The device also provides temporary topical anesthetic relief for laser treatments and injections, and thereby improves the efficacy of the laser or other medical device. With respect to timing of irradiation of the laser or operation of the medical device, cooling can take place before, during or after treatment, which includes pre-cooling, parallel cooling and post-cooling.

The primary objective of laser therapy for patients with specific dermatoses is to maximize thermal damage to the target chromophores while minimizing injury to the normal skin. However, in some cases, the threshold dose of incident laser beam for epidermal injury can be very close to the threshold for removal of the chromophore. Dark-skinned patients are more susceptible to these problems because of high epidermal melanin which competes as a significant chromophore for laser energy, leading to increased pain, blistering, scarring and dyspigmentation. The devices for heating and cooling tissue described herein may selectively cool the most superficial layers of the skin to reduce pain, blistering, scarring and dyspigmentation. The goal is cooling of the epidermis to prevent the elevation of temperature beyond the threshold temperature that causes thermal injury. Since cooling protects the epidermis, a high fluence laser beam can be delivered to the skin. This is referred to as the theory of spatial selectivity of the cooling. To target the chromophores within blood vessel, stem cells, hair follicles, etc., a treatment temperature should be reached. However, the treatment temperature will often damage the epidermal keratinocytes and melanocytes. Device for cooling and heating skin described herein can maintain a lower temperature at the epidermal level yet reach the required higher treatment temperature at the target depth in the tissue, which often provides better outcomes of laser procedures. In addition, cooling will diminish the amount of edema, which often develops as a complication of laser procedures. Accordingly, the thermal management systems of the present technology can protect the superficial layers of the skin from collateral thermal damage.

Several embodiments of heat management systems in accordance with the present technology are a unitary component on the face of a hand-held medical instrument, or the heat management systems may be a separate component that can be attached to the medical instrument. For example, the thermal management systems can be added to lasers including a hand-held laser emitting device, such as the Candela GentleLASE Plus laser which is a non-invasive light therapy device specifically designed to eliminate unwanted hair from all parts of the body. The Candela GentleLASE Plus generates a pulse of intense, concentrated light which is directed through a small handpiece to the treatment site. According to one aspect, the heat management systems may be fabricated at the tip of the handpiece of such commercially available laser systems. After the skin is cooled using a heat management system to protect the skin and provide an anesthetic effect, the laser energy passes through the heat management system and through the skin to the hair follicle, where the energy is absorbed by pigment in the hair and hair follicle. As a result, the hair root is selectively damaged without damaging the delicate pores and structures of the skin. The laser is pulsed, or "turned on", for only a fraction of a second. The duration of the pulses is carefully calibrated so that laser energy will be absorbed by the hair follicle without transferring excessive heat to the surrounding skin. Thereafter, the heat management system warms up the skin and is then moved to a second target skin location where the process is repeated.

According to one aspect, the heat management systems cool the tissue upon contact and may be referred to as a contact cooling treatment. According to one aspect, the heat management systems may have transparent parts or materials to allow light to pass therethrough while the heat management systems contact the tissue, such as when cooling or heating the tissue. According to another aspect, the heat management systems may have channels or holes therethrough to allow light or another treatment modality or implement to pass therethrough while the heat management systems contact the tissue.

In accordance with certain aspects of the present technology, the heat management systems cool the tissue while also controllably compressing the skin/tissue to reduce blood flow in the target material; therefore, decreasing the oxyhemoglobin which is an active chromophore. Furthermore, skin compression brings deeper targets like the hair follicles closer to the skin surface, which enhances the absorption of laser energy so less fluence can be used to heat targets and/or more energy reaches the target.

The thermal management systems of the present technology are accordingly useful in treatment methods related to dermatological treatments in general, including hair removal, tattoo removal, acne treatment, ablative laser treatment, invasive and non-invasive RF treatment, radiotherapy such as radiation beam therapy for treating cancerous tissue, such as a tumor. The thermal management systems can be activated before, during and after treatment. According to one aspect, the heat management systems can be used to induce localized thermal damage to tumor tissue, entirely within a desired surface area or at individual locations or points within a given tissue surface area. For example, within a given tissue surface area, the tissue may have no or little thermal damage and may also have locations of thermal damage. The locations of thermal damage may be ordered or may be random, as desired according to a treatment.

Figure 6:
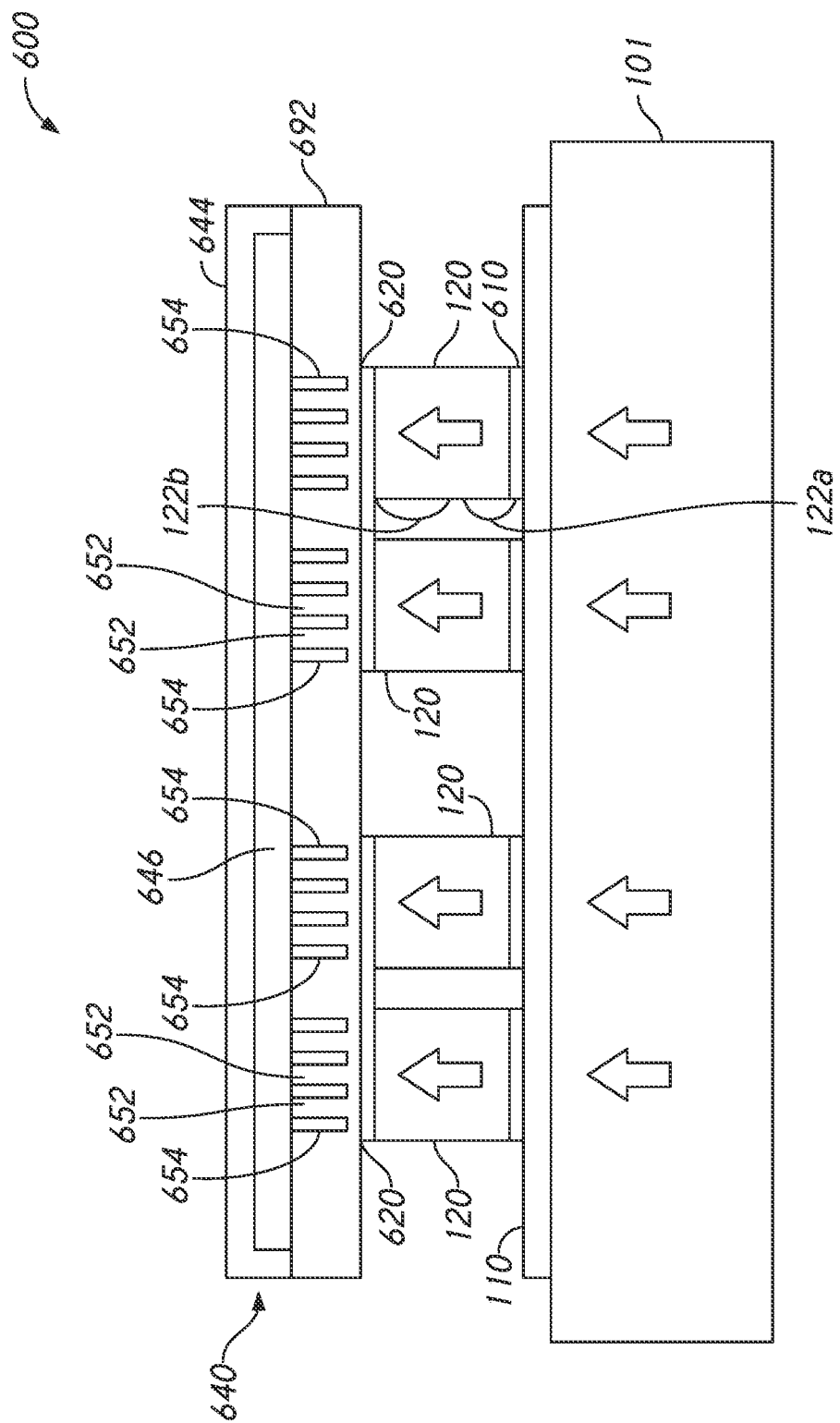
FIG. 6 is a schematic cross-sectional view of a thermal management system in accordance with the present technology.

FIG. 6 illustrates an embodiment of a thermal management system 600 for cooling a target material 101 in conjunction with a primary therapy. The thermal management system 600 can be similar to the thermal management system 100 described above, and like reference numbers refer to similar or identical components. The thermal management system 600 can include a thermally conductive contact member 110 and TECs 120 such that several TECs 120 are thermally coupled to the contact member 110. The TECs 120 have electrical contact pads 610 at the first portions 122a and contact pads 620 at the second portions 122b, and electrical current can flow between the contact pads 620 and the contact pads 610 to cool the first portions 122a of the TECS 120, while heat flows in the opposite direction as indicated by the arrows in the target and the arrows in the TECs 120.

The thermal management system 600 includes a two-phase heat transfer unit 640 thermally coupled to the TECs 120. The heat transfer unit 640 can be similar to the heat transfer unit 140 described above. For example, the heat transfer unit 640 can have a base 642, a top 644 and a phase-change chamber 646 defining a vapor space in the space between the base 642 and the top 644. The heat transfer unit 640 can further include microfeatures 652, such as pins or elongated panels, that define microchannels 654. The microfeatures 652 can be superimposed with corresponding TECs 120 as shown in FIG. 6. In operation, a working fluid in the microchannels 654 evaporates to cool the TECs 120.

The base 642 and the top 644 can be made from a transparent material or have transparent portions, such as sapphire, diamond, glass, transparent ceramics, alumina, transparent polymer nanocomposites with crystallized alumina, etc. As a result, the thermal management system 600 is well adapted to be used with lasers and other skin treatment devices. In operation, the laser beam or other radiation beam can pass through the transparent top 644 and base 642 in the areas between to TECs 120 to heat target tissue at a depth in the tissue, such as hair follicles or collagen, while the TECs 120 and heat transfer unit 640 cool the epidermis and dermis where nerves are located. As a result, the laser treatment can heat the target tissue to higher temperatures for longer periods of time to enhance treatment outcomes, while the thermal management system 600 cools the skin surface to protect the skin from burning and to mitigate or even alleviate pain.

Figure 7:
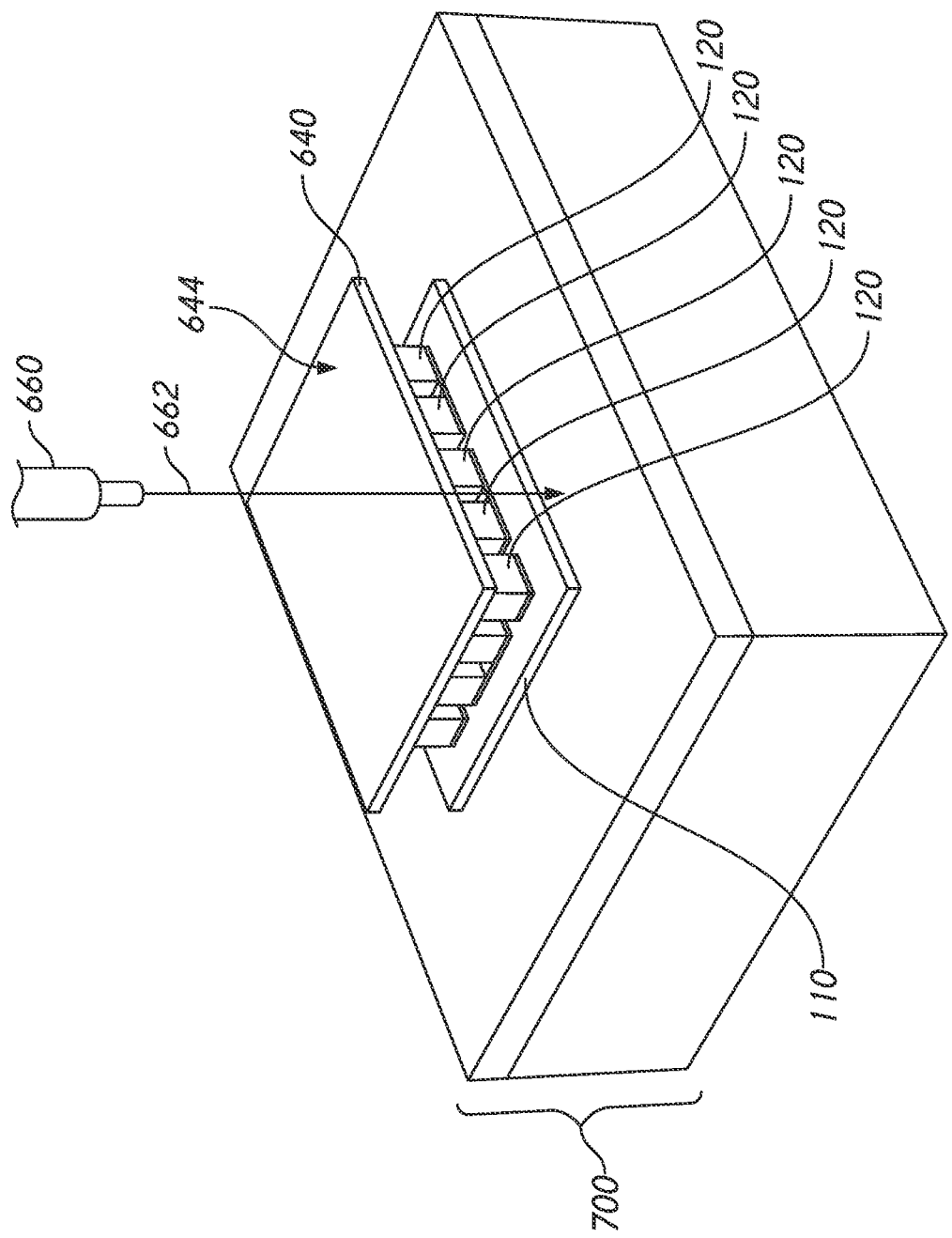
FIG. 7 is an isometric view of using the thermal management system of FIG. 6 in accordance with the present technology.

FIG. 7 is an isometric view of the thermal management system 600 of FIG. 6 in operation. A volume of tissue 700 is shown in the X-Y-Z direction including fat and skin. The surface of the skin is at position 0 with the depth of the tissue shown. A thermally conductive and transparent contact member 110 contacts the skin and TECs 120 as described herein are thermally coupled to the contact member 110. The two-phase heat transfer unit 640 as described herein is thermally coupled to the TECs 120. In operation, a laser 660 or other treatment modality (e.g., external beam radiation device) directs an energy beam 662 through the transparent components in the spaces between the TECs 120.

Figure 8A:
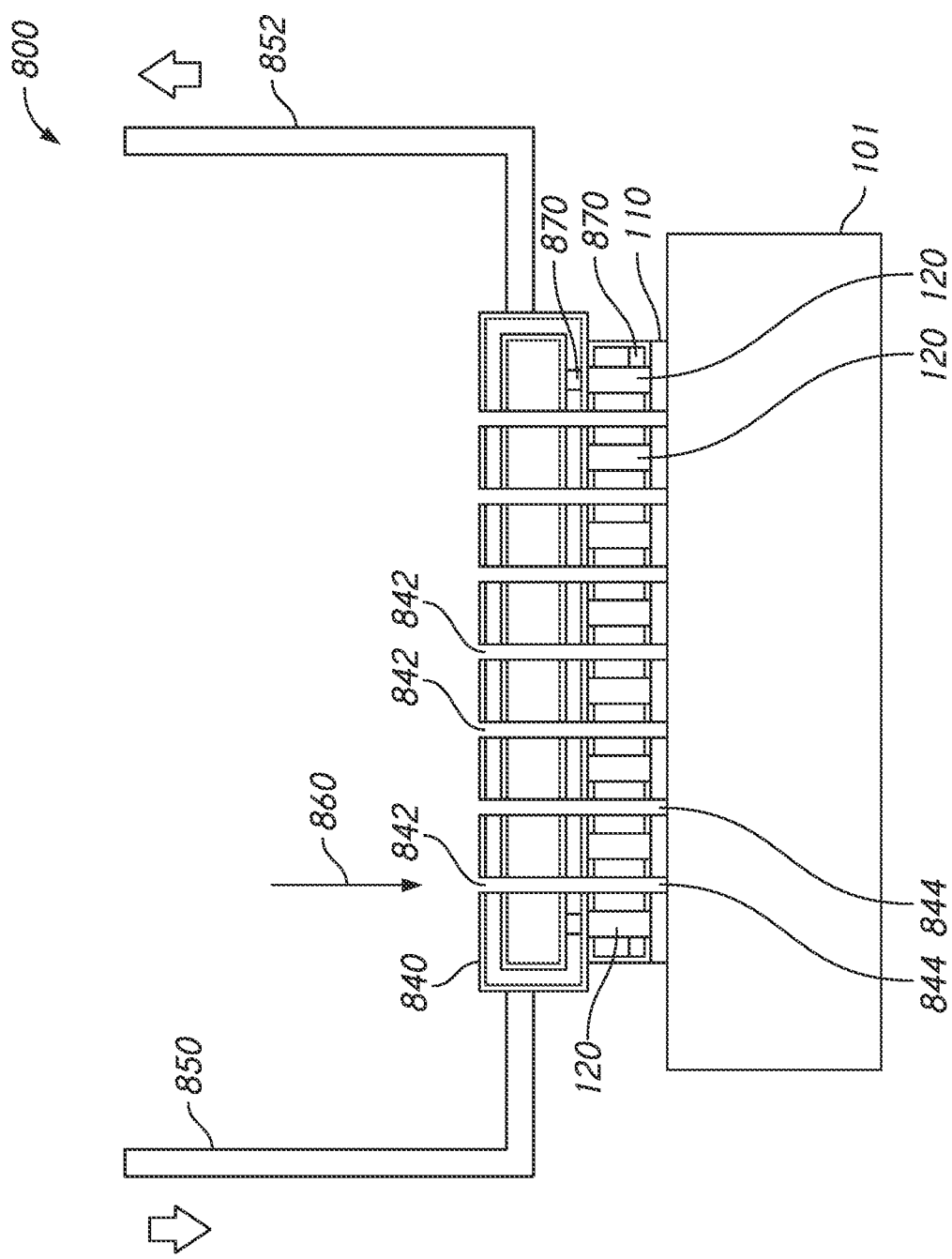
FIG. 8A is a schematic side view and FIG. 8B is a schematic top view of a thermal management system in accordance with the present technology.
Figure 8B:
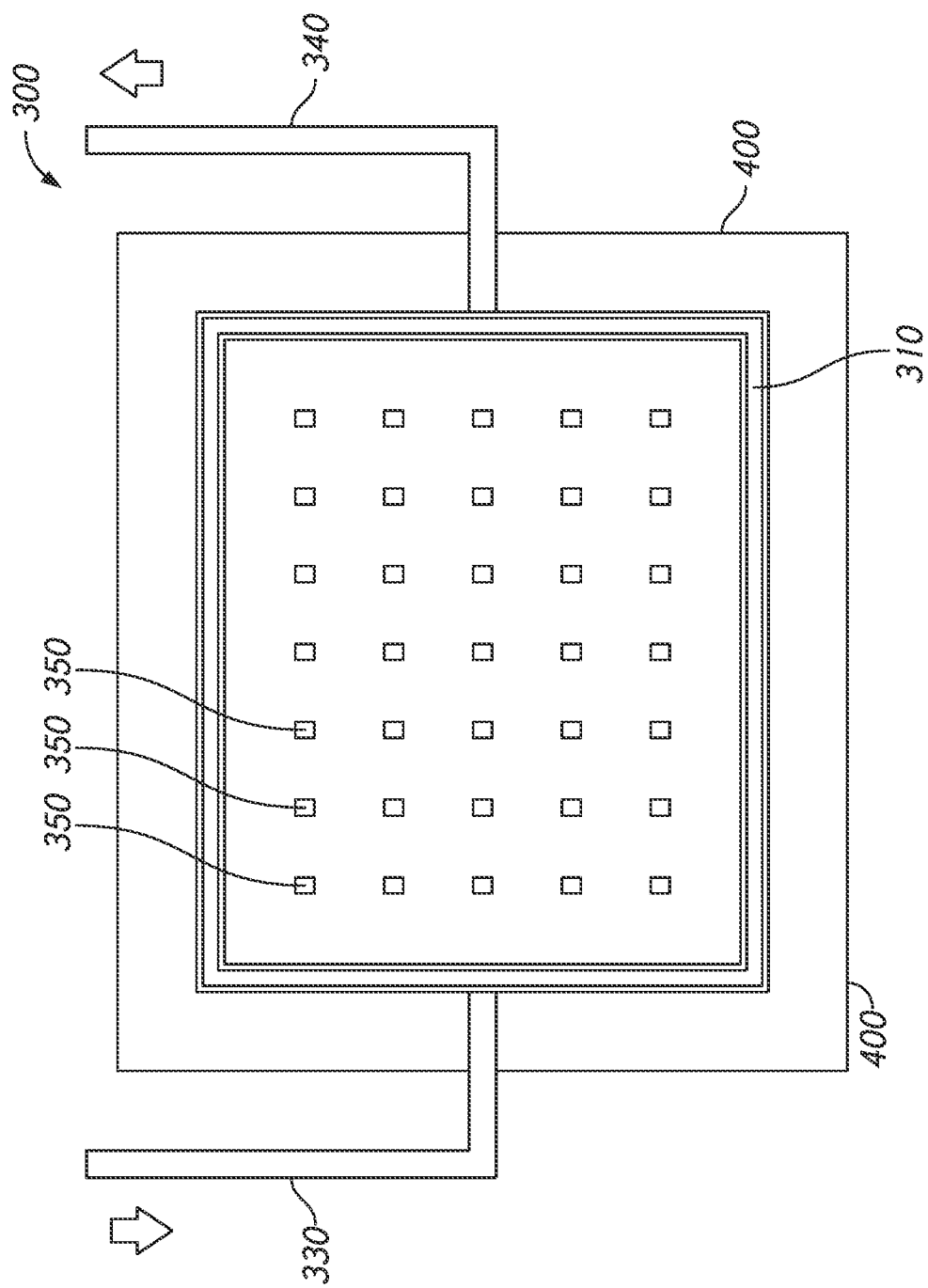

FIG. 8A illustrates a side view of a thermal management system 800 and FIG. 8B is a top view of the thermal management system 800. The thermal management system 800 includes a contact member 110, TECs 120 thermally coupled to the contact member 110, and a two-phase heat transfer unit 840 thermally coupled to the TECs 120. A liquid phase working fluid flows through a first conduit 850 to the heat transfer unit 840, and a vapor phase of the working fluid flows from the heat transfer unit 840 through a second conduit 862. The heat transfer unit 840 can be similar to the heat transfer unit 140, except that the heat transfer unit 840 includes access holes 842 and the contact member 110 has openings 844 aligned with the access holes 842. The access holes 842 and the openings 844 are at least generally aligned with spaces between the TECs 120.

In operation, a needle or an energy beam 860, such as laser light, radiation beam or another type of beam, is directed through the access holes 842 and openings 844. According to one aspect, the access holes 842 and openings 844 also allow vapor and/or tissue debris to be ejected from the target material surface during treatments, such as ablative laser treatments. In this manner, the thermal management system 800 need not be removed during treatment of the target material. The system 800 can also include temperature sensors 870 at or near the TECs 120. According to one aspect, depending on the application, the two-phase heat transfer unit 840, the TECs 120, and the high conductivity contact member 101 are made from specific materials transparent to parts of electromagnetic wave spectrum.

According to one aspect, a vacuum system may be used to fix any of the thermal management systems 100, 600, 800 described above to the surface of the target material during treatment. The vacuum system is used to maintain or improve thermal contact with the target material, such as skin. According to one aspect, the same vacuum system or a separate vacuum system may be used to evacuate or contain any tissue debris and vapors which may be created during ablative energy-based treatments such as ablative carbon dioxide treatments. According to one aspect, fixing the thermal management systems 100, 600, 800 to the skin surface during treatment prevents debris from the ablative laser treatment from clogging access holes which may be present in the thermal management system. The vacuum system also contains any vapor or debris thereby preventing the debris, particles and the gas to be inhaled by the patient or the operator of the system. The vacuum system also helps to reduce the blood flow in the skin, which is useful for both laser procedures and treatments for reducing subcutaneous adipose tissue for body sculpting.

Figure 9:
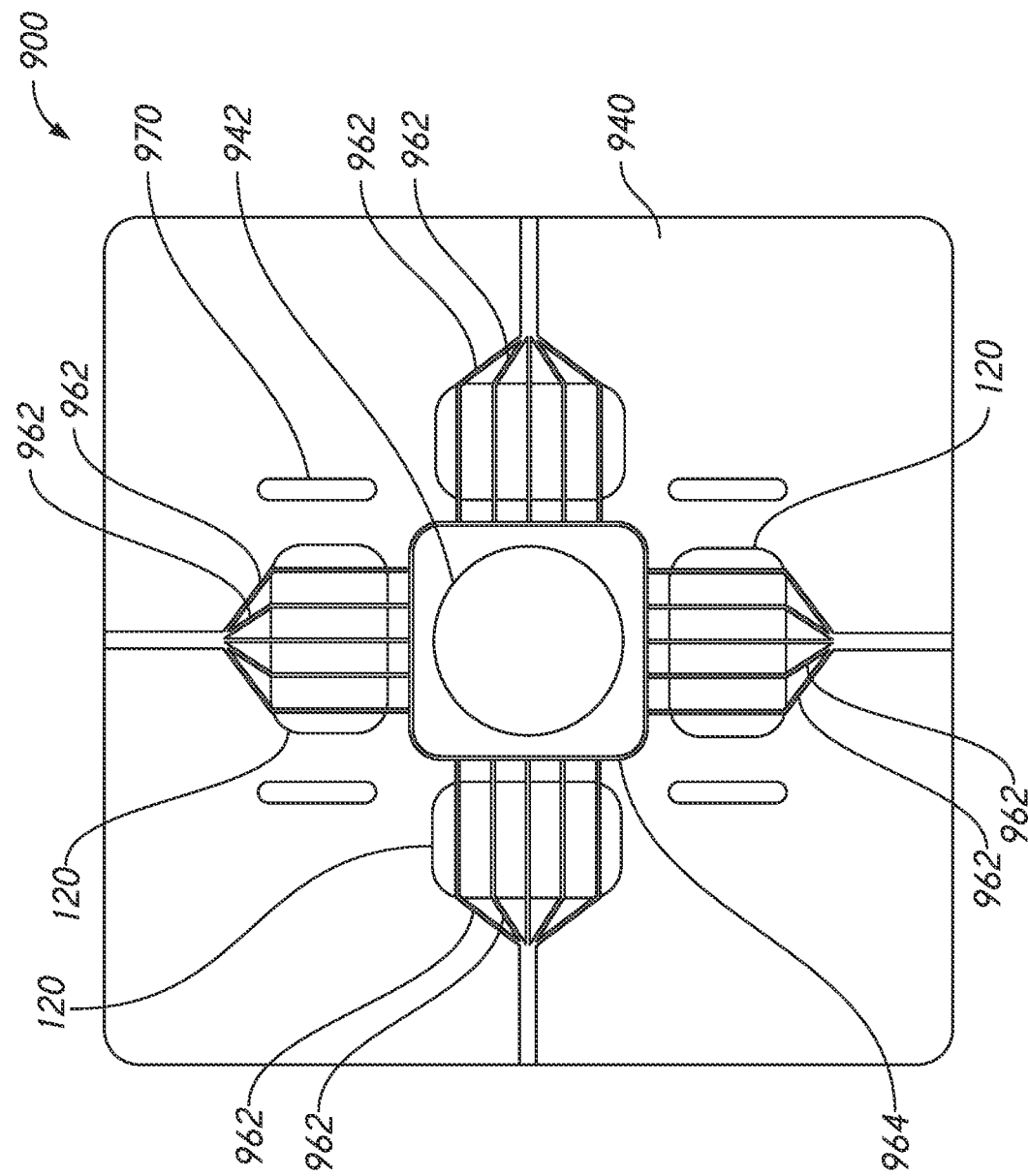
FIG. 9 is a schematic top view of a thermal management system in accordance with the present technology.

FIG. 9 is a schematic view of a thermal management system 900 having TECs 120 and a heat transfer unit 940. The heat transfer unit 940 has an array of microchannels 962 arranged such that discrete groups of microchannels 962 are aligned with individual TECs 120. The microchannels 962 can be commonly connected at the inlets or the outlets by a common duct 964. The heat transfer unit 942 further includes an optional access hole 942 and temperature sensors 970 located in different positions and layers throughout the system to provide feedback signals to control the heat flux and temperature at the device-target interface. Each thermal management system 900 can be an individual cell.

Figure 10:
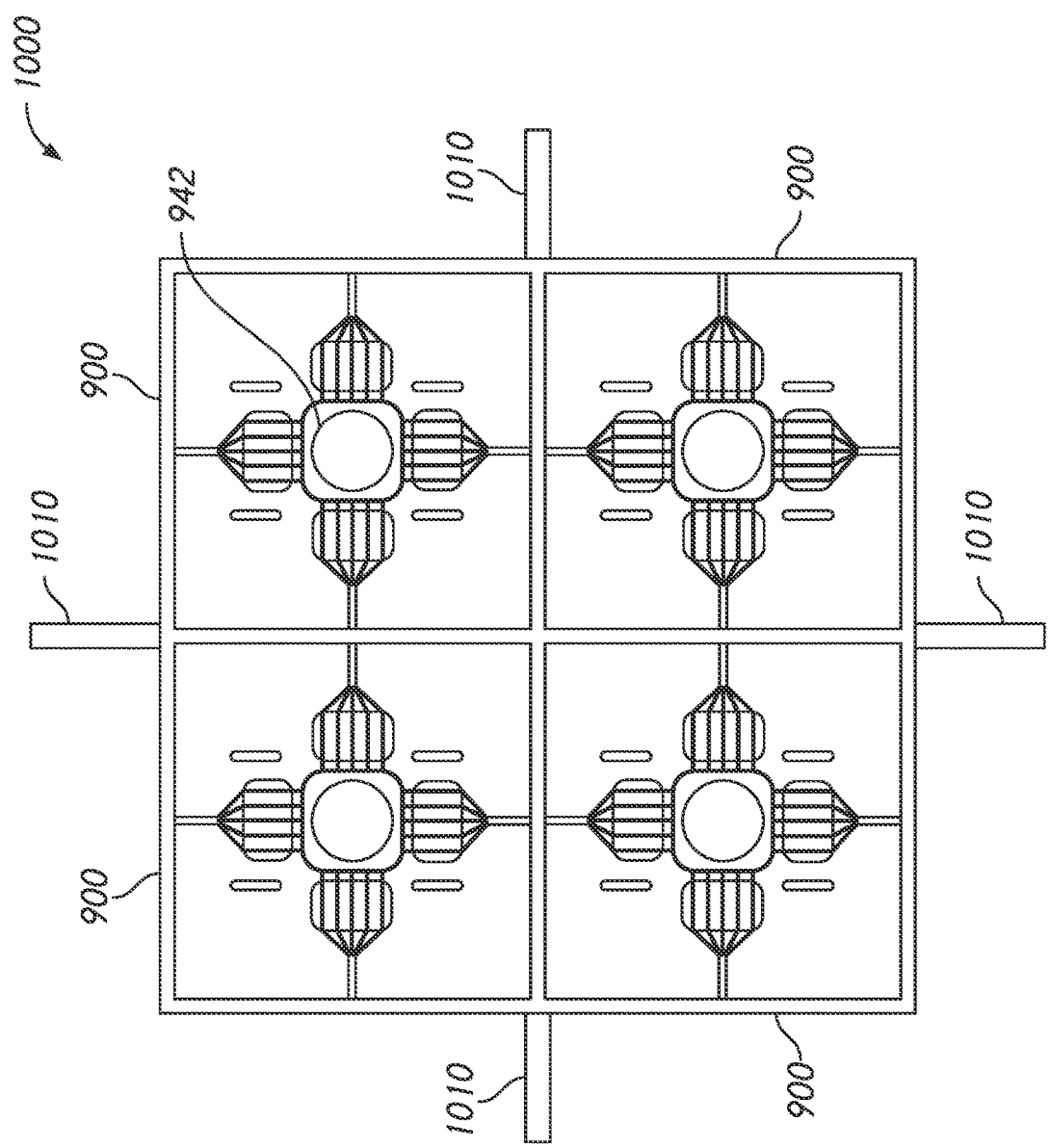
FIG. 10 is a schematic top view of a device with a thermal management system in accordance with the present technology.

FIG. 10 is a schematic view of an assembly 1000 of several thermal management systems 900. The assembly 1000 can include fluid delivery lines 1010 to carry the liquid phase of the working fluid to the individual thermal management systems 900. The number and arrangement of the TECs as well as microchannels can be changed depending on any specific applications. A cap (not shown) covering the channels provides the space required for vapor to exit the system. In some configurations the vapor is purged into the surrounding (e.g., open systems which can be used with any embodiment herein), while in other configuration vapor is condensed back into the liquid phase in a closed system. The interface between the thermal management system 900 and the target can be flat or curved with specific surface profiles for any particular application. The thermal management system 900 can be made out of flexible materials to conform to the shape of the target. The thermal management system 900 can also include heating elements to quickly raise the temperature at the target-system interface if needed. The system can operate at pressures between 0.0001 bar and 20 bar and temperatures between −270° C. and 1000° C.

Figure 11:
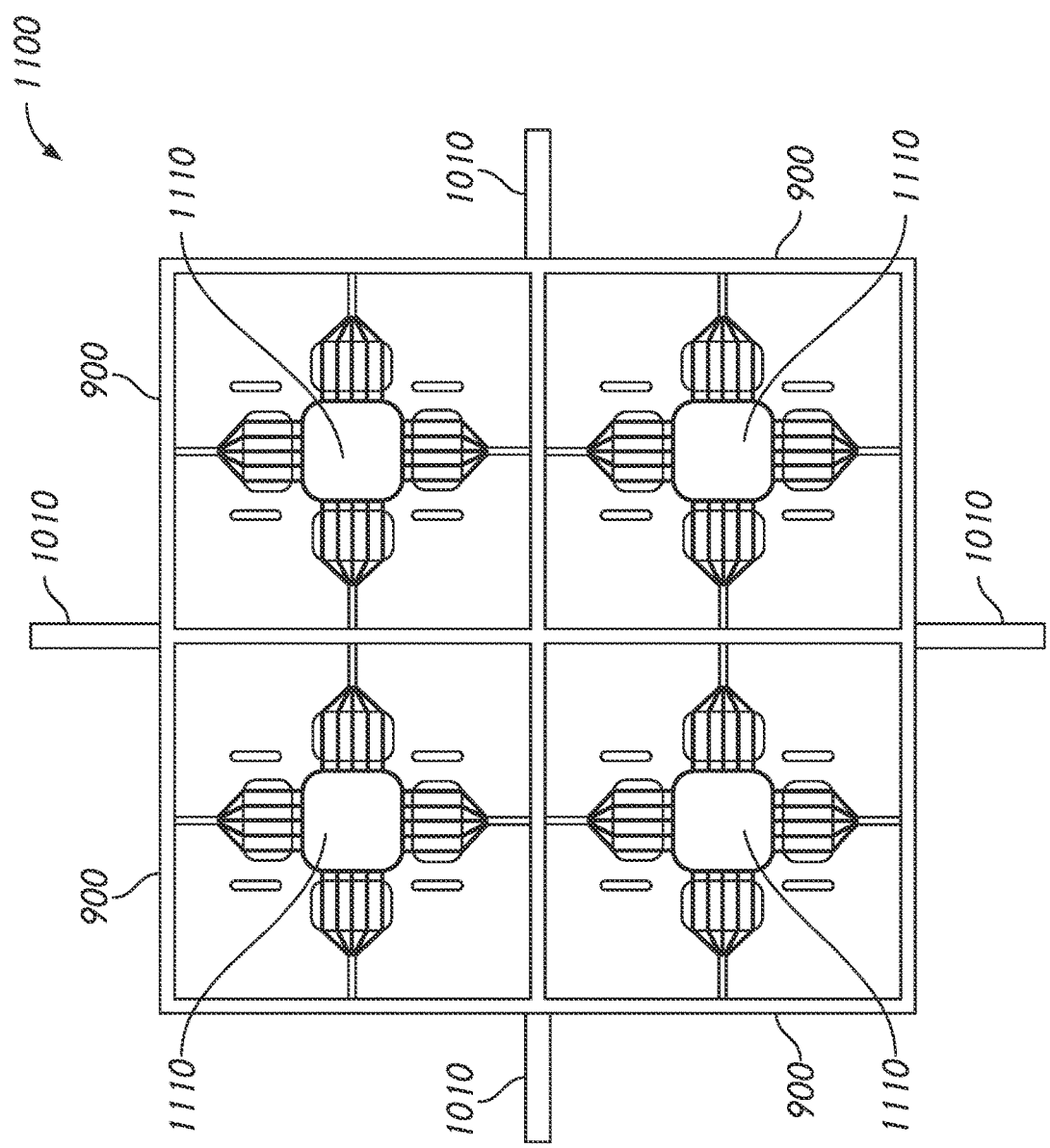
FIG. 11 is a schematic top view of a device with a thermal management system in accordance with the present technology.

FIG. 11 is a schematic view of another assembly 1100 of several thermal management systems 900. In this embodiment, the individual thermal management systems 900 do not have access holes, but instead have a solid central region 1110. The central region 1110 can be a transparent material so laser light or other radiation beams can be transmitted through the center area to the target material below.

Figure 12:
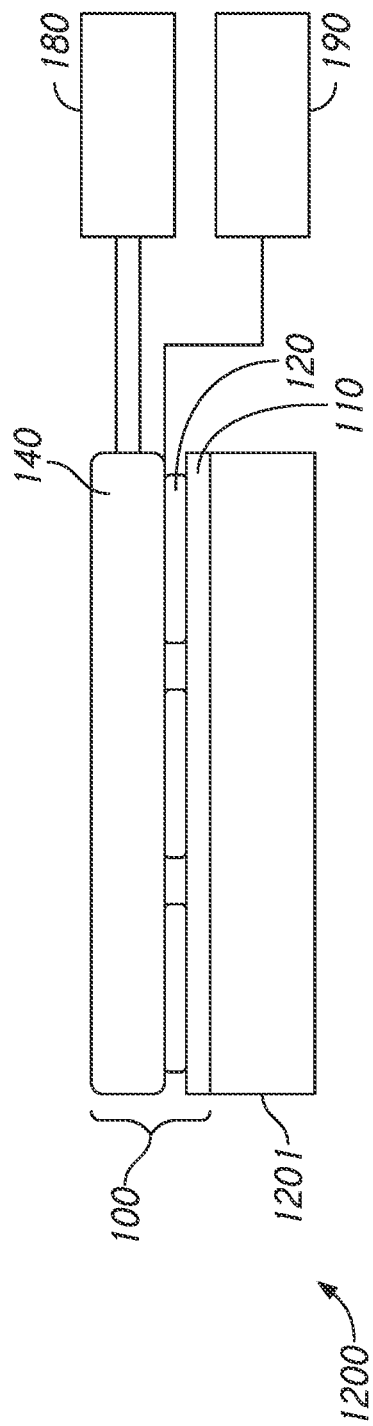
FIG. 12 is a schematic cross-sectional view of a semiconductor device with a thermal management system in accordance with the present technology.

FIG. 12 is a schematic view of a semiconductor assembly 1200 having a semiconductor device 1201 and the thermal management unit 100 described above with respect to FIGS. 1A-1C. The thermal management system can alternatively have heat transfer units as described with respect to FIGS. 15A-20E herein. The semiconductor device 1201 can be a processor, memory device, light emitting diode, or other heat producing device. In this embodiment, the contact member 101 is attached to the semiconductor device 1201.

Figure 13:
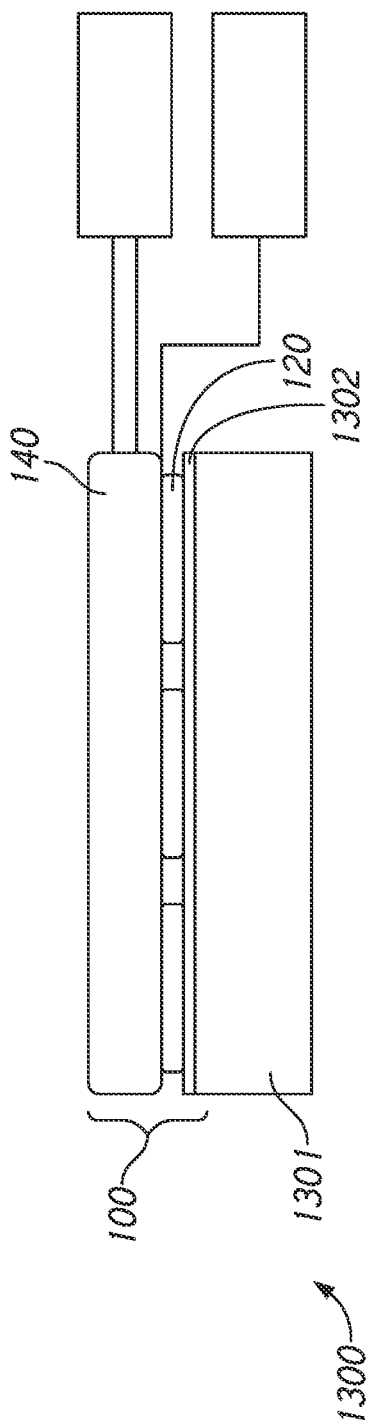
FIG. 13 is a schematic cross-sectional view of a semiconductor device with a thermal management system in accordance with the present technology.

FIG. 13 is a schematic view of a semiconductor assembly 1300 having a semiconductor device 1301 and a version of the thermal management system 100 without the contact member 110. The thermal management system can alternatively have heat transfer units as described with respect to FIGS. 15A-20E herein. In this embodiment, the semiconductor device has a passivation material 1302, and the TECs 120 of the thermal management system 100 are attached to the passivation material 1302.

Figure 14:
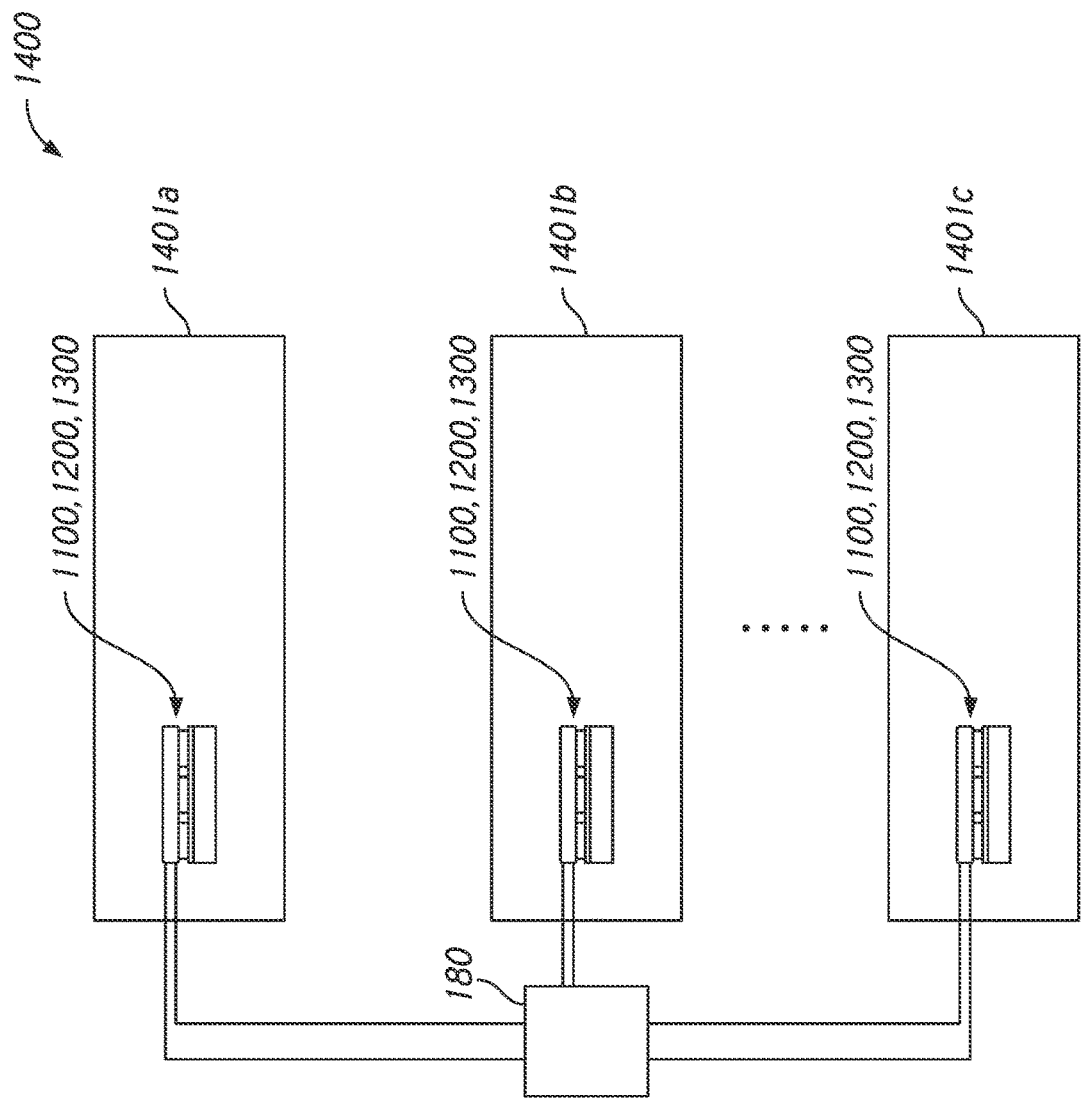
FIG. 14 is a schematic view of an assembly of electronic devices, such as servers, with thermal management systems in accordance with the present technology.

FIG. 14 is a schematic view of a number of devices 1401a-n (collectively referred to as devices 1401), such as servers, that are cooled using thermal management systems in accordance with the present technology. Each device 1401 can have a semiconductor assembly similar to or the same as the semiconductor assemblies 1200 and 1300 described above, or each device 1401 can have a separate thermal management system 100, 600, 800 attached to the housing of the device 1401 in addition to or in lieu of the thermal management systems attached to the semiconductor devices. Additionally, the thermal management systems can alternatively have heat transfer units as described with respect to FIGS. 15A-20E herein. Each of the assemblies 1200 and 1300 can be coupled to a common condenser 180. In operation, the assemblies 1200 and 1300 can be cooled using the low-profile thermal management system 100 internally to reduce or eliminate the need for large, cool airflows over the devices 1401. This may save significant amounts of energy to cool many servers compared to convention air-cooled servers. This may accordingly simplify constructions and maintenance of larger server farms as well.

Any of the foregoing heat-transfer units can include aspects of the evaporative structures described in U.S. Pat. No. 10,217,692 hereby incorporated by reference in its entirety and specifically for its teaching of designs for two-phase evaporative cooling units. As For example, the evaporative structure may include a series of protrusions extending down from a base into an evaporative fluid. Alternatively, the evaporative structure may include a series of walls forming a series of channels with evaporative fluid therebetween. The evaporative structure may include a porous material configured to receive an evaporative fluid. The evaporative structure may include walls having a fractal topography configured to receive an evaporative fluid. The evaporative structure is designed to promote evaporation of the working fluid to cool the TECs. The evaporative structure is operatively connected to an inflow conduit or inlet port and an outflow conduit or outlet port to operatively provide an evaporative fluid flow path through the evaporative structure. According to one embodiment, the inflow conduit is operatively connected to a pump and a reservoir of evaporative fluid to pump evaporative fluid through the evaporative structure. The inflow conduit is configured to receive the evaporative fluid as it enters the evaporative structure. The outflow conduit is configured to receive the evaporative fluid as it exits the evaporative structure. The evaporative structure or a separate condenser may also include a condensing plate or unit to condense evaporated evaporative fluid for collection and/or redistribution to the evaporative unit, as is known in the art. The evaporative structure may contact a plurality of TECs such that a single evaporative structure cools a plurality of TECs.

Heat-transfer units according to the present technology may alternatively include other two-phase cooling devices, such as Joule-Thompson cooling devices, spray cooling devices and the like. Such heat-transfer units include cryogen spray (dynamic) cooling, such as pulsed cryogen spray using non-toxic 1,1,1,2-tetrafluoroethane also known as R-134a (boiling point: −26.2° C.) or liquid nitrogen or liquid carbon dioxide, for example. Other materials useful for cooling include HFOs, HFCs, nitrogen oxide, alcohols, hydrocarbons (such as isobutane, propane), water, ammonia, particle-fluid mixtures, binary (or more than two) mixtures of materials (or fluids), and the like. A heat-transfer unit may take the form of a container pressurized with a gas or fluid which when released or sprayed onto the surface of the hot side of the thermoelectric unit, causes cooling of the thermoelectric unit. When the contents of the container or cartridge is empty, the container or cartridge may be disposed and a new full container or cartridge may be used with the system as a heat-transfer unit. A heat-transfer unit according to the present technology transfers the heat generated by the TECs where it is dissipated away from the TECs, thereby allowing the TECs to cool or otherwise regulate the temperature of the target material in the cooling mode of the system. The heat-transfer unit advantageously prevents the TECs from overheating where heat generated by the TECs overtakes the cooling ability of the TECs.

The two-phase heat transfer unit described in U.S. Pat. No. 10,217,692 operates on the principle of evaporative cooling. An aspect of one embodiment is a two-phase heat transfer device including a reservoir configured for containing a working fluid; a base member configured to be in communication with and adjacent to a heat source; elongated members extending distally away from the base member configured to form passages between the elongated members, the elongated members include a proximal region and a distal region; and with the distal region of the elongated members at least partially inserted or immersed into the working fluid.

According to one aspect, the two-phase heat transfer unit includes a reservoir configured for containing a working fluid; a base member having a first face and a second face, wherein the first face and the second face are generally opposite each other; the first face of the base member is configured to be in thermal communication with and adjacent to a heat source, such as the TECs as described herein.

Elongated members extend distally away from the second face of the base member configured to form passages between the elongated members; the elongated members include a proximal region and a distal region, wherein the distal region is configured to be at least partially inserted into the working fluid; and the passages are configured to accommodate vapor that may be produced from the working fluid so as to define a vapor space. The elongated members may be a protrusion, a wall, a panel, a pin, a post, or a rod; as well as any combination thereof. The base member and the elongated members may be comprised of thermally-conducting non-porous solid such as silicon, diamond, copper, silicon carbide, graphite, silver, gold, platinum, copper or silicon oxide—as well as other materials as desired, needed or required. It should be appreciated that the base member and the elongated members—particularly the distal regions may be comprised of at least in part porous material. The working fluid may comprise water, oils, metals, octane, hydrocarbons, Penatane, R-245ca, R-245fa, Iso-Pentane, halogenated hydrocarbons, halogenated alkanes, HFOs, HFCs, ketones, alcohols, or alkali metals—as well as other materials as desired, needed or required.

An aspect of an embodiment provides, but is not limited thereto, a two-phase heat transfer device. The device may comprise: a reservoir configured for carrying a working fluid; a base member having a first face and a second face, wherein the first face and the second face are generally away from each other, the first face of the base member configured to receive thermal energy from a heat source; elongated members extending distally away from the second face of the base member and configured to define respective passages between adjacent elongated members; the elongated members include a proximal region and a distal region, wherein the distal region is configured to be at least partially inserted into the working fluid; and the passages are configured to accommodate vapor produced from the working fluid so as to define a vapor space.

According to one aspect, a two-phase heat transfer unit includes a reservoir configured for carrying a working fluid; a base member configured to receive thermal energy from a heat source; elongated members extending distally away from the base member and configured to define respective passages between adjacent elongated members; the elongated members include a proximal region and a distal region, wherein the distal region is configured to be at least partially inserted into the working fluid; and the passages are configured to accommodate vapor produced from the working fluid so as to define a vapor space.

According to one aspect, a two-phase heat transfer unit includes a reservoir configured for carrying a working fluid; a base member configured to receive thermal energy from a heat source; elongated members extending distally away from the base member and configured to define respective passages between adjacent elongated members; and the elongated members include a proximal region and a distal region, wherein the distal region is configured to be at least partially inserted into the reservoir.

According to one aspect, a two-phase heat transfer unit includes a reservoir configured for carrying a working fluid; a base member configured to receive thermal energy from a heat source; elongated members extending distally away from the base member and configured to define respective passages between adjacent elongated members; and at least some of the elongated members are configured to be at least partially inserted into the reservoir.

According to one aspect, a two-phase heat transfer unit includes a reservoir configured for carrying a working fluid; a base member configured to receive thermal energy from a heat source; elongated members having at least one wall, wherein the elongated members extend distally away from the base member and are configured to define respective passages between adjacent elongated members; wherein the elongated members include a proximal region and a distal region, wherein the distal region is configured to be at least partially inserted into the working fluid; a recess topography disposed on the at least one wall of the elongated members, wherein the recess topography is configured to accommodate the working fluid; and the passages are configured to accommodate vapor produced from the working fluid so as to define a vapor space.

The two-phase heat transfer devices for any of the embodiments described with reference to FIGS. 1A-20E provide high evaporation and cooling capacity for use with the TECs when cooling the target material. An advantage associated with such two-phase heat transfer devices includes increased cooling capacity per unit area, controlled and optimized evaporation, prevention of boiling, and prevention of drying of the evaporator. An aspect associated with an approach may include, but is not limited thereto, using a recess topology to increase suction of working fluid in the direction toward the heat source. An aspect associated with an approach may include, but is not limited thereto, using a non-wetting coating or structure to keep working fluid away from the spaces between elongated members of an evaporator and using a wetting coating or structure to form thin films of working fluid around the distal region of the elongated members.

Two-phase heat transfer devices may utilize any combination of a wetting coating, a wetting target material, a non-wetting coating, or a non-wetting target material to attract working fluid to certain areas of the device and repel working fluid from certain areas of the device. For example, the device may comprise a wetting coating such as a hydrophilic coating or a lyophilic coating disposed on the distal region of the elongated members to attract working fluid. Alternatively, the distal region of the elongated members may be comprised of a wetting target material (i.e., material) such as a hydrophilic target material or lyophilic target material. In another example, the device may comprise a non-wetting coating such as a hydrophobic coating or a lyophobic coating disposed on the proximal region of the elongated members and the second face of the base member located between the elongated members to repel the liquid working fluid. Alternatively, the proximal region of the elongated members and the second face of the base member located between the elongated members may be comprised of a non-wetting target material such as a hydrophobic target material (i.e., material) or a lyophobic target material.

Two-phase heat transfer units may comprise a vapor space defined by passages which widen in the direction of vapor flow. For example, the passages may extend radially from a central region, wherein the pathway is radial from the central region. In another example, widening vapor space is formed by reducing the number of the elongated members (e.g., per unit length/area) in the direction of vapor flow. Alternatively, the passage may have a width that is uniform or narrows. Alternatively, the passage may have a width that may provide a combination of widening and narrowing, as well as remaining uniform.

FIGS. 15A-15E show a thermal management system 1500 having the contact member 110, a TEC 120, and a two-phase heat transfer unit 1502 for cooling and/or heating a target material 1501 (also referred to herein as "heat source 1501"), which can be any of the target materials disclosed above. Referring to FIG. 15A, the two-phase heat transfer unit 1502 has a phase-transition chamber 1504 (also referred to herein as a reservoir 1504) containing a working fluid 1505, a base 1506 contacting the TEC 120, and microfeatures 1514 (also referred to herein as elongated members 1514) projecting from the base 1506 to form passages 1520. FIG. 15B is an enlarged partial view of a single passage 1520 (also referred to as a channel) of FIG. 15A, and FIG. 15C shows an enlarged partial view of the thin film region of a meniscus 1503 of the working fluid 1505 shown in FIGS. 15A and 15B. The evaporating thin film region of the meniscus 1503 is where the bulk of evaporative heat transfer occurs as this region of the meniscus 1503 has a very low thickness and therefore high conductive resistance. The non-evaporating thin film region is where adhesion forces between liquid molecules and the solid surface are extremely strong few if any of the molecules can transition from the liquid phase to the vapor phase. Thus, the evaporating thin film region represents the region of enhanced evaporation and heat transfer.

The working fluid may be water, oils, metals, octane, hydrocarbons, Pentane, R-245ca, R-245fa, isopentane, halogenated hydrocarbons, halogenated alkanes, HFOs, HFCs, alkenes, ketones, alcohols, or alkali metals. It should be appreciated that the working fluid 1505 should be compatible with the other materials that make up the device so they will not react chemically to create non-condensable gases or cause other deleterious effects. Further, as an example, the working fluid may be any liquid or gas. Moreover, the working fluid may be molten metal or liquid metal, such as lithium or the like.

The elongated members 1514 can extend away from the base member 1506 in the direction opposite the target material 1501 and the distal regions of the elongated members 1514 are partially immersed or inserted in the working fluid 1505. The heat travels through the solid mass of the base member 1506 and down the microfeatures 1514 directly to the evaporating thin film region of the meniscus 1503 where the bulk of evaporative heat transfer occurs. The heat is thus more readily provided to the evaporation thin film region, which in turn eliminates or at least reduces the potential of boiling within a passage 1520 such that ordered and efficient evaporation can be maintained continually.

The two-phase cooling device can be designed to be operated in any orientation given the orientation of the target material to be cooled or heated. For example, the two-phase cooling device may be designed to be gravity insensitive (i.e., omnidirectional) if the channel width or spacing between the pins is smaller than a certain size such that surface forces (capillary forces) are dominant compared to volumetric forces such gravity. To avoid capillary forces from pulling the liquid into the spacing between the pins or channels thereby reducing or eliminating the vapor space, a non-wetting coating can be used to repel the liquid from entering that space. According to an additional embodiment, a target material such as tissue may be below two-phase cooling device or it may be above the two-phase cooling device.

Still referring generally to FIG. 15A, another advantage of this (but not limited thereto) and other embodiments of the two-phase heat transfer device is the efficient delivery of liquid phase working fluid to the evaporation sites. Because the liquid phase of the working fluid 1505 is delivered to the reservoir of the phase-transition chamber 1504 with only the tips of microfeatures 1514 disposed or immersed therein, the two-phase device does not need to overcome the high shear friction involved with flowing the liquid phase of the working fluid through a multitude of narrow channels in conventional two-phase devices. Thus, dry-out problems are significantly reduced as there is less resistance in delivering the liquid working fluid 1505 to the phase-transition chamber 1504 to replenish the evaporated mass.

As schematically reflected in the block diagram of FIG. 15D, the vapor region 1522 (i.e., where the bulk of the evaporative heat transfer occurs) is adjacent to the heat source. Whereas the liquid phase of the working fluid is relatively distant or remote from the heat source to avoid or mitigate boiling in the device and augment flow of liquid working fluid, among other benefits.

FIG. 15E schematically illustrates the general circuit of the heat flow, HF, traveling within an embodiment of the two-phase heat transfer unit 1540 of FIG. 15A. Heat from the heat source travels through the solid mass of the microfeatures 1514 (see FIGS. 15A-15C) and beyond the vapor space 1522 (see FIGS. 15A and 15B) toward the region of the thin liquid film and intrinsic liquid meniscus. The liquid phase of the working fluid 1505 in the reservoir is located furthest from the heat source and thereby requires the greatest distance for the heat to travel. As such, the thin liquid film and intrinsic liquid meniscus are relatively close to the heat source. The alignment as schematically shown in FIG. 15E, enables the heat transfer device to generate superheated vapor without inducing boiling in the intrinsic liquid meniscus and liquid reservoir. Accordingly, this feature improves the quality of the heat removed by the heat transfer device and the efficiency of the heat transfer device, which can be integrated in the various cooling applications as disclosed herein. Moreover, due to this arrangement, the temperature of the proximal portions of the solid mass of the microfeatures 1514 (see FIGS. 15A-15C), i.e., "walls," is higher than the saturation temperature of the thin liquid film and intrinsic liquid meniscus. This prevents liquid condensate from accumulating in the vapor space 1522 (see FIGS. 15A and 15B), which eliminates or reduces of blockage of the vapor space 1522 with liquid condensate.

FIGS. 16A-16E schematically illustrate additional embodiments of the phase change thermal management system 1500 removing heat from the target material 1501. For example, the heat source 1501 can be the surface of a computer chip as well as any of the other heat dissipation applications disclosed herein. The target material 1501 is in communication with a first face 1508 of a base member 1506, and a second face 1510 of the base member is on the opposite side of the first face 1508. The microfeatures 1514 extend distally away from the second face 1510. For example, the base member 1506 and the microfeatures 1514 (or portions thereof) may comprise a thermally-conductive, non-porous solid such as, but not limited thereto, silicon, diamond, copper, silicon carbide, graphite, silver, gold, copper, titanium, platinum, graphene, or metal alloys. Additionally, or in combination, the base member 1506 and the microfeatures 1514 (or portions thereof) may have coating such as, but not limited thereto, gold, platinum, copper, graphene, or silicon oxide.

Figure 16A:
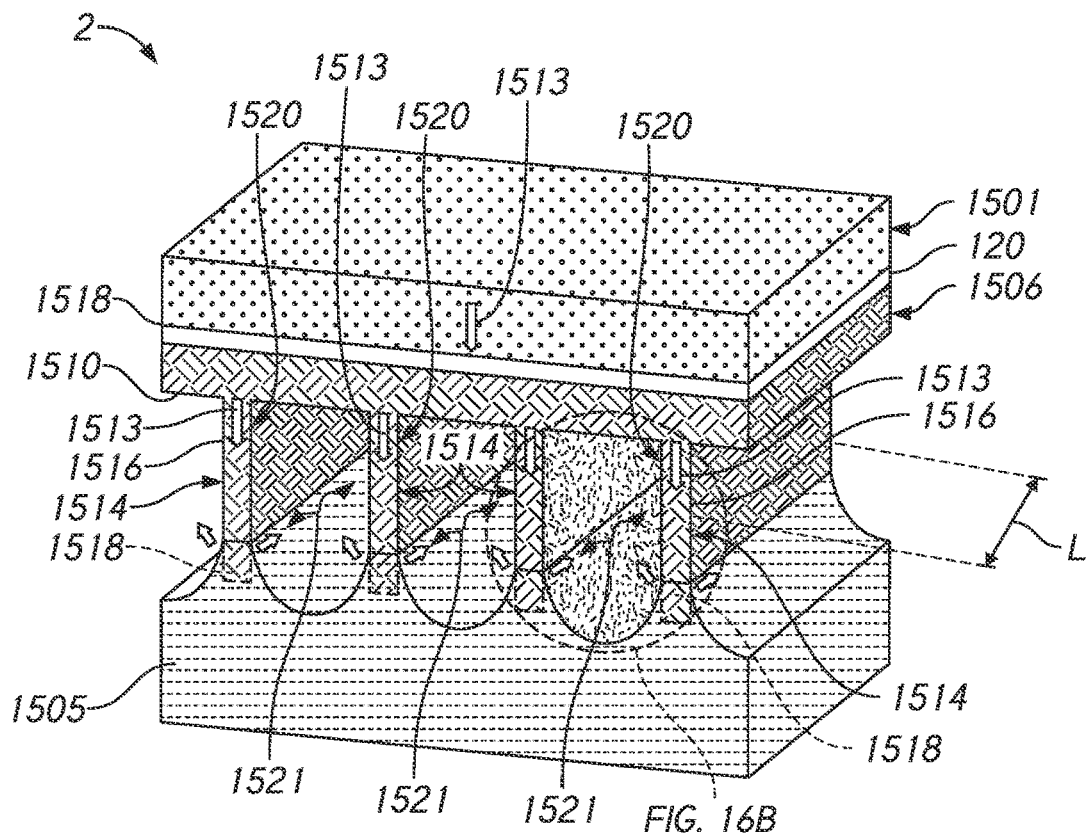
FIG. 16A schematically illustrates an embodiment of a phase change heat transfer device with continuous, ordered evaporation without disruption from boiling and/or dry-out.

The microfeatures 1514 can be pins, posts, rods, walls, panels or other structures that efficiently conduct heat and can be constructed to have the desired spacing between microfeatures 1514. Referring to FIG. 16A, the portion of the microfeature 1514 closer to the base member 1506 defines a proximal region 1516 and the portion that is further away from the base member 1506 defines a distal region 1518. The distal region 1518 is at least partially submerged in the working fluid 1505, creating a thin film of the working fluid 1505 around the distal region 1518. The heat flow 1513 travels (i.e., conduction) from the target material 1501 through the base member 1506 and the proximal region 1516 to the distal region 1518, and the heat is removed from the proximal region 1516 and/or distal region 1518 when a controlled evaporation of the working fluid occurs in the thin film area around the distal region 1518. The evaporated liquid produces a vapor that fills a passage 1520 between the microfeatures 1514 and the base 1506. The heat is transferred from the device when the vapor travels in vapor paths 1521 through the passages 1520 defined by the microfeatures 1514 toward a condenser (not shown). The passages 1520 may, for example, be channels such microchannels or nanochannels.

Figure 16B:
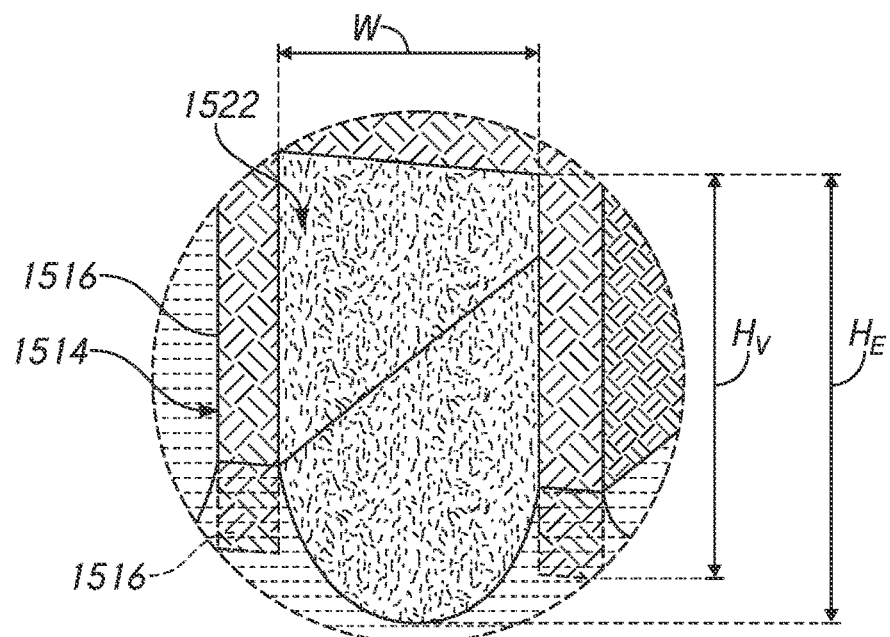
FIGS. 16B is an enlarged partial view of a passage shown in FIG. 16A showing the vapor space and the dimensions of the passage.

FIG. 16A shows an embodiment wherein the microfeatures 1514 are generally straight. In such an embodiment, the proximal region 1516 of at least one microfeature 1514 has a cross section that is substantially equal to the distal region 1518. FIG. 16B is an enlarged partial view of passage 1520 shown in FIG. 16A, particularly the vapor space 1522 and the dimensions of the passage 1520 such as a height, $H_E$, which is the height of the elongated member or passage, a height, $H_V$, which is the height of the vapor space, and width, W, which is the width of the passage (i.e., between elongated members 1514). It should be appreciated that while the stipple pattern representing the vapor space 1522 is only illustrated in the far-right passage 1520, the vapor space 1522 is applicable to any and all passages 1520 (such as but not limited thereto channels or microchannels).

Figure 16C:
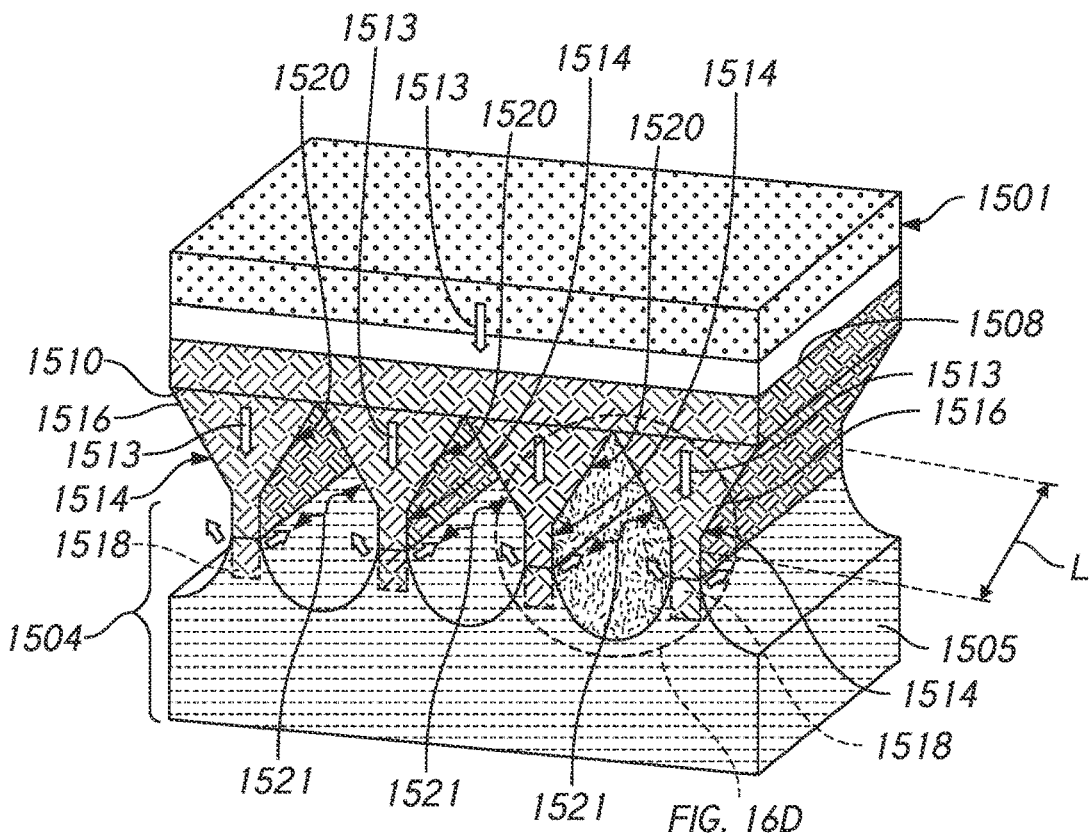
FIG. 16C schematically illustrates another embodiment of a phase change heat transfer device in operation with continuous, ordered evaporation without disruption from boiling and/or dry-out.
Figure 16D:
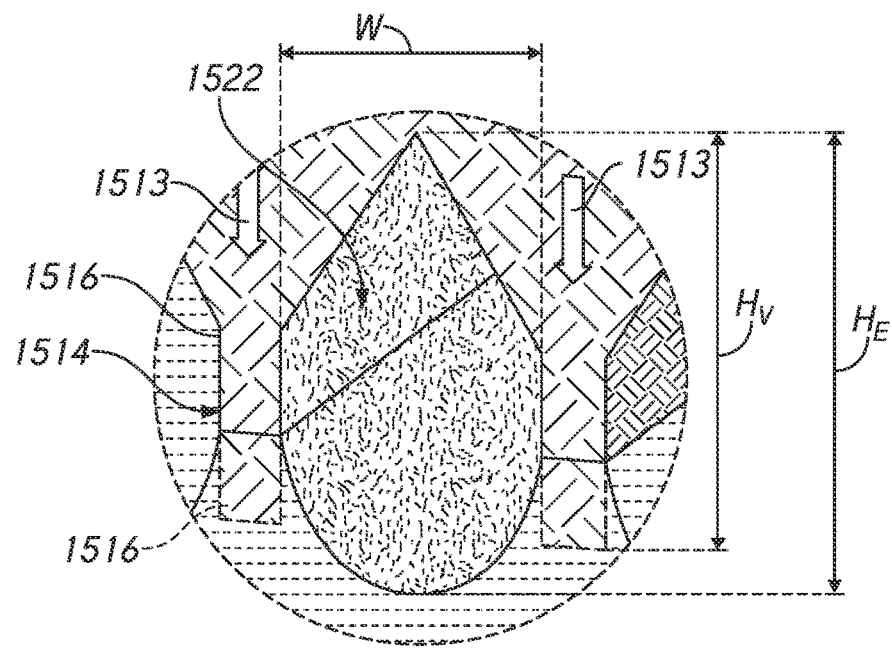
FIG. 16D is an enlarged partial view of a passage shown in FIG. 16C showing the vapor space and the dimensions of the passage.

FIG. 16C shows another embodiment in which the proximal regions 1516 of the microfeatures 1512 are wider than the distal regions 1518. The microfeatures 1514 may accordingly be formed in a variety of shapes and contours. The passages 1520 may be channels, such as microchannels or nanochannels. FIG. 16D is an enlarged partial view of passage 1520 shown in FIG. 16C, showing the vapor space 1522 and the dimensions of the passage 1520, such as a height, $H_E$, which is the height of the elongated member or passage, a height, $H_V$, which is the height of the vapor space, and width, W, which is the width of the passage (i.e., between elongated members, for example). While the stipple pattern representing the vapor space 1522 is only illustrated in the far-right passage 1520, that the vapor space 1522 is applicable to any and all passages 1520 (such as but not limited thereto channels or microchannels).

Without wishing to be bound by any limitations, the dimensions of the device and the dimensions and spacing of the microfeatures 1514 may be any of the foregoing dimensions described above with respect to FIGS. 1A-1C. Additionally, various embodiments may have passages (e.g., channels) with the following dimensions: the width, W, may range from about 100 nanometers to 100 s of microns; the length, L, may range from about 1 micron to 100 centimeters; and the height, H, may range from about 5 microns to 5 millimeters. In other examples, the width, W, could range from about 10 nanometers to 10 millimeters, the length, L, may range from 100 nanometers to 1,000 centimeters or more, and the height, H, may range 100 nanometers to 10 s of centimeters. Any of these dimensions are applicable to any of the passages indifferent of the structure of the elongated members (shape, angles, contours) that define the passages. The dimensions may vary between respective passages relative to one another. Moreover, the dimensions may vary within a given passage itself. Again, these dimensions are merely illustrative.

The vapor space 1522 is the space within the passage 1520 that is filled by vapor during operation. The vapor space 1522 can be defined as the space between the surfaces of the microfeatures 1514, the surface of the second face 1510 of the base member 1506, and the surface of the working fluid 1505 (e.g., the meniscus 1503 of the working fluid 1505). The vapor space 1522 can be created by repelling the working fluid 1505 from the passage 1520 via a non-wetting coating 1528 on the proximal region 1516 of the elongated members and the second face 1510 of the base member. Alternatively, the vapor space 1522 can be created by repelling the working fluid 1505 from the passage 1520 by having the proximal region 1516 of the elongated members and the second face 1510 of the base member be comprised of a non-wetting material 1530 (i.e., material of the structure itself or applicable component, for example). The vapor space 1522 is typically smaller than the passage 1520 because the working fluid fills the portion of the passage 1520. Coating the surface of the distal region 1518 with a wetting coating 1524 or having the distal region 1518 be comprised of a wetting target material 1526 attracts the working fluid 1505 to the distal region 1518, causing the working fluid 1505 to fill the portion of the passage 1520 that is nearby.

In some embodiments, the wetting and/or non-wetting properties of the materials ensure proper flow of the liquid phase of the working fluid to areas where it is desired. The wetting/non-wetting coatings and/or target material of the structure itself may include any portion of the device (base or elongated members) as desired, needed or required. The portion may be of any size, area, thickness or contour as desired, needed or required. Additionally, in some embodiments the wetting and/or non-wetting properties of the materials used in the heat transfer device ensure proper flow of the vapor phase of the working fluid to areas where it is desired that the working fluid be in the vapor phase. The wetting and non-wetting properties may be provided by coating materials or by the inherent properties of the target material materials used to construct the relevant portions of the device. The working fluid 1505 should be compatible with the base member 1506 and microfeature 1514 or any coating materials used so that they will not react chemically to create non-condensable gases or cause other deleterious effects.

According to one aspect, a wetting coating may be on at least a portion of the distal region 1518 of the microfeature 1514 and a non-wetting coating is on a portion of the proximal region 1516 of the microfeature 1514. Again, the location of the wetting/non-wetting coating (or structure) may vary accordingly. It is to be understood that the two-phase cooling system may include wetting coatings, non-wetting coatings or both wetting coatings and non-wetting coatings as desired.

Examples of materials suitable as wetting coating or wetting target material include, but are not limited to: hydrophilic materials, particularly when water is used as working fluid 1505; and lyophilic materials, particularly when a fluid other than water is used as working fluid 1505. Examples of materials suitable as non-wetting coating or non-wetting target material include, but are not limited to: hydrophobic materials, particularly when water is used as working fluid 1505; and lyophobic materials, particularly when a fluid other than water is used as working fluid 1505. Examples of materials suitable for use as hydrophilic/wetting materials may include, but not limited thereto the following: Metals, glass, ceramic, Silicon, Silicon Carbide, and Diamond, for particular group of working fluids. Examples of materials suitable for use as hydrophobic/non-wetting include, but not limited thereto: certain polymers, halogenated hydrocarbons, or chemically altered surfaces of the metals. It should be noted that wetting characteristics are defined for a liquid-solid pair. In an approach, it should be noted that the exact wetting characteristics of a particular embodiment may be determined by the specific interaction between a chosen working fluid 1505 and chosen wetting coating and/or wetting target material surface (material) of the elongated member or base member. Thus, for example, a working fluid 1505 and wetting coating can be selected jointly according to the exact wetting properties of the liquid-solid pair.

The heat flow 1513 passes through the distal region 1518 of the microfeature 1514 to the working fluid 1505. The wetting properties of the wetting coating cause the liquid portion of the working fluid 1505 to wet the distal region 1518 of the microfeature 1514, creating a meniscus in the liquid phase of the working fluid 1505. As with other embodiments of the present technology, an evaporating thin film region will be present in a portion of the working fluid 1505 in contact with the distal region 1518 of the microfeature 1514. Depending on the status of the coating (e.g., portion, location and type of coating), the working fluid 1505 may be in contact with the proximal region 1516 of the microfeature 1514. High heat transfer is achieved by the ability of the continually active thin film evaporation site (as shown in FIG. 15C and discussed with respect to FIGS. 16A-16D) to take full advantage of the latent heat of evaporation of the working fluid 1505. In addition, in this particular embodiment, the non-wetting coating prohibits the working fluid 1505 from covering or filing (or invading) the space surrounded by the proximal region 1516 of the microfeature 1514. This allows the space to act as a vapor passage (e.g., channel or similar structure) for the vapor produced as a result of the evaporation, and flow in its respective vapor pathways. Additionally, the non-wetting coating allows the vapor to flow to the condenser with minimized resistance.

Creating a vapor space in the passage reduces boiling and bubbling. Evaporation occurs at the distal region of the elongated member through controlled and thin-film evaporation. Moreover, in some embodiments, for example those embodiments that may utilize a horizontal configuration, the flow of liquid is less-restricted because it does not travel through narrow passages. The liquid at least in part flows in an open area in the phase-transition chamber 1504, resulting in lower pressure drop. This pooling may be readily applicable wherein a horizontal configuration is implemented or wherein gravitational forces on the fluid in the passages and/or reservoir is essentially negligible. In other orientations, for example, judicious placement of wicks or shaping of passages may be implemented to induce and aid the flow of the liquid. Without wishing to be bound by scientific theory, it is desirable to allow the liquid to flow in the pool (freely) and allow the vapor to flow in the space between channel walls or between pins or a porous target material, etc. Vapor has a much smaller viscosity compared to liquid. Arrangements described herein reduce the overall pressure drop required to circulate/flow the fluid through the system both for open or closed systems. According to one aspect, the active evaporating part of the meniscus may be closer to the heat source in certain configurations. According to one aspect, the thin-film part of the liquid meniscus is closest to the heat source and is exposed to highest temperature. This aspect eliminates/lowers the chance of pool boiling in the channel since the bulk of the liquid can remain in below boiling-temperature (subcooled) while the intense evaporation occurs in the top part where the thin film is located.

Figure 17A:
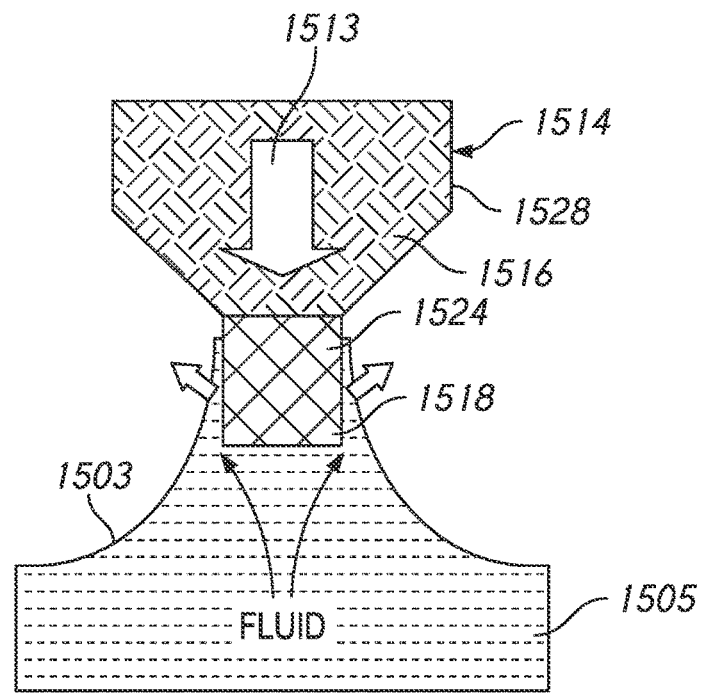
FIG. 17A schematically illustrates an embodiment of a microfeature in contact with the working fluid and illustrates the associated wetting and non-wetting coatings of the embodiment.

FIG. 17A schematically illustrates an embodiment of an elongated member 1514 of the device with wetting a wetting coating 1524 and a non-wetting coating 1528. The wetting coating 1524 may be positioned on a portion of the distal region 1518 of the microfeature 1514. In this embodiment, a non-wetting coating 1528 is positioned upon a portion of the proximal region 1516 of the microfeature 1514. Again, the location of the wetting/non-wetting coating (or structure) may vary accordingly.

Examples of materials suitable as wetting coating 1524 or wetting target material include, but are not limited to: hydrophilic materials, particularly when water is used as working fluid 1505; and lyophilic materials, particularly when a fluid other than water is used as working fluid 1505. Examples of materials suitable as non-wetting coating 1528 or non-wetting target material include, but are not limited to: hydrophobic materials, particularly when water is used as working fluid 1505; and lyophobic materials, particularly when a fluid other than water is used as working fluid 1505. Examples of materials suitable for use as hydrophilic/wetting materials may include, but not limited thereto the following: Metals, glass, ceramic, Silicon, Silicon Carbide, and Diamond, for a group of working fluids. Examples of materials suitable for use as hydrophobic/non-wetting include, but not limited thereto: certain polymers, halogenated hydrocarbons, or chemically altered surfaces of the metals. In one approach, the wetting characteristics of an embodiment may be determined by the specific interaction between a chosen working fluid 1505 and chosen wetting coating 1524 and/or wetting target material surface (material) of the elongated member or base member. Thus, for example, a working fluid 1505 and wetting coating 1524 can be selected jointly according to the exact wetting properties of the liquid-solid pair.

The heat flow 1513 conducts to the distal region 1518 of the microfeature 1514 and from the distal region 1518 to the working fluid 1505. The wetting properties of the wetting coating 1524 cause the liquid portion of the working fluid 1505 to wet the distal region 1518 of the microfeature 1514, creating a meniscus 1503 in the liquid phase of the working fluid 1505. As with other embodiments of the present technology, an evaporating thin film region will be present in a portion of the working fluid 1505 in contact with the distal region 1518 of the microfeature 1514. Depending on the status of the coating (e.g., portion, location and type of coating), the working fluid 1505 may be in contact with the proximal region 1516 of the microfeature 1514. High heat transfer is achieved by the ability of the continually active thin film evaporation site (as shown in FIG. 15C and discussed with respect to FIGS. 16A-16D) to take full advantage of the latent heat of evaporation of the working fluid 1505.

In addition, in this embodiment, the non-wetting coating 1528 prohibits the working fluid 1505 from covering or filing (or invading) the space surrounded by the proximal region 1516 of the microfeature 1514. This allows the space to act as a vapor passage (e.g., channel or similar structure) for the vapor produced as a result of the evaporation, and flow in its respective vapor pathways. Additionally, the non-wetting coating 1528 allows the vapor to flow to the condenser with minimized resistance.

Figure 17B:
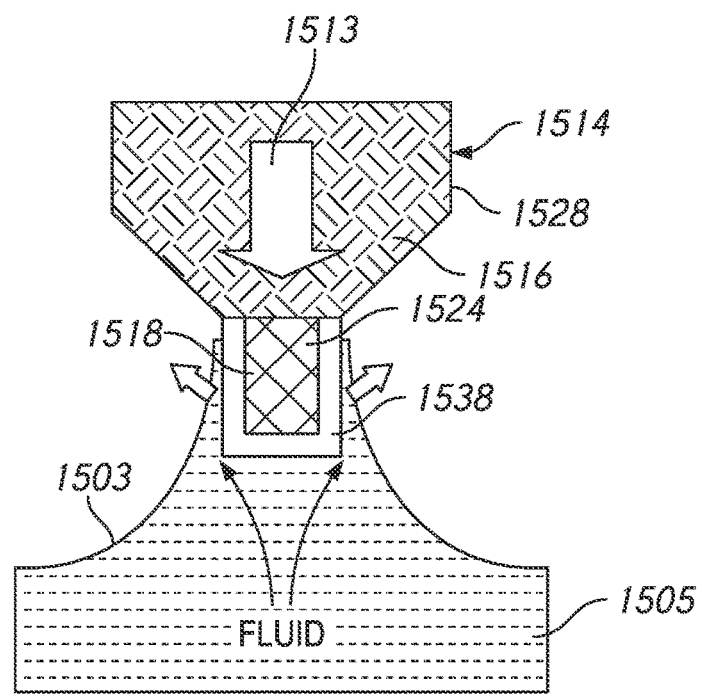
FIG. 17B schematically illustrates an embodiment of a microfeature in contact with the working fluid and illustrates an embodiment with a wick.

FIG. 17B schematically illustrates an embodiment of an elongated member of the device with a wick 1538 (or similar structure) to ensure that the distal region 1518 of the microfeature 1514 remains in constant contact with the liquid phase of the working fluid 1505. The wick 1538 may also increase flow of the working fluid through the elongated members and passages. In such an embodiment, the wick 1538 may provide capillary draw in order to move the liquid portion of the working fluid 1505 from the condenser portion of the device to the evaporator portion. Other approaches may be used, such as systems similar to wicking or pumping systems. Such pumping approaches may include electro-osmotic pumping that may be used to promote the flow toward the thin film.

The wick 1538 may ensure the continuity of the contact between the distal region 1518 of the microfeature 1514 and the liquid portion of the working fluid 1505 along the entire length of the microfeature 1514. In this way, the capillary draw of the liquid portion of the working fluid 1505 to the evaporation sites along the microfeatures 1514 is not compromised and problems associated with dry-out are reduced or avoided.

In other embodiments, the liquid portion of the working fluid 1505 may be moved from the condenser to the evaporator by relying on gravity and allowing the working fluid 1505 to pool back to the reservoir in the evaporator. Continuous contact between the distal region 1518 of the microfeature 1514 and the liquid portion of the working fluid 1505 may then be achieved through a combination of wetting and/or non-wetting treatment of the relevant portions of the microfeature 1514.

Figure 18A:
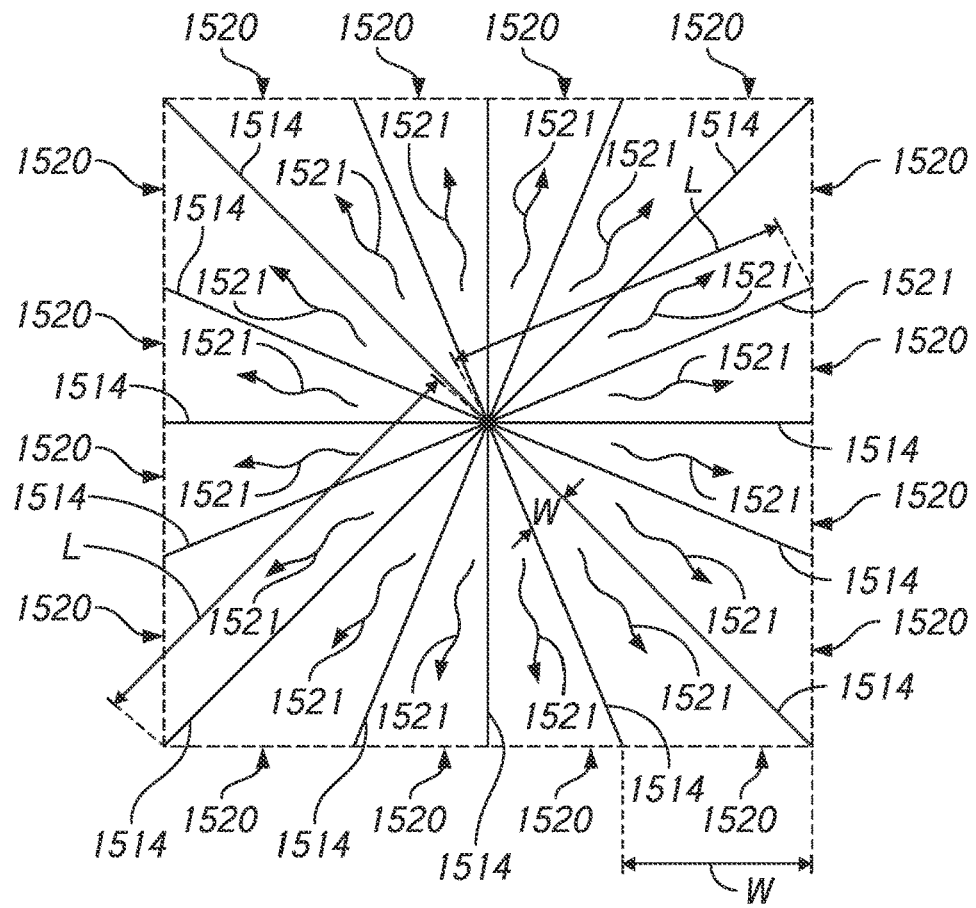
FIG. 18A schematically illustrates a radial arrangement of microfeatures and the corresponding widening passages to accommodate the vapor pathways.

Referring now to FIG. 18A, in some embodiments the microfeatures 1514 may be constructed to form vapor passages 1520 that generally widen along the pathways 1521 in which the accumulating vapor flows. Thus, the passages 1520 configured by the microfeatures 1514 can accommodate vapor flow in a multitude of vapor pathways 1521. In this embodiment, the passages 1520 generally widen to accommodate increasing amounts of vapor traveling in their various vapor pathways 1521. Near the center of a device, the vapor flow rate will be less than near the edge where all the accumulated vapor flow passes before exiting the evaporator towards a condenser. Numerous aspects of the elongated members may be configured and varied, such as, but not limited thereto: size, shape, area, contour, location or position, number provided, and density of the population provided. In a related manner, the various vapor pathways may be configured to be regular or irregular, as determined by the particular configuration of elongated members chosen.

The passages 1520 may be, for example, a channel such as a microchannel. Although, not expressly illustrated, the passage 1520 may have a designated width, W, and area, A, as desired, needed or required. Any of the aforementioned dimensions may increase above or below the micro size magnitude. Additionally, any of the passages may include a variety of shapes and contours as required, needed or desired. They may have a variety of angles or pitches. The passages 1520 may be, for example but not limited thereto, a channel such as a nano-channel.

In FIG. 18A, this general widening of the passages 1521 is achieved by arranging the microfeatures 1514 to define radial passages 1520 to accommodate the pathways 1521 of vapor. In an embodiment such as this, the closely configured microfeatures 1514 near the center achieve the benefit of efficient heat transfer, and the close configuration does not hinder the flow of vapor because the amount of vapor accumulating in the portion of the passages 1520 near the center is relatively small. As the microfeatures 1514 extend away from each other in the direction of the pathways 1521, the passages 1520 widen in order to accommodate the accumulation of vapor along the length of the pathways 1521.

The embodiment shown in FIG. 18A is only one such example. The widening of the passages 1520 along the pathways 1521 of vapor flow can be accomplished through a variety of embodiments. For example, the passages 1520 can be irregularly shaped, and the microfeatures 1514 that define the passages 1520 can be constructed to have intermittent, as opposed to continuous, positioning along the passages 1520 accommodating the pathways 1521 upon which the vapor will travel.

Figure 18B:
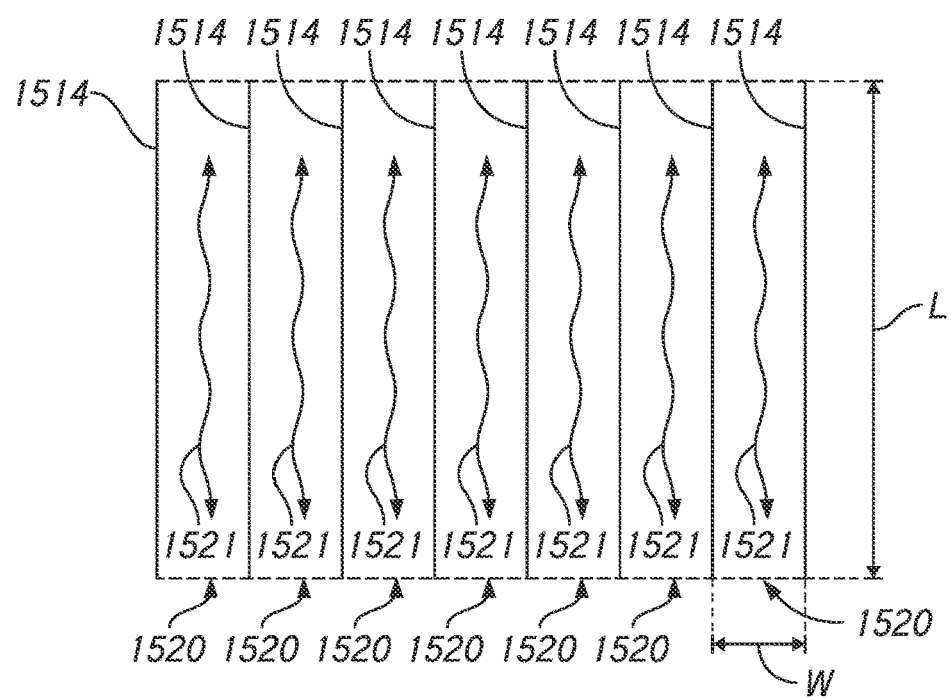
FIG. 18B schematically illustrates a parallel arrangement of an embodiment of microfeatures and the corresponding passages to accommodate the vapor pathways.

Referring now to FIG. 18B, other embodiments of the present technology may be constructed such that the microfeatures 1514 form passages 1520 that are substantially parallel. In this type of arrangement, the passages 1520 do not widen in the direction in which accumulating vapor travels but instead they maintain a substantially constant cross-sectional area along the length of the passages 1520.

Figure 18C:
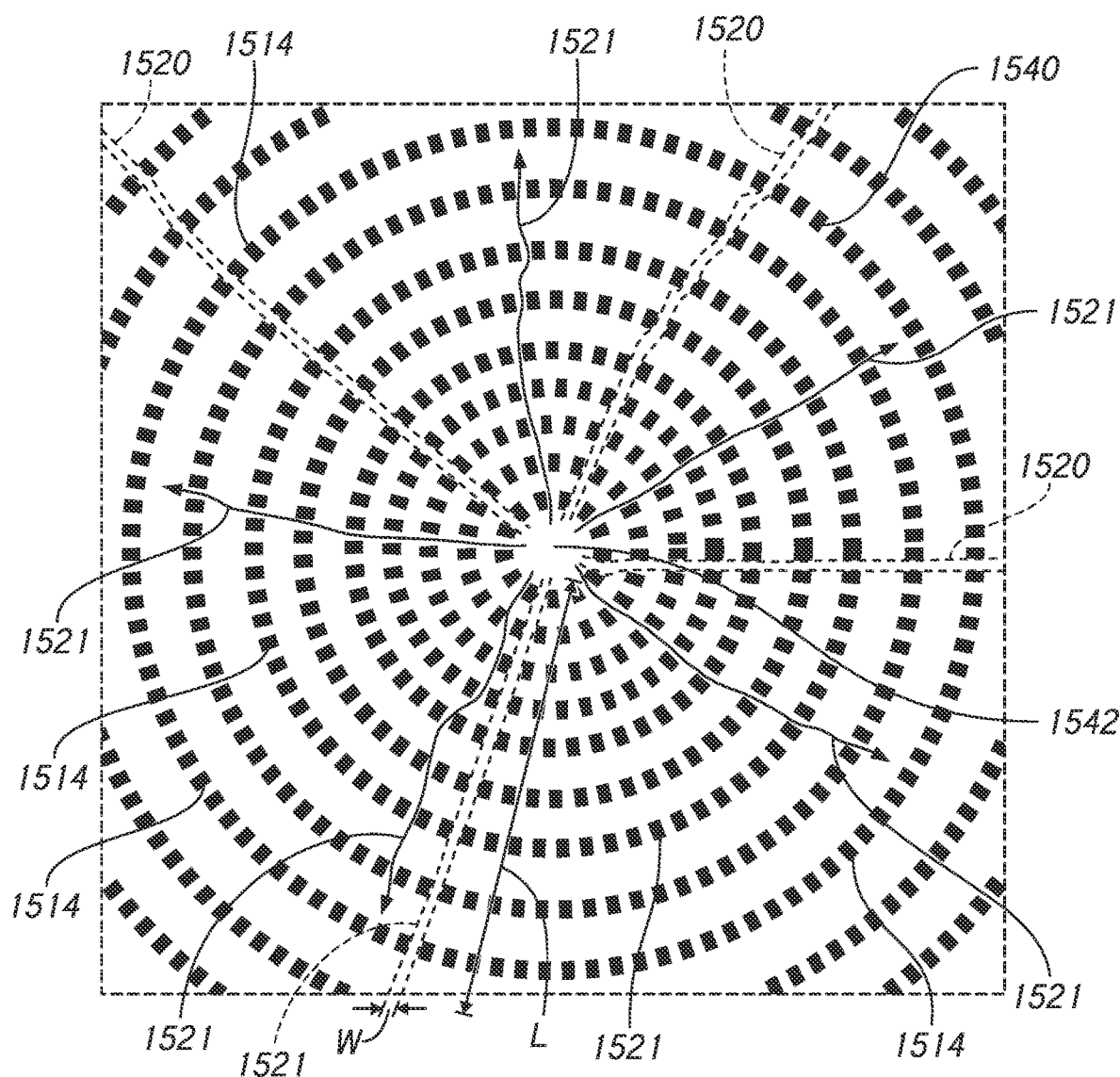
FIG. 18C schematically illustrates another embodiment of the radial arrangement with discontinuous wall or panel shaped microfeatures (panels, walls, pins, posts, or rods or similar shaped structures) to define various passages to accommodate the vapor pathways.

FIG. 18C shows another embodiment of the present technology in which the microfeatures 1514 are positioned in a radial fashion from a central point 1542. In an embodiment such as this, the microfeatures 1514 that define the passages 1520 are constructed to have intermittent, as opposed to continuous, positioning along passages 1520 to accommodate the pathways 1521 of vapor flow. This may be accomplished, for example, by utilizing microfeatures 1514 fashioned in the form of pins, posts, rods, (or similar structure) or combinations of these. This may also be accomplished, for example, by utilizing microfeatures 1514 fashioned in the form of panels or walls of intermittent length, as opposed to panels or walls that run the length of the evaporator portion of the device.

In the embodiment represented in FIG. 18C, the microfeatures 1514 are placed in an intermittent, radial fashion such that the number of available passages 1520 generally increases along the pathways 1521 upon which the accumulating vapor travels. In this manner, the overall vapor space defined by the passages 1520 may generally widen and increase along the radiating pathways 1521 upon which the accumulating vapor travels. Although as illustrated, the width of the passages remains about the same. However, as the pathway extends radially outward the population density of the elongated members (e.g., rods or pins) may decrease so that the width of the passages may increase.

Figure 18D:
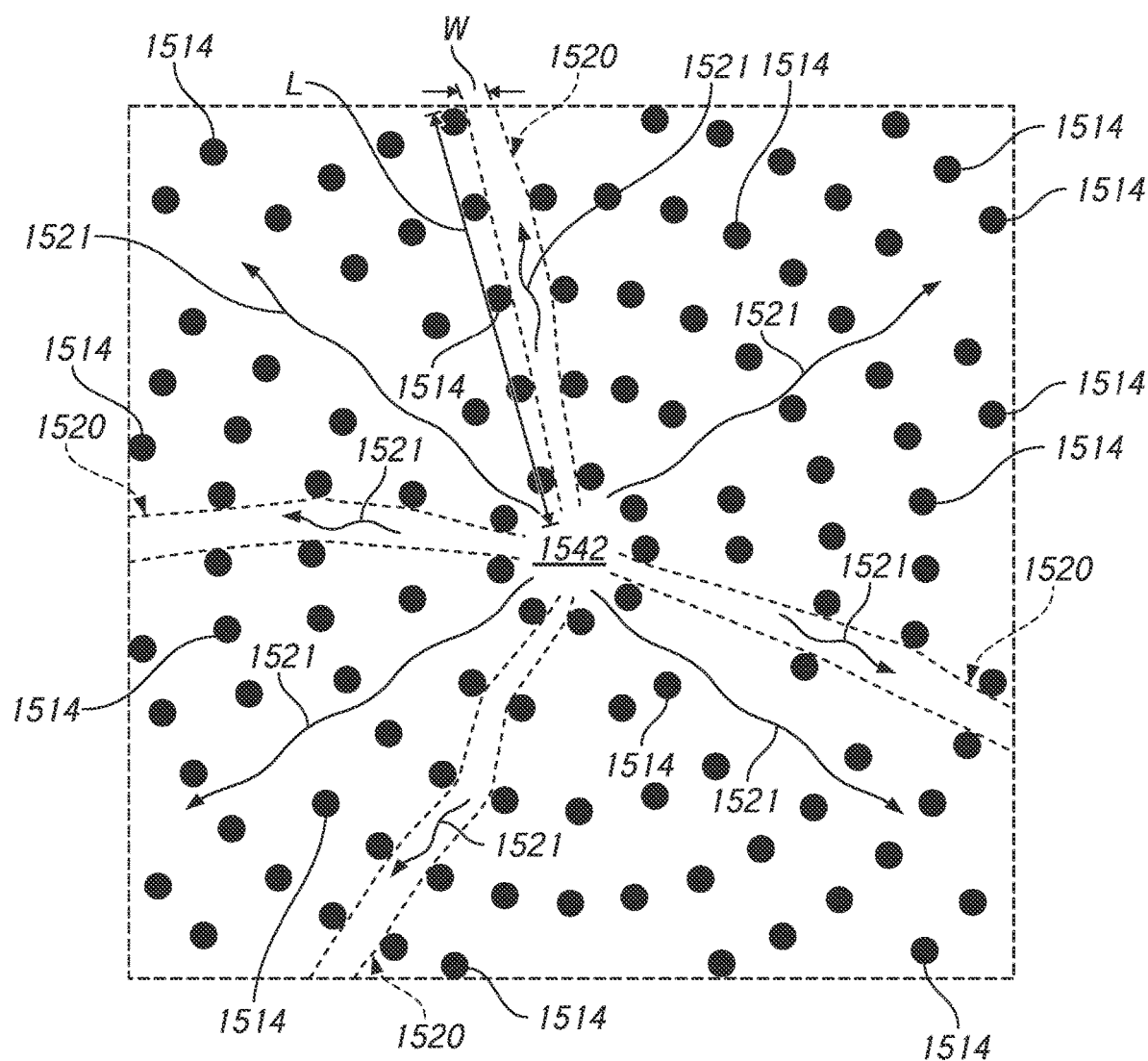
FIG. 18D schematically illustrates another embodiment of a radial arrangement of microfeatures with rods, pins, or post-shaped elongated members (or similar structure, or discontinuous wall or panel or similar shaped structures).

FIG. 18D shows yet another embodiment that uses a radial positioning of microfeatures 1514 from a central point 1542. As with other embodiments, the embodiment represented by FIG. 18D forms passages 1520 that generally increase in size and/or number along the passages 1520 to accommodate pathways 1521 of vapor flow, thus increasing the overall vapor space capable of accommodating the accumulating vapor. For instance, the elongated members in the form of pins, post or rods (or similar structure), may be more densely populated toward the center of the device compared to the outer or circumferential portion of the device.

Figure 18E:
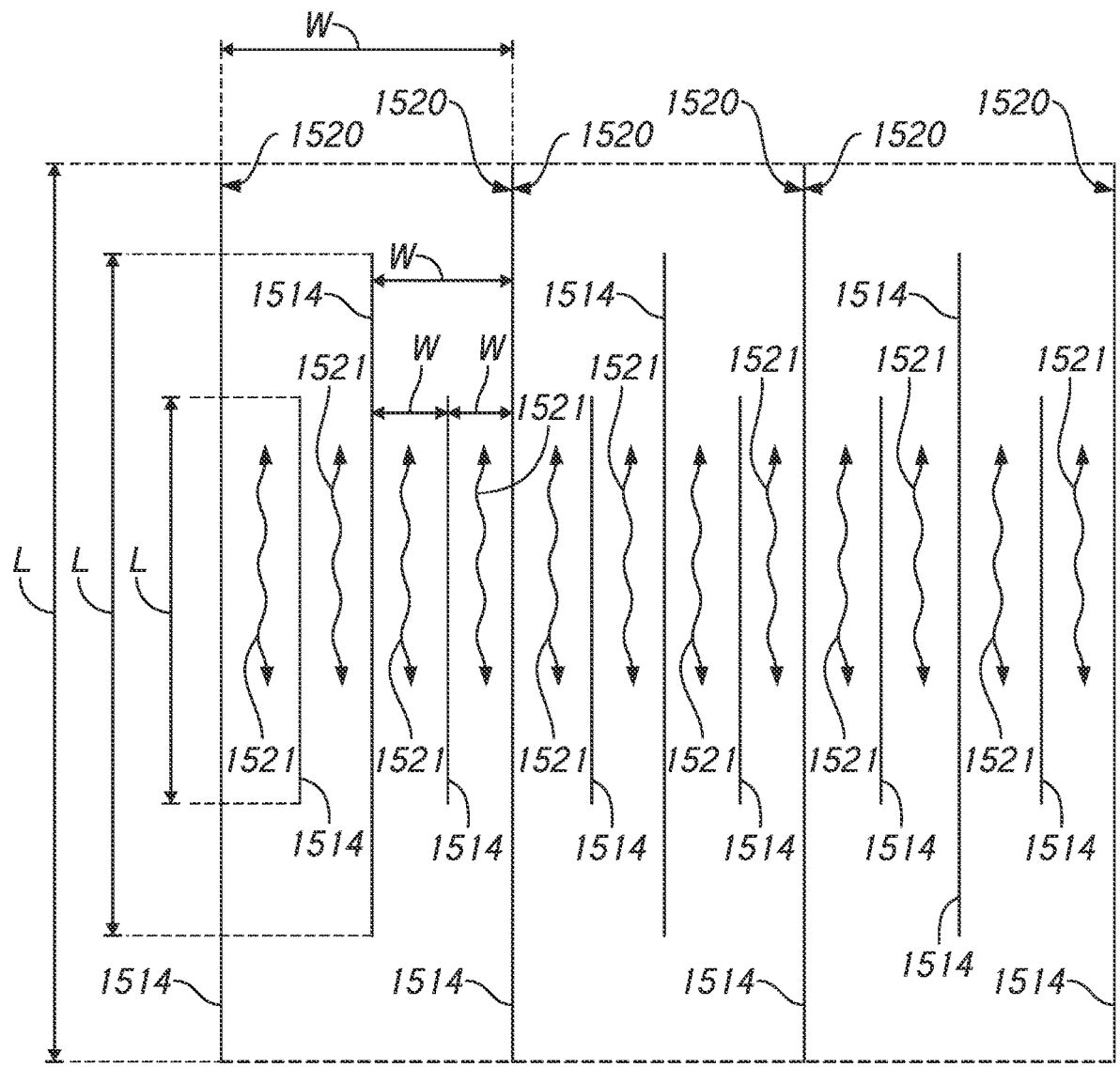
FIG. 18E schematically illustrates a parallel arrangement of microfeatures with elongated members of different lengths placed to allow the passages (e.g., channels or other structures) to widen in the pathway of vapor flow.

Referring now to FIG. 18E, some embodiments may use sections of microfeatures 1514 that are substantially parallel to each other in order to define passages 1520 that are also substantially parallel to each other. In this embodiment, the number of microfeatures 1514 within any passage 1520 generally decreases in the direction of the pathway 1521 upon which the accumulating vapor travels. This may be accomplished, for example, by positioning a number of microfeatures 1514 near the center and extending them to different lengths such that some do not extend all the way to the edge of the device, thus allowing the passages 1520 to widen and accommodate the accumulation of vapor in a variety and multitude of pathways 1521. In this manner, the overall vapor space defined by the passages generally widens and increases in the direction of the passages 1520 and pathways 1521 of vapor flow.

Referring now to FIGS. 19A-19D, some embodiments may use one or more microfeatures 1514 that are fashioned in the form of walls or panels. In some embodiments, the walls or panels may be curved or contoured. Some shapes may include multiple contours (FIG. 19A); multiple angles (FIG. 19B); single curve (FIG. 19C); and straight alignment (FIG. 19D). It should be appreciated that the different embodiments of microfeatures 1514 represented herein may be used in combination with each other or in combination with other forms. Additionally, the form of microfeatures 1514 used in any embodiment may be uniform or substantially uniform. An example of a curve design may be reflected by a spiral pattern.

FIGS. 20A-20E show additional forms of microfeatures 1514. These embodiments may be used to form one or more elongated members in the form of rods, pins, or posts (or similar). The microfeatures 1514 may have the following one or more different cross-sections: circular, oval, rectangular (or square), hexagonal, and triangular, as well as any combination thereof. Said differently, the cross section may be of any polygonal cross section or any conceivable geometrical shape. For example, the elongated members may be at least one of: triangular, triangular prism, a pyramid, a cone, and a cylinder.

According to one aspect, the heat flux generated by the semiconductor device of the present technology is dissipated by the heat-transfer unit. This heat flux can be approximated as follows. Assuming the target to be cooled is a cube of tissue with dimensions of 1 cm wide by 1 cm long by 1 mm thick, the contact cooling system is to reduce the temperature of the mass enclosed in this volume from 35° C. to 5° C., with the assumption that biological tissue is approximated as liquid water. The thermal energy which must be extracted from the target to lower its temperature from its initial temperature $T_1$ to target temperature $T_2$ is:

$$E=\rho V C_p(T_1-T_2)$$

Where $\rho$ is the material density, V is the volume, and $C_p$ is the specific heat capacity.

For the case described above, the variables are as follows:

$$\rho = 1000 \frac{kg}{m^3}$$
$$V = 10^{-2} m \times 10^{-2} m \times 10^{-3} m = 10^{-7} m^3$$
$$C_p = 4180 \frac{J}{kg \cdot C}$$
$$T_1 = 35\ C.$$
$$T_2 = 5\ C.$$

Therefore the total thermal energy E will be:

$$E=12.5\ J$$

The thermal energy will be extracted across the top face of the target which has a surface area A of:

$$A = 10^{-2}\ m \times 10^{-2}\ m = 10^{-4}\ m^2$$

For some applications including pain management in dermatology energy-based treatments, it is desired that the target temperature is reduced from 35° C. to 5° C. in a few seconds (for example 2-3 seconds).

The heat flow $Q_c$ and the heat flux $q_c$, can be calculated as $$Q_c = \frac{E}{t} = \frac{12.5\ J}{2\ s} = 6.25\ W$$
$$q_c = \frac{Q}{A} = \frac{6.25\ W}{10^{-4}\ m^2} = 62.5\ kW/m^2$$

In the thermal management system described herein, $q_c$, is the average heat flux into the cold side of the thermoelectric (Peltier) module. The heat flux out of the hot side of the thermoelectric module is determined by characteristics of the thermoelectric module and the temperatures at the hot and cold sides of the thermoelectric module. For an exemplary thermoelectric module (potted version from TE Tech module TE-65-0.6-0.8) and for the hot and cold side temperatures at −10° C. and −20° C., respectively, the heat flow on the cold and hot side of the module are:

$$Q_{C,TE}=8\ W$$

$$Q_{H,TE}=25\ W$$

Since $Q_{C,TE} > Q_C$ the thermoelectric module is capable of removing the thermal energy from the target quickly enough to meet the requirement of cooling the target from 35° C. to 5° C. in 2 seconds.

The heat flux on the hot side of the Peltier module, $q_{H,TE}$ is:

$$q_{H,TE} = \frac{Q_{H,TE}}{A_{module}} = \frac{25\ W}{156\ mm^2} = 160 \frac{kW}{m^2}$$

The two-phase cooling system mounted on the hot side of the thermoelectric Peltier module has to remove the heat at a rate specified above in order for the hybrid system to cool the target at the specified desired rate (30° C. temperature drop in 2 seconds). The cooling system is designed to provide cooling capacities as high as $$10 \frac{MW}{m^2}$$

at small temperature differences (less than 5° C.) between the heat source (Peltier module) and the working fluid. The total thermal energy which should be removed by the two-phase cooling system over the 2 seconds of operation of the system in its cooling mode is:

$$E_H = Q_H \times t = 25 W \times 2 s = 50\ J$$

The mass for the working fluid that has to turn from liquid into vapor to remove this amount of thermal energy, $E_H$ is:

$$m_{Ref} = E_H / h_{fg}$$

in which $h_{fg}$ is the latent heat of vaporization for the working fluid. Using HFO-1234ze as working fluid:

$$h_{fg} = 190\ kJ/kg$$

Therefore, the required mass for the working fluid to complete the cooling cycle is:

$$m_{Ref} = 2.63 \times 10^{-4}\ kg$$

The mass flux of evaporation is:

$$\dot{m}_{Ref} = \frac{m_{Ref}}{A_{TE} \times t} = \frac{2.63 \times 10^{-4} \text{kg}}{156 \times 10^{-6} \text{m}^2 \times 2 \text{ s}} = 0.8 \frac{\text{kg}}{\text{m}^2 \cdot \text{s}}$$

This is a large mass flux of evaporation. The contact surface area between liquid and solid to induce liquid evaporation at this rate can be calculated using equations described in U.S. Pat. No. 10,217,692. The large contact surface area between liquid and solid requires many channels or high contact surface area between the solid channels and the fluid packaged in a 1 cm×1 cm area and imposes large pressure drop on the liquid. The pressure gradient to induce such flow rate is very large. An exemplary channel design useful in the present technology is a fractal topology that enables fluid flow through the phase-change component of the system at very low-pressure gradients (or passive, i.e. self-driven, flow in some cases). The cooling system described above will have a compact footprint (less than 5 mm) and can be integrated into a wide range of energy-based tissue treatment systems and other applications. The entire system, whether made with transparent or nontransparent materials, provides ultra-fast cooling and very high controllability in a very compact package.

Another aspect of the present technology is to monitor the temperature distribution in the target material at different depths or layers within the target material during energy-based treatments. For example, one aspect is to non-invasively monitor the temperature distribution inside a volume of mammalian tissue (e.g., human tissue) using electromagnetic/mechanical waves during an energy-based therapy or treatment (e.g., laser treatments, radiation beam treatments, or cryo-based treatments such as reducing subcutaneous adipose tissue via cooling, ablating lesions (e.g., freezing lesions), etc.). In operation, the molecules of the tissue absorb, scatter, or reemit the propagating wave, and the effect of thermal energy on the molecules changes the interaction of the waves with the tissue. These changes can be detected by measuring changes in the return wave or other energy received by a detecting transducer. This can provide online/real-time temperature monitoring with high accuracy and reliability. The non-invasive nature of this aspect of the present technology provides a robust tool for accurately monitoring different types of tissue that enhances the safety and reliability of energy-based treatments and reduces the risk of damage to non-target treatment areas.

Figure 21A:
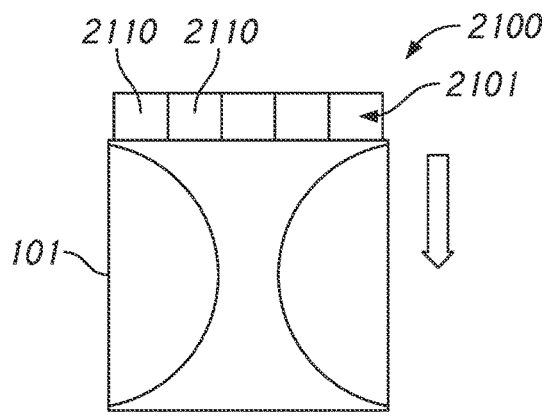
FIGS. 21A-21C are schematic views of a non-invasive temperature monitoring system for determining the temperature gradient within a target material (e.g., mammalian tissue) for use with any of the foregoing thermal management systems described with respect to FIGS. 1A-20E herein and/or any of the energy-based treatment systems described herein (e.g., subcutaneous adipose tissue reduction, laser treatments, and radiation beam treatments).
Figure 21B:
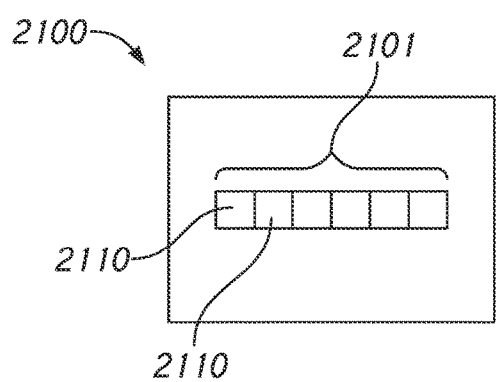
Figure 21C:
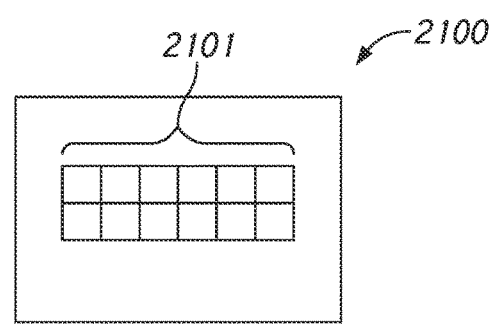
Figure 22:
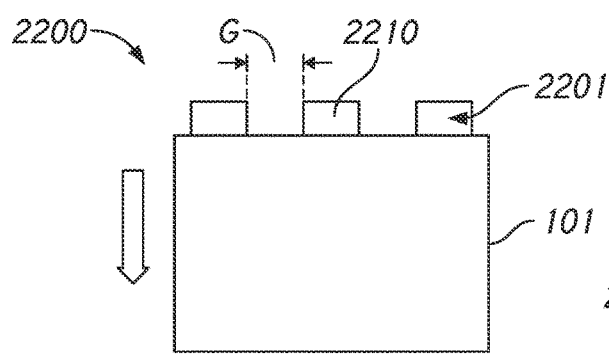
FIGS. 22 and 23 are schematic views of a non-invasive temperature monitoring system for determining the temperature gradient within a target material (e.g., mammalian tissue) for use with any of the foregoing thermal management systems described with respect to FIGS. 1A-20E herein and/or any of the energy-based treatment systems described herein (e.g., subcutaneous adipose tissue reduction, laser treatments, and radiation beam treatments).
Figure 23:
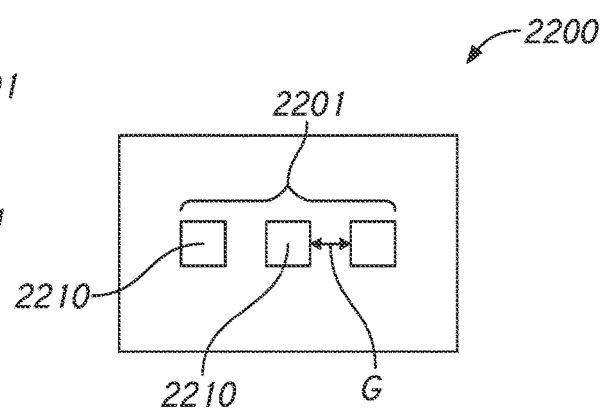

In some embodiments, a mechanical wave (e.g., ultrasound) can be applied to the tissue through an array of transducer elements (e.g., piezoelectric transducers). Referring to FIGS. 21A-21C, a non-invasive monitoring system 2100 can include an array 2101 of transducers 2110 configured to transmit ultrasonic energy to the target material 101 and detect return components of the ultrasonic energy. The transducers 2110 of the system 2100 are arranged in a single row (FIG. 21B) or in several rows (FIG. 21C). FIGS. 22 and 23 show an alternative non-invasive monitoring system 2200 having a transducer array 2201 with transducers 2210 spaced apart by gaps G. These arrangements can be a single transducer instead of an array, or in the case of an array with multiple transducers any number of transducers can be used (there is no limit on the size or number of transducers).

The arrangement of the transducers 2110 and 2210 shown in FIGS. 22A-23 are linear, but in other embodiments the transducer arrays 2101 and 2201 can be curvilinear, 1.5D array, 2_D array, convex, concave, annular, internal focus, skewing, variable angle, dual linear, dual 1.5D, or coaxial (annular). The scan of the treatment area can be along a linear path or by sweeping the wave using phased-array transducers. The frequency of the transmitted waves depends on the depth and the desired resolution.

Referring to FIGS. 21A-23, the array of transducers can produce a beam to monitor the thermal profile of the whole treatment area using different delayed phase waves. The elevation focus depth can change from a depth within the tissue of 0.5 mm to 20 cm depending on location of the region of interest.

The transducer arrays 2101 and 2201 can be located inside and/or outside of the applicator of an energy-based device. For example, the cluster of transducers in an array can be located at different areas in and/or outside of the applicator to be in contact with the tissue.

Figure 24:
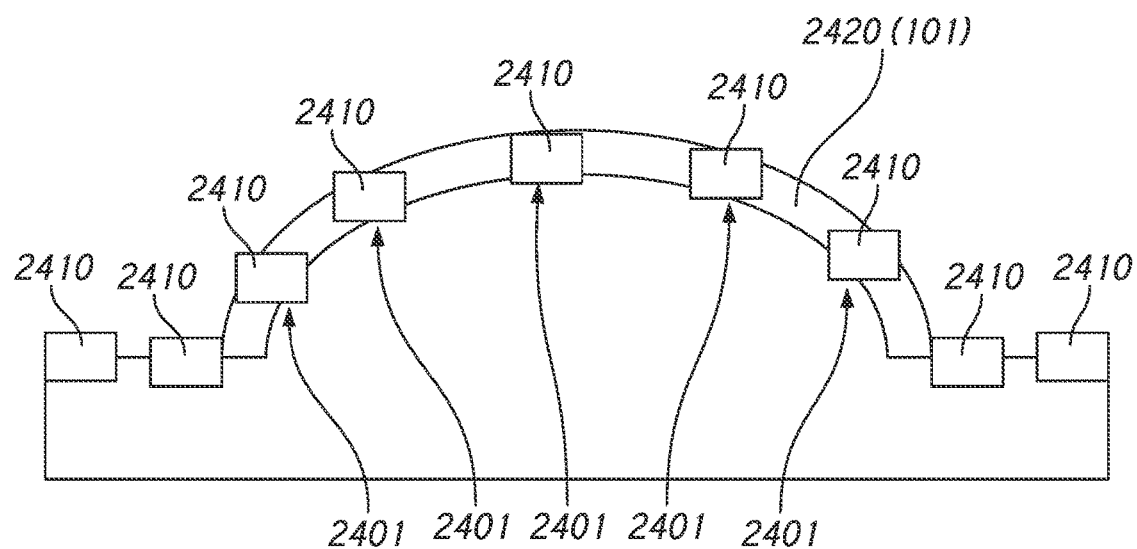
FIG. 24 is a schematic view of a non-invasive temperature monitoring system for determining the temperature gradient within a target material (e.g., mammalian tissue) for use with any of the foregoing thermal management systems described with respect to FIGS. 1A-20E herein and/or any of the energy-based treatment systems described herein (e.g., subcutaneous adipose tissue reduction, laser treatments, and radiation beam treatments).

FIG. 24 shows a non-invasive monitoring system having transducer array 2401 having transducers 2410a-b (referred to collectively as "transducers 2410") arranged on a curved energy-device applicator 2420. The energy-device application 2420 can be the contact member of any of the thermal management systems described above with reference to FIGS. 1A-20E, such as contact member 101. This is particularly useful in cryo-based applications where the contact member directly cools the epidermis to treat subcutaneous tissue, such as reducing subcutaneous adipose tissue for body sculpting. The energy-device application 2410 can alternatively be a component of a laser system or radiation beam system that heats the target material. The non-invasive monitoring system can have first transducers 2410a inside the applicator 2420 contacting the tissue and second transducers 2410b outside of the applicator 2420 that are also contacting the tissue. The thermal distribution inside the tissue changes over time and can be monitored constantly or episodically. This can be done by turning the transducers on/off or activating them continuously throughout a procedure.

Other embodiments of non-invasive tissue monitoring use polarized electromagnetic (EM) waves with wavelengths up to 100000 µm. These waves are either transmitted, reflected, absorbed, refracted, diffracted, or scattered as they travel through tissue. For example, during an energy-based treatment, the applied energy changes the temperature of the tissue, which alters its behavior/response to an EM wave. The variation in the temperature of the tissue at various depths within the tissue can thus be monitored through measuring the changes in the polarization, amplitude, wavelength, frequency, time of flight, phase shift, and the intensity of the EM wave.

Figure 25:
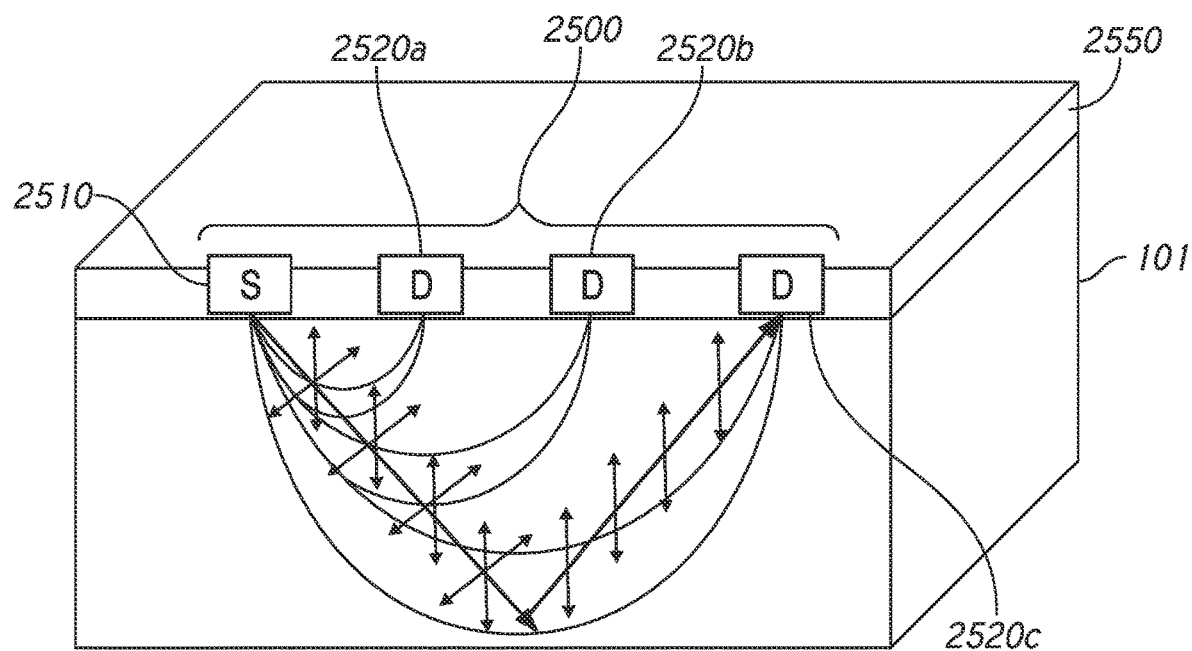
FIG. 25 is a schematic view of a non-invasive temperature monitoring system for determining the temperature gradient within a target material (e.g., mammalian tissue) for use with any of the foregoing thermal management systems described with respect to FIGS. 1A-20E herein and/or any of the energy-based treatment systems described herein (e.g., subcutaneous adipose tissue reduction, laser treatments, and radiation beam treatments).

FIG. 25 shows a non-invasive monitoring system 2500 having at least one EM source 2510 and at least one EM detector 2520. In the illustrated embodiment, the system 2500 has one EM source 2510 and three EM detectors 2520a-c (referred to collectively as "EM detectors 2520"), but any number of EM sources 2510 and EM detectors 2520 can be used. The EM source(s) 2510 and EM detectors 2520 can be mounted to an applicator 2550, such as the contact member of any of the foregoing thermal management systems described above with reference to FIGS. 1A-20E or any laser/radiation type tissue treatment device. The distance between the source 2510 and the detectors 2520 is a function of the depth of the target treatment area in the tissue, such as 0.5 mm to several centimeters. The arrangement of the source(s) 2510 and detectors 2520 depends on the thermal profile progression of the cooling/heating treatment through the tissue. In operation, one or more EM waves are transmitted to the target material 101 (e.g., mammalian tissue) via the source 2510 and the backscattered energy is recorded by the detectors 2520. In this embodiment, the EM travels through a banana-shape pathway to the detectors 2520.

Figure 26:
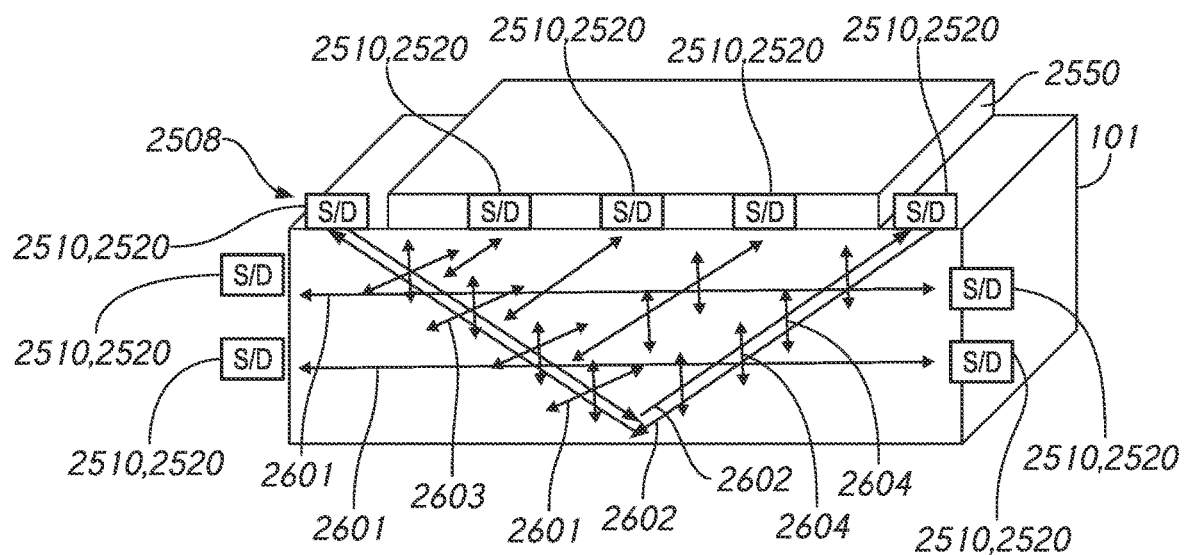
FIG. 26 is a schematic view of a non-invasive temperature monitoring system for determining the temperature gradient within a target material (e.g., mammalian tissue) for use with any of the foregoing thermal management systems described with respect to FIGS. 1A-20E herein and/or any of the energy-based treatment systems described herein (e.g., subcutaneous adipose tissue reduction, laser treatments, and radiation beam treatments).

FIG. 26 illustrates another embodiment in which several sources 2510 and several detectors 2520 are at different locations and distances from each other. The sources 2510 and detectors 2520 can produce/detect EM waves 2610 that are received directly from a source 2510 to a detector 2510 or EM waves 2602 can be curved (e.g., banana-shaped) or otherwise not directly linear. The arrows 2603 and 2604 indicate the polarization axes of the EM waves 2602. The sources 2510 and detectors 2520 can be placed at any location inside or outside of the applicator on or around the treatment area. One aspect of this embodiment is the vertically arranged sources 2510 and detectors 2520 at the sides are useful in applications where the tissue is not flat (elevated or pinched) and the treatment is being applied on the top of the tissue and/or along the sides of tissue. In this case, EM waves 2601 can pass directly across the thermal profile direction. As a result, as the thermal profile penetrates deeper into the tissue the lower detectors 2520 of the vertically arranged detectors 2520 can measure the temperature gradient as a function of depth in the tissue.

When the EM waves travel along a banana-shaped pathway, increasing the distance between a source 2510 and a detector 2520 increases the depth within the target material that can be monitored. Placing several detectors at different distances from the source provides monitoring of different layers at different depths of a volume of tissue. In another embodiment, EM waves travelling through the medium can be collected by a polarized light detector or via a regular detector. The collected information via a regular detector can be further processed to detect the effect of temperature changes on polarizing the light.

Figure 27:
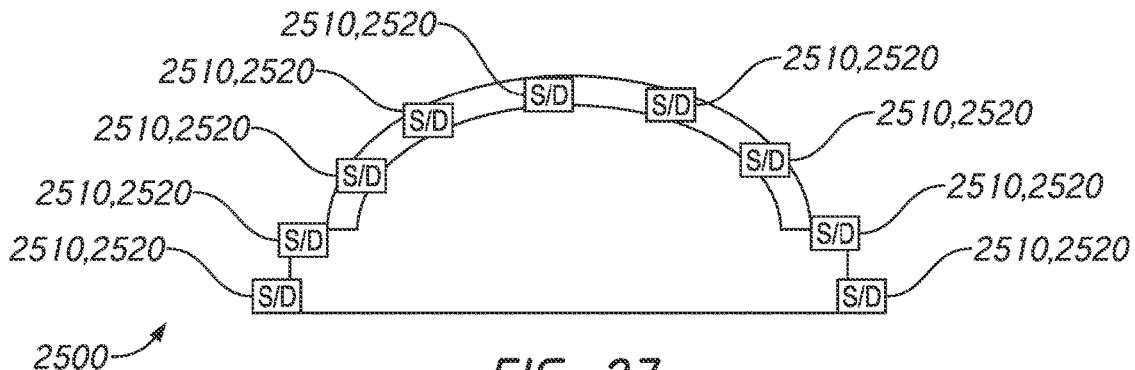
FIG. 27 is a schematic view of a non-invasive temperature monitoring system for determining the temperature gradient within a target material (e.g., mammalian tissue) for use with any of the foregoing thermal management systems described with respect to FIGS. 1A-20E herein and/or any of the energy-based treatment systems described herein (e.g., subcutaneous adipose tissue reduction, laser treatments, and radiation beam treatments).
Figure 28:
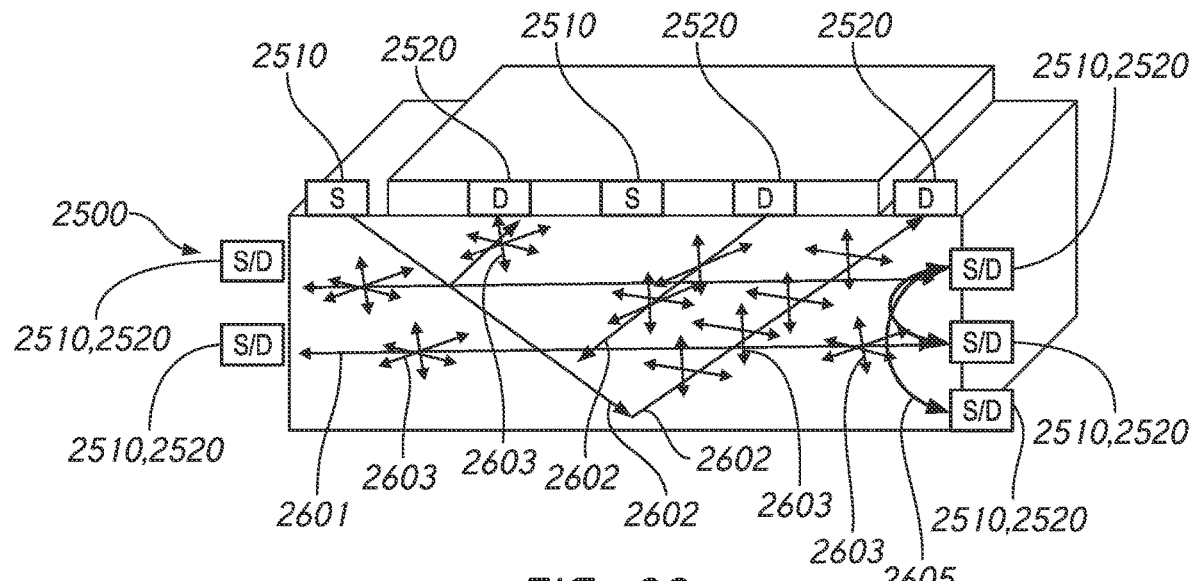
FIG. 28 is a schematic view of a non-invasive temperature monitoring system for determining the temperature gradient within a target material (e.g., mammalian tissue) for use with any of the foregoing thermal management systems described with respect to FIGS. 1A-20E herein and/or any of the energy-based treatment systems described herein (e.g., subcutaneous adipose tissue reduction, laser treatments, and radiation beam treatments).

FIG. 27 shows an embodiment of the non-invasive monitoring system 2500 with an arrangement of sources 2510 and detectors 2520 on a curved applicator 2550. FIG. 28 shows another embodiment of the non-invasive monitoring system 2500 with a specific arrangement of sources 2510 and detectors 2520. As shown in FIG. 28, the vertical sources 2510 and detectors 2520 can transmit/detect EM waves 2605 along the sides of the target material 101. The sources 2510 and detectors 2520 can be switched on/off or constantly activated. The detectors can be paired only with one or several sources at a time.

In operation, the thermal properties and optical characteristics of a medium vary with temperature, which in turn effects the polarization angle or/and the direction of the unpolarized/polarized EM waves. Through monitoring the changes in polarization angle or/and the direction of the polarized EM waves, the temperature distribution inside the tissue at different depths and locations can be determined. The preprocessing of the transmitted EM waves and post processing of the received EM waves, along with an appropriate hardware and source/detector arrangement, enables accurate, real-time determination of the temperature gradient within a volume of tissue. As a result, the non-invasive monitoring systems 2500 provide a robust tool to control heating and cooling therapies.

One application of the non-invasive monitoring system 2500 is to limit the freezing front in adipose tissue. For example, based on a thickness of the adipose tissue, cooling is continued until the refraction, extinction, absorption, scattering coefficients, amplitude, time of flight and the phase shift for the received signal becomes constant. Different wavelengths can also be used to monitor different components of the tissue like fat, water, and muscle separately. To prevent the cooling front from reaching the non-target areas, the variations in the received signal from the non-target areas should remain unchanged during the treatment. For example, using a least-mean-square computation, or other computational method such as recursive least square, adaptive filters, empirical mode decomposition, or blind source separation, the signals from the detectors 2520 can be processed to determine the temperature gradient from the epidermal layer through the subcutaneous adipose tissue.

From the foregoing, it will be appreciated that specific embodiments of the technology have been described herein for purposes of illustration, but that various modifications may be made without deviating from the disclosure. Accordingly, the invention is not limited except as by the appended claims. Furthermore, certain aspects of the new technology described in the context of particular embodiments may also be combined or eliminated in other embodiments. Moreover, although advantages associated with certain embodiments of the new technology have been described in the context of those embodiments, other embodiments may also exhibit such advantages and not all embodiments need necessarily exhibit such advantages to fall within the scope of the technology. Accordingly, the disclosure and associated technology can encompass other embodiments not expressly shown or described herein.

EXAMPLES

Those having skill in the art, with the knowledge gained from the present technology, will understand that various combinations of embodiments and features from embodiments are within the scope of the present technology. Examples of such combinations, which are not limiting, are set forth in the following listing of numbered clauses.

1. A thermal management system, comprising:
   a thermoelectric component having a first side configured to be thermally coupled to a target material and a second side opposite the first side;
   a two-phase heat transfer unit thermally coupled to the second side of the thermoelectric component, the two-phase heat transfer unit having 1) a phase-transition chamber having an inlet region and an outlet region, 2) microfeatures in the phase-transition chamber spaced apart from each other such the microfeatures induce capillary forces to a working fluid that drives the working fluid from the inlet region of the phase-transition chamber to the outlet of the phase-transition chamber, 3) an inlet through which the working fluid flows into the two-phase heat transfer unit in a liquid phase, and 4) an outlet through which at least a portion of the working fluid flows out of the two-phase heat transfer unit in a vapor phase; and
   a controller configured to operate the thermoelectric component and the two-phase heat transfer unit such that the two-phase heat transfer unit cools the second side of the thermoelectric component to a first temperature and the thermoelectric component changes the temperature of the target material to a second temperature within 0.5-20 seconds, and wherein the second temperature is +/−60° C. of the first temperature.

2. The system of clause 1 wherein the contact member, thermoelectric component, and the two-phase heat transfer unit together have a height measured along the direction of heat flow from the contact member through the thermoelectric component of 2 mm to 25 mm.

3. The system of any of clauses 1 and 2 wherein the controller is configured to set the two-phase heat transfer unit to a first temperature of 5° C. to −20° C. at the second side of the thermoelectric unit, and the controller is configured to operate the thermoelectric unit to heat the contact member to a second temperature of 20° C. to 40° C. in 1-10 seconds.

4. The system of any of clauses 1-3 wherein the two-phase heat transfer unit has a thickness measured in the direction of the heat flow from the thermoelectric component of 3 mm to 8 mm.

5. The system of any of clauses 1-4 wherein the microfeatures are spaced apart from each other by 10 microns to 1,000 microns.

6. The system of clause 5 wherein the microfeatures are channels defined by walls extending from the inlet region to the outlet region of the phase-transition chamber.

7. The system of clause 5 wherein the microfeatures are pins in the phase-transition chamber.

8. The system of any of clauses 1-7 wherein the microfeatures are spaced apart from each other by 10 microns to 250 microns.

9. The system of any of clauses 1-8 wherein:
the thermoelectric component comprises a first Peltier module;
the system further comprises a second Peltier module positioned laterally of the first Peltier module;
the phase-transitions chamber of the two-phase heat transfer unit comprises a first phase-transition chamber; and
the two-phase heat transfer unit further comprises a second phase-transition chamber positioned laterally of the first phase-transition chamber, and the first phase-transition chamber is aligned with the first Peltier module and the second phase-transition chamber is aligned with the second Peltier module.

10. The system of clause 9 wherein the controller is configured to set the two-phase heat transfer unit to a first temperature of 5° C. to −20° C. at the second side of the thermoelectric unit, and the controller is configured to operate the thermoelectric unit to heat the contact member to a second temperature of 10° C. to 40° C. in 1-10 seconds.

11. The system of any of clauses 9 and 10 wherein the two-phase heat transfer unit has a thickness measured in the direction of the heat flow from the thermoelectric component of 2 mm to 8 mm.

12. The system of any of clauses 9-11 wherein the microfeatures are spaced apart from each other by 10 microns to 1,000 microns.

13. The system of clause 12 wherein the microfeatures are channels defined by walls extending from the inlet region to the outlet region of the phase-transition chamber.

14. The system of clause 12 wherein the microfeatures are pins in the phase-transition chamber.

15. The system of any of clauses 9-14 wherein the microfeatures are spaced apart from each other by 10 microns to 250 microns.

16. The system of any of clauses 9-15 wherein the thermoelectric component has a first volumetric heat capacity and the two-phase heat transfer unit has a second volumetric heat capacity such that second volumetric heat capacity is not more than one of 50%, 100%, 150%, 200%, 250%, 300%, 400%, or 500% of the first volumetric heat capacity.

17. The system of any of clauses 9-16, further comprising a condenser fluidically coupled to the inlet and outlet of the two-phase heat-transfer unit, wherein the working fluid is contained within the condenser and the two-phase heat transfer unit.

18. A method of thermally managing a target material, comprising:
positioning a first side of a thermoelectric component to be thermally coupled to a target material; cooling a second side of the thermoelectric component to a first temperature using a two-phase heat transfer unit thermally coupled to the second side of the thermoelectric component; and
adjusting electrical current through the thermoelectric component such that target material is at second temperature within 0.5-20 seconds, and wherein the second temperature is +/−60° C. of the first temperature.

19. The method of clause 18 wherein the thermoelectric component and the two-phase heat transfer unit together have a height measured along the direction of heat flow through the thermoelectric component of 5 mm to 25 mm.

20. The method of any of clauses 18 and 19 wherein the first temperature is 5° C. to −20° C. at the second side of the thermoelectric unit, the second temperature is 20° C. to 40° C., and the time to go from the first temperature to the second temperature is 1-10 seconds.

21. The method of any of clauses 18-20 wherein the two-phase heat transfer unit has a thickness measured in the direction of the heat flow from the thermoelectric component of 3 mm to 8 mm.

22. The method of any of clauses 18-21 wherein the microfeatures are spaced apart from each other by 10 microns to 1,000 microns.

23. The method of any of clauses 18-22 wherein the microfeatures are channels defined by walls extending from the inlet region to the outlet region of the phase-transition chamber.

24. The method of any of clauses 18-22 wherein the microfeatures are pins in the phase-transition chamber.

25. The system or method of any of clauses 1-24, further comprising a non-invasive monitoring system having a source that transmits an energy to the target material and a detector that detects a component of the energy transmitted to the target material by the source, and wherein a temperature gradient in the target material is determined by information from the detector.

26. The system or method of any of clauses 1-26 wherein the source is a light source and the detector is a light detector.

27. A device for treating tissue of a person, comprising:
a tissue heating module configured to heat target tissue to a therapy temperature; and
a thermal management system including—
(a) a contact plate having a high thermal conductivity;
(b) a thermoelectric component having a first side configured to be thermally coupled to the contact plate and a second side opposite the first side;
(c) a two-phase heat transfer unit thermally coupled to the second side of the thermoelectric component, the two-phase heat transfer unit having 1) a phase-transition chamber having an inlet region and an outlet region, 2) microfeatures in the phase-transition chamber spaced apart from each other such the microfeatures induce capillary forces to a working fluid that drives the working fluid from the inlet region of the phase-transition chamber to the outlet of the phase-transition chamber, 3) an inlet through which the working fluid flows into the two-phase heat transfer unit in a liquid phase, and 4) an outlet through which at least a portion of the working fluid flows out of the two-phase heat transfer unit in a vapor phase; and (d) a controller configured to operate the thermoelectric component and the two-phase heat transfer unit such that the two-phase heat transfer unit cools the second side of the thermoelectric component to a first temperature and the thermoelectric component changes the temperature of the contact plate to a second temperature within 0.5-20 seconds, and wherein the second temperature is +/−60° C. of the first temperature.

28. The device of clause 27, wherein the tissue heating module comprises a laser configured to heat the target tissue to the therapy temperature while the contact plate cools adjacent tissue.

29. The device of any of clauses 27 and 28, further comprising a non-invasive monitoring system having a source that transmits an energy to the target material and a detector that detects a component of the energy transmitted to the target material by the source, and wherein a temperature gradient in the target material is determined by information from the detector.

30. The device of clause 29 wherein the source is a light source and the detector is a light detector.

31. A device for cooling tissue of a person, comprising:
a contact plate having a high thermal conductivity;
a thermoelectric component having a first side configured to be thermally coupled to the contact plate and a second side opposite the first side;
a two-phase heat transfer unit thermally coupled to the second side of the thermoelectric component, the two-phase heat transfer unit having 1) a phase-transition chamber having an inlet region and an outlet region, 2) microfeatures in the phase-transition chamber spaced apart from each other such the microfeatures induce capillary forces to a working fluid that drives the working fluid from the inlet region of the phase-transition chamber to the outlet of the phase-transition chamber, 3) an inlet through which the working fluid flows into the two-phase heat transfer unit in a liquid phase, and 4) an outlet through which at least a portion of the working fluid flows out of the two-phase heat transfer unit in a vapor phase; and
a controller configured to operate the thermoelectric component and the two-phase heat transfer unit such that the two-phase heat transfer unit cools the second side of the thermoelectric component to a first temperature and the thermoelectric component changes the temperature of the contact plate to a second temperature within 0.5-20 seconds, and wherein the second temperature is +/−60° C. of the first temperature.

32. The device of clause 31, further comprising a non-invasive monitoring system having a source that transmits an energy to the target material and a detector that detects a component of the energy transmitted to the target material by the source, and wherein a temperature gradient in the target material is determined by information from the detector.

33. The device of clause 32 wherein the source is a light source and the detector is a light detector.

34. A semiconductor device, comprising:
a semiconductor component having integrated circuitry; and
a thermal management system including—
(a) a thermoelectric component having a first side configured to be thermally coupled to the semiconductor component and a second side opposite the first side;
(b) a two-phase heat transfer unit thermally coupled to the second side of the thermoelectric component, the two-phase heat transfer unit having 1) a phase-transition chamber having an inlet region and an outlet region, 2) microfeatures in the phase-transition chamber spaced apart from each other such the microfeatures induce capillary forces to a working fluid that drives the working fluid from the inlet region of the phase-transition chamber to the outlet of the phase-transition chamber, 3) an inlet through which the working fluid flows into the two-phase heat transfer unit in a liquid phase, and 4) an outlet through which at least a portion of the working fluid flows out of the two-phase heat transfer unit in a vapor phase; and
(c) a controller configured to operate the thermoelectric component and the two-phase heat transfer unit such that the two-phase heat transfer unit cools the second side of the thermoelectric component to a first temperature and the thermoelectric component changes the temperature of the semiconductor component to second temperature.

35. The semiconductor device of clause 34 wherein the semiconductor component is a controller.

36. The semiconductor device of clause 34 wherein the semiconductor component is a memory device.

37. The semiconductor device of clause 34 wherein semiconductor component is in a server 38. A method for altering the temperature of tissue of a patient comprising
(a) thermally contacting a device comprising a thermoelectric component to the outer surface of a first tissue target at a first temperature $T_1$, wherein a heat-transfer unit thermally contacts the thermoelectric component,
(b) activating current through the thermoelectric component in a first direction to cause cooling of the outer surface of the first tissue target from the first temperature $T_1$ to between about 8° C. to about −15° C. in about 2 to 4 seconds, wherein a heat-transfer unit removes heat flux generated by the thermoelectric component to maintain the thermoelectric component at an operating temperature of at least below 50° C.,
(c) activating current through the thermoelectric component in a second direction opposite the first direction to cause heating of the outer surface of the first tissue target from between about 8° C. to about −15° C. to at least about 20° C. in about 1 to about 3 seconds.

39. The method of clause 38 wherein the first tissue target is irradiated with laser light or impacted with a needle after step (b) and before step (c).

40. The method of clause 38 wherein the first tissue target is irradiated with laser light after step (b) and before step (c) while the device remains in contact with the first tissue target.

41. The method of clause 38 wherein the first tissue target is impacted with a needle after step (b) and before step (c) while the device remains in contact with the first tissue target.

42. The method of clause 38 wherein the heat-transfer unit is a two-phase heat evaporative transfer device.

43. The method of clause 38 wherein the heat-transfer unit is a two-phase evaporative heat transfer device including an evaporative system comprising a plurality of walls extending downwardly from a base into a reservoir of evaporative fluid.

44. The method of clause 38 wherein the heat-transfer unit is a two-phase evaporative heat transfer device that has a condenser unit operatively connected thereto to receive vapor from the two-phase evaporative heat transfer device and to condense the vapor into evaporative fluid.

45. The method of clause 38 wherein the heat-transfer unit is a two-phase heat evaporative heat transfer device connected to inflow and outflow conduits for the passage of evaporative fluid therethrough.

46. The method of clause 38 wherein in step (b) activating current through the thermoelectric component in a first direction causes cooling of the outer surface of the first tissue target from the first temperature $T_1$ to between about 8° C. to about −2° C. in about 3 seconds.

47. The method of clause 38 wherein in step (b) activating current through the thermoelectric component in a first direction causes cooling of the outer surface of the first tissue target from the first temperature $T_1$ to between about 4° C. to about −2° C. in about 2 to 4 seconds.

48. The method of clause 38 wherein in step (b) activating current through the thermoelectric component in a first direction causes cooling of the outer surface of the first tissue target from the first temperature $T_1$ to between about 4° C. to about −2° C. in about 3 seconds.

49. The method of clause 38 wherein in step (c) activating current through the thermoelectric component in a second direction opposite the first direction causes heating of the outer surface of the first tissue target from between about 8° C. to about −2° C. to at least about 20° C. in about 2 seconds.

50. The method of clause 38 wherein the device includes a transparent material and laser light is transmitted through the transparent material to the first tissue target surface to treat the first tissue target.

51. The method of clause 38 wherein the device includes one or more channels through the device through which laser light is transmitted to the first tissue target surface to treat the first tissue target.

52. The method of clause 38 wherein the device includes one or more channels through the device through which one or more needles are transmitted to impact the first tissue target surface to treat the first tissue target.

53. The method of clause 38 wherein the device is attached to a handheld laser emitting device in a manner to receive laser light from the handheld laser emitting device.

54. The method of clause 38 further comprising thermally contacting the device to the outer surface of a second tissue target and repeating steps (a) to (c).

55. The method of clause 38 further comprising repeating steps (a) to (c) upon a plurality of target tissues in series.

56. The method of clause 38 wherein the device includes a plurality of thermoelectric components connected electrically in series and thermally in parallel.

57. The method of clause 38 wherein the device includes a plurality of thermoelectric components connected electrically in series and thermally in parallel and wherein each thermoelectric component has an associated microchannel evaporative structure positioned adjacent thereto to remove heat from the thermoelectric component.

58. The method of clause 38 wherein the thermoelectric component is electrically connected to a programmable power source.

59. The method of clause 38 wherein the device includes a plurality of thermoelectric components connected electrically in series and thermally in parallel and wherein the plurality of thermoelectric components is electrically connected to as programmable power source.

What is claimed is:

1. A thermal management system, comprising:
a thermoelectric component having a first side configured to be thermally coupled to a target material and a second side opposite the first side;
a two-phase heat transfer unit thermally coupled to the second side of the thermoelectric component, the two-phase heat transfer unit having 1) a phase-transition chamber having an inlet region and an outlet region, 2) microfeatures in the phase-transition chamber spaced apart from each other such the microfeatures induce capillary forces to a working fluid that drives the working fluid from the inlet region of the phase-transition chamber to the outlet of the phase-transition chamber, 3) an inlet through which the working fluid flows into the two-phase heat transfer unit in a liquid phase, and 4) an outlet through which at least a portion of the working fluid flows out of the two-phase heat transfer unit in a vapor phase; and
a controller configured to operate the thermoelectric component and the two-phase heat transfer unit such that the two-phase heat transfer unit cools the second side of the thermoelectric component to a first temperature and the thermoelectric component changes the temperature of the target material to a second temperature within a range of 0.5-to 20 seconds, and wherein the second temperature is +/−60 ° C. of the first temperature.

2. The system of claim 1, further comprising a contact member thermally coupled to the thermoelectric component, wherein the contact member, the thermoelectric component, and the two-phase heat transfer unit together have a height measured along the direction of heat flow from the contact member through the thermoelectric component of 2 mm to 25 mm.

3. The system of claim 2 wherein the controller is configured to set the two-phase heat transfer unit to a first temperature of 5 ° C. to −20 ° C. at the second side of the thermoelectric unit, and the controller is configured to operate the thermoelectric unit to heat the contact member to a second temperature of 20 ° C. to 40 ° C. in 1-to 10 seconds.

4. The system of claim 2 wherein the two-phase heat transfer unit has a thickness measured in the direction of the heat flow from the thermoelectric component of 3 mm to 8 mm.

5. The system of claim 2 wherein the microfeatures are spaced apart from each other by 10 microns to 1,000 microns.

6. The system of claim 5 wherein the microfeatures are channels defined by walls extending from the inlet region to the outlet region of the phase-transition chamber.

7. The system of claim 5 wherein the microfeatures are pins in the phase-transition chamber.

8. The system of claim 2 wherein the microfeatures are spaced apart from each other by 10 microns to 250 microns.

9. The system of claim 1 wherein:
the thermoelectric component comprises a first Peltier module;
the system further comprises a second Peltier module positioned laterally of the first Peltier module;
the phase-transitions chamber of the two-phase heat transfer unit comprises a first phase-transition chamber; and
the two-phase heat transfer unit further comprises a second phase-transition chamber positioned laterally of the first phase-transition chamber, and the first phase-transition chamber is aligned with the first Peltier module and the second phase-transition chamber is aligned with the second Peltier module.

10. The system of claim 9 wherein the controller is configured to set the two-phase heat transfer unit to a first temperature of 5 ° C. to −20 ° C. at the second side of the thermoelectric unit, and the controller is configured to operate the thermoelectric unit to heat the contact member to a second temperature of 10 ° C. to 40 ° C. in 1-10 seconds.

11. The system of claim 10 wherein the two-phase heat transfer unit has a thickness measured in the direction of the heat flow from the thermoelectric component of 2 mm to 8 mm.

12. The system of claim 10 wherein the microfeatures are spaced apart from each other by 10 microns to 1,000 microns.

13. The system of claim 12 wherein the microfeatures are channels defined by walls extending from the inlet region to the outlet region of the phase-transition chamber.

14. The system of claim 12 wherein the microfeatures are pins in the phase-transition chamber.

15. The system of claim 10 wherein the microfeatures are spaced apart from each other by 10 microns to 250 microns.

16. The system of claim 1 wherein the thermoelectric component has a first volumetric heat capacity and the two-phase heat transfer unit has a second volumetric heat capacity such that second volumetric heat capacity is not more than one of 50%, 100%, 150%, 200%, 250%, 300%, 400%, or-and 500% of the first volumetric heat capacity.

17. The system of claim 1, further comprising a condenser fluidically coupled to the inlet and outlet of the two-phase heat-transfer unit, wherein the working fluid is contained within the condenser and the two-phase heat transfer unit.

18. The system of claim 1, further comprising a non-invasive monitoring system having a source that transmits an energy to the target material and a detector that detects a component of the energy transmitted to the target material by the source, and wherein a temperature gradient in the target material is determined by information from the detector.

19. The system of claim 18 wherein the source is a light source and the detector is a light detector.

20. A semiconductor device, comprising:
a semiconductor component having integrated circuity; and
a thermal management system including—
(a) a thermoelectric component having a first side configured to be thermally coupled to the semiconductor component and a second side opposite the first side;
(b) a two-phase heat transfer unit thermally coupled to the second side of the thermoelectric component, the two-phase heat transfer unit having 1) a phase-transition chamber having an inlet region and an outlet region, 2) microfeatures in the phase-transition chamber spaced apart from each other such the microfeatures induce capillary forces to a working fluid that drives the working fluid from the inlet region of the phase-transition chamber to the outlet of the phase-transition chamber, 3) an inlet through which the working fluid flows into the two-phase heat transfer unit in a liquid phase, and 4) an outlet through which at least a portion of the working fluid flows out of the two-phase heat transfer unit in a vapor phase; and
(c) a controller configured to operate the thermoelectric component and the two-phase heat transfer unit such that the two-phase heat transfer unit cools the second side of the thermoelectric component to a first temperature and the thermoelectric component changes the temperature of the semiconductor component to second temperature.

21. The semiconductor device of claim 20 wherein the semiconductor component is a controller.

22. The semiconductor device of claim 20 wherein the semiconductor component is a memory device.

23. The semiconductor device of claim 20 wherein the semiconductor component is in a server.

* * * * *